US006589976B1

(12) United States Patent
Fischer et al.

(10) Patent No.: US 6,589,976 B1
(45) Date of Patent: Jul. 8, 2003

(54) UTILIZING SPIROCYCLIC PHENYL KETO-ENOLS AS PESTICIDES AND HERBICIDES

(75) Inventors: Reiner Fischer, Monheim (DE); Thomas Bretschneider, Lohmar (DE); Christoph Erdelen, Leichlingen (DE); Ulrike Wachendorff-Neumann, Neuwied (DE); Markus Dollinger, Overland Park, KS (US); Andreas Turberg, Haan (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/509,288

(22) PCT Filed: Sep. 12, 1998

(86) PCT No.: PCT/EP98/05809
§ 371 (c)(1),
(2), (4) Date: Mar. 21, 2000

(87) PCT Pub. No.: WO99/16748
PCT Pub. Date: Apr. 8, 1999

(30) Foreign Application Priority Data

Sep. 26, 1997 (DE) ........................................ 197 42 492

(51) Int. Cl.$^7$ .................... C07D 209/54; C07D 307/94; A01N 43/12; A01N 43/38
(52) U.S. Cl. ...................... 514/409; 514/462; 514/438; 548/408; 549/62; 549/284; 504/284
(58) Field of Search ............................ 548/408; 549/62, 549/265, 284; 504/284; 514/409, 438, 462

(56) References Cited

U.S. PATENT DOCUMENTS

| | | | |
|---|---|---|---|
| 5,094,681 A | 3/1992 | Krämer et al. ................ 71/88 |
| 5,207,817 A | 5/1993 | Krämer et al. ............... 504/299 |
| 5,258,527 A | 11/1993 | Krauskoph et al. .......... 548/543 |
| 5,262,383 A | 11/1993 | Fischer et al. ............... 504/195 |
| 5,504,057 A | 4/1996 | Fischer et al. ............... 504/283 |
| 5,567,671 A | 10/1996 | Fischer et al. ............... 504/283 |
| 5,589,469 A | 12/1996 | Fischer et al. ................ 514/91 |

(List continued on next page.)

FOREIGN PATENT DOCUMENTS

| WO | WO 95/20572 | 8/1995 |
| WO | WO 96/25395 | 8/1996 |
| WO | WO 96/35664 | 11/1996 |
| WO | WO 97/01535 | 1/1997 |
| WO | WO 97/36868 | 10/1997 |
| WO | WO 98/05638 | 2/1998 |

OTHER PUBLICATIONS

J. Chem. Soc., Perkin Trans. I (month unavailable), 1985, pp. 1567–1576, Alexander C. Campbell, et al, "Synthesis of (E)- and (Z)- Pulvinones".

Primary Examiner—Richard L. Raymond
Assistant Examiner—Venkataraman Balasubramanian
(74) Attorney, Agent, or Firm—Richard E. L. Henderson; Raymond J. Harmuth; Joseph C. Gil

(57) ABSTRACT

The invention relates to novel spirocyclic phenylketoenols of the formula

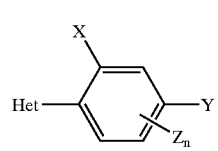

(I)

in which

Het represents one of the groups

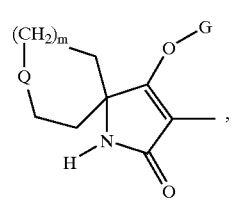

(1)

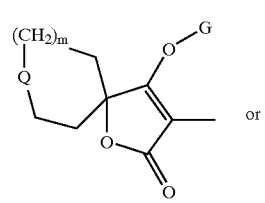

(2)

or

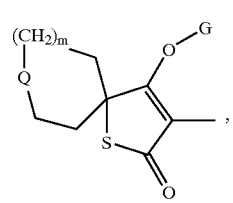

(3)

in which
Q represents

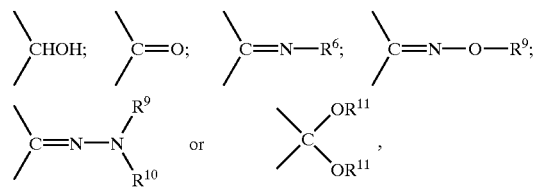

and X, Y, Z, m, n, $R^6$, $R^9$, $R^{10}$ and $R^{11}$ are each as defined in the description, to a plurality of processes and intermediates for their preparation and to their use as pesticides and herbicides.

14 Claims, No Drawings

U.S. PATENT DOCUMENTS

| | | | |
|---|---|---|---|
| 5,602,078 A | 2/1997 | Fischer et al. | 504/283 |
| 5,610,122 A | 3/1997 | Fischer et al. | 504/251 |
| 5,616,536 A | 4/1997 | Fischer et al. | 504/225 |
| 5,622,917 A | 4/1997 | Fischer et al. | 504/283 |
| 5,830,825 A | 11/1998 | Fischer et al. | 504/130 |
| 5,830,826 A | 11/1998 | Fischer et al. | 504/195 |
| 5,981,567 A | 11/1999 | Fischer et al. | 514/409 |
| 5,994,274 A | 11/1999 | Fischer et al. | 504/282 |
| 6,051,723 A | 4/2000 | Fischer et al. | 549/420 |

UTILIZING SPIROCYCLIC PHENYL KETO-ENOLS AS PESTICIDES AND HERBICIDES

The invention relates to novel spirocyclic phenylketoenols, to a plurality of processes and intermediates for their preparation and to their use as pesticides and herbicides.

It is already known that certain phenyl-substituted cyclic ketoenols are active as insecticides, acaricides and/or herbicides, for example 1H-arylpyrrolidine-dione derivatives (EP-A-456 063, EP-A-521 334, EP-A-596 298, EP-A-613 884, EP-A-613 885, DE-44 40 594, WO 94/01 997, WO 95/01 358, WO 95/26 954, WO 95/20 572, EP-A-0 668 267, WO 96/25 395, WO 96/35 664, WO 97/01 535 and WO 97/02 243).

Furthermore, it is known that certain substituted $\Delta^3$-dihydrofuran-2-one derivatives have herbicidal properties (cf. DE-A-4 014 420). The synthesis of the tetronic acid derivatives employed as starting materials (such as, for example, 3-(2-methylphenyl)-4-hydroxy-5-(4-fluorophenyl)-$\Delta^3$-dihydrofuran-(2)-one) is also described in DE-A-4 014 420. Compounds of a similar structure are known from the publication Campbell et al., J. Chem. Soc., Perkin Trans. 1, 1985, (8) 1567–76, without any insecticidal and/or acaricidal activity having been mentioned. Furthermore, 3-aryl-$\Delta^3$-dihydrofuranone derivatives having herbicidal, acaricidal and insecticidal properties are known from EP-A-528 156, EP-A 0 647 637, WO 95/26345, WO 96/20 196, WO 96/25 395, WO 96/35 664, WO 97/01 535, WO 97/02 243 and WO 97/36 868.

However, the efficacy and the spectrum of action of these compounds is, in particular at low application rates and concentrations, not always entirely satisfactory. Furthermore, the crop plant safety of these compounds is not always sufficient.

This invention, accordingly, provides novel compounds of the formula (I)

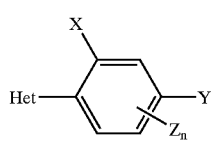

in which,
- X represents halogen, alkyl, alkenyl, alkinyl, alkoxy, alkenyloxy, alkylthio, alkylsulphinyl, alkylsulphonyl, halogenoalkyl, halogenoalkenyl, halogenoalkoxy, halogenoalkenyloxy, nitro, cyano or represents phenyl, phenoxy, phenylthio, benzyloxy or benzylthio, each of which is optionally substituted,
- Y represents hydrogen, halogen, alkyl, alkenyl, alkinyl, alkoxy, alkenyloxy, alkylthio, alkylsulphinyl, alkylsulphonyl, halogenoalkyl, halogenoalkenyl, halogenoalkoxy, halogenoalkenyloxy, nitro or cyano,
- Z represents halogen, alkyl, alkenyl, alkinyl, halogenoalkyl, halogenoalkenyl, alkoxy, alkenyloxy, halogenoalkoxy, halogenoalkenyloxy, nitro or cyano,
- n represents 0, 1, 2 or 3, Het represents one of the groups

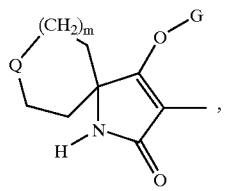

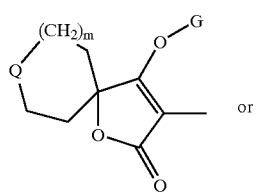

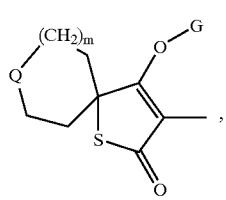

in which
G represents hydrogen (a) or represents one of the groups

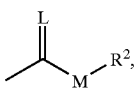

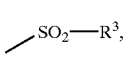

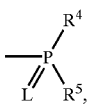

E or

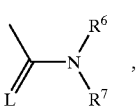

in which
E represents a metal ion equivalent or an ammonium ion,
L represents oxygen or sulphur,
M represents oxygen or sulphur,
$R^1$ represents alkyl, alkenyl, alkoxyalkyl, alkylthioalkyl or polyalkoxyalkyl, each of which is optionally substituted by halogen, represents cycloalkyl which is optionally substituted by halogen, alkyl or alkoxy and which may be interrupted by one or more hetero atoms, or represents phenyl, phenylalkyl, hetaryl, phenoxyalkyl or hetaryloxyalkyl, each of which may optionally be substituted, $R^2$ represents alkyl, alkenyl, alkoxyalkyl or polyalkoxyalkyl, each of which may optionally be substituted by halogen, or represents cycloalkyl, phenyl or benzyl, each of which may optionally be substituted, $R^3$, $R^4$ and $R^5$ independently of one another each represent alkyl, alkoxyl, alkylamino, dialkylamino, alkylthio, alkenylthio or cycloalkylthio, each of which may optionally be substituted by halogen, or represents phenyl, benzyl, phenoxy or phenylthio, each of which may optionally be substituted, $R^6$ and $R^7$ independently of one another represent hydrogen, represent alkyl, cycloalkyl, alkenyl, alkoxy or alkoxyalkyl, each of which may be substituted by halogen, represent phenyl which may optionally be substituted, represent benzyl which may optionally be substituted, or together with the N atom to which they are attached represents an optionally hydrogen- or sulphur-containing ring, Q represents

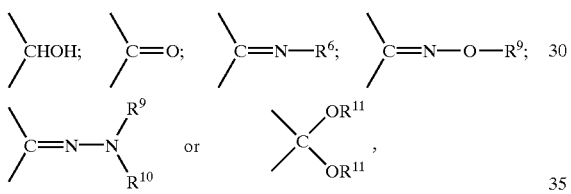

$R^9$ represents hydrogen, represents alkyl, cycloalkyl, phenyl, benzyl or hetaryl, each of which may optionally be substituted, or represents CO—$R^{1'}$; $CO_2$—$R^{2'}$; $SO_2$—$R^{1'}$; $CONH_2$; $CONHR^{11}$ or

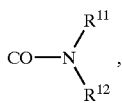

$R^{10}$ represents hydrogen or alkyl,
$R^{11}$ represents alkyl or alkenyl,
$R^{12}$ represents alkyl or alkenyl,
m represents 0, 1 or 2,
$R^{1'}$ independently of $R^1$ has the meanings given above for $R^1$ and
$R^{2'}$ independently of $R^2$ has the meanings given above for $R^2$.

Depending inter alia on the nature of the substituents, the compounds of the formula (I) can be present as geometric and/or optical isomers or isomer mixtures of varying composition, which can be separated, if appropriate, in a customary manner. The present invention provides both the pure isomers and the isomer mixtures, their preparation and use and compositions comprising them. For simplicity, however, reference is always made below to compounds of the formula (I), although this means both the pure compounds and, where appropriate, also mixtures with different contents of isomeric compounds.

Incorporating the meanings (1) to (3) of the group Het, the following main structures (I-1) to (I-3) result:

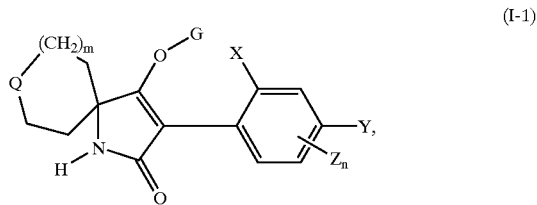

(I-1)

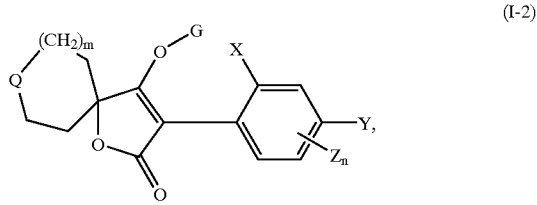

(I-2)

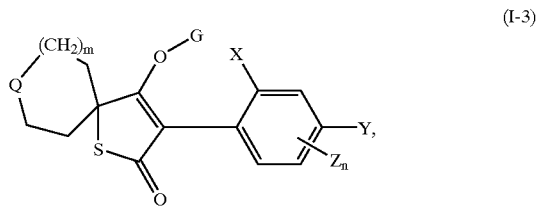

(I-3)

in which

Q, G, X, Y, Z, n and m are each as defined above.

Incorporating the various meanings (a), (b), (c), (d), (e), (f) and (g) of the group G, the following main structures (I-1-a) to (I-1-g), result if Het represents the group (I)

(I-1-a):

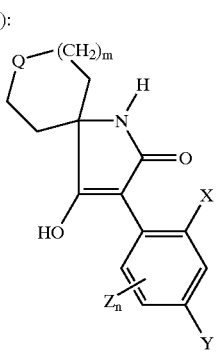

(I-1-b):

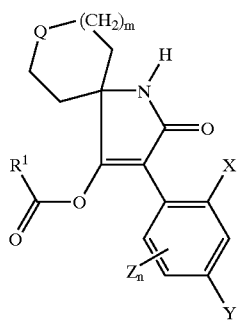

(I-1-c):
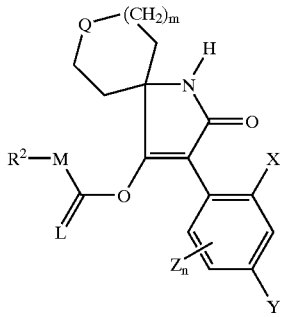
(I-1-d):
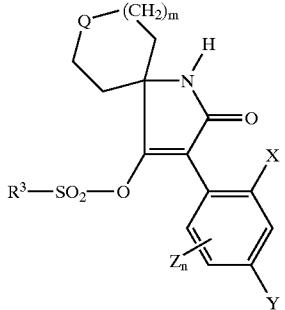
(I-1-e):
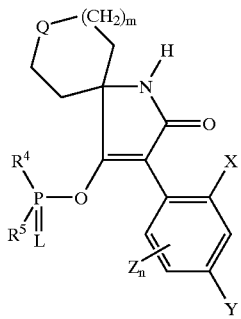
(I-1-f):
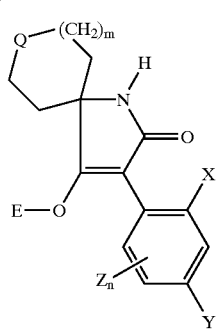
(I-1-g):
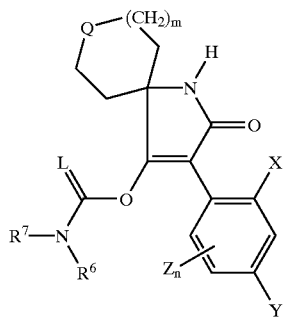
in which
E, L, M, Q, X, Y, Z, n, m, $R^1$, $R^2$, $R^3$, $R^4$, $R^5$, $R^6$ and $R^7$ are each as defined above.
Incorporating the various meanings (a), (b), (c), (d), (e), (f) and (g) of the group G, the following main structures (I-2-a) to (I-2-g), result if Het represents the group (2)
(I-2-a):
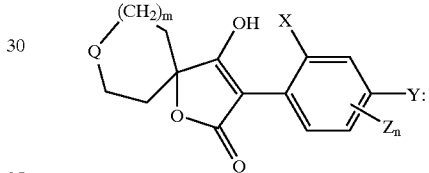
(I-2-b):
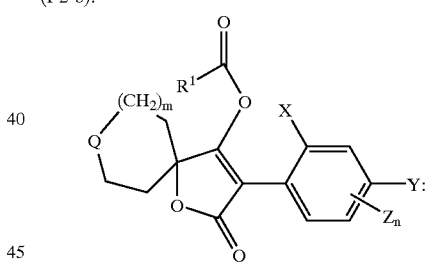
(I-2-c):
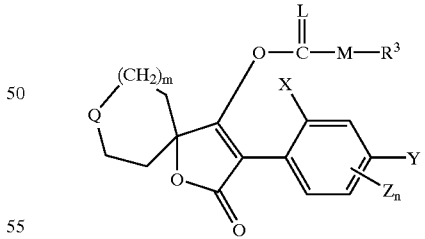
(I-2-d):
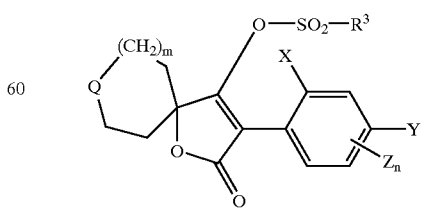

(I-2-e):

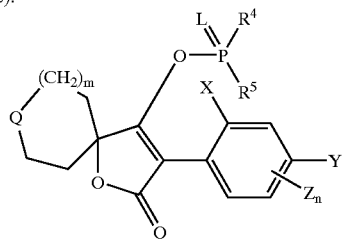

(I-2-f):

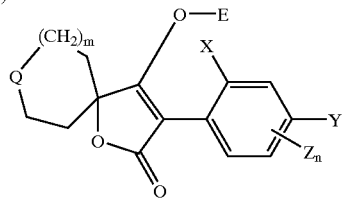

(I-2-g):

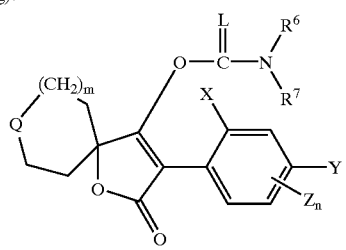

in which

E, L, M, Q, X, Y, Z, n, m, $R^1$, $R^2$, $R^3$, $R^4$, $R^5$, $R^6$ and $R^7$ are each as defined above.

Incorporating the various meanings (a), (b), (c), (d), (e), (f) and (g) of the group G, the following main structures (I-3-a) to (I-3-g), result if Het represents the group (3)

(I-3-a):

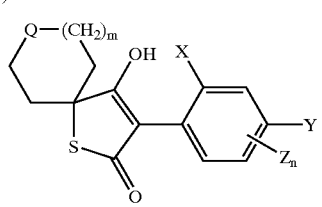

(I-3-b):

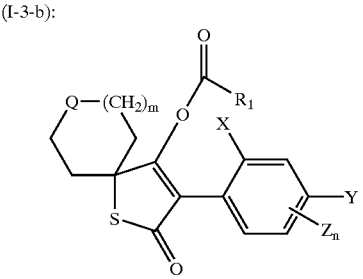

(I-3-c):

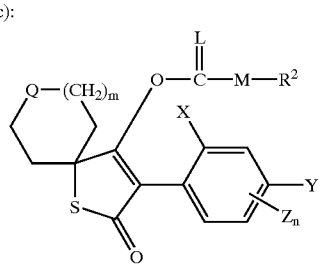

(I-3-d):

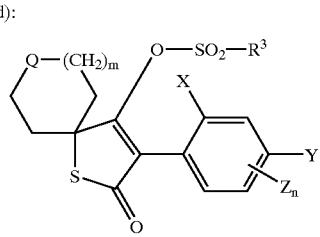

(I-3-e):

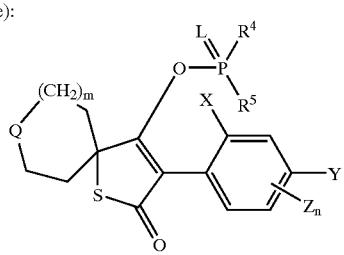

(I-3-f):

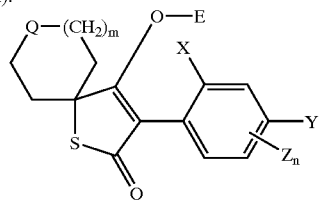

(I-3-g):

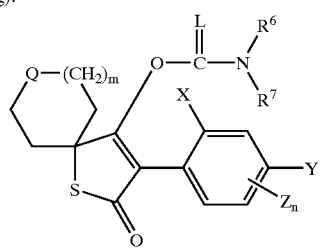

in which

E, L, M, Q, X, Y, Z, n, m, $R^1$, $R^2$, $R^3$, $R^4$, $R^5$, $R^6$ and $R^7$ are each as defined above.

Furthermore, it has been found that the novel compounds of the formula (I) are obtained by one of the processes described below:

(A) Substituted 3-phenylpyrrolidine-2,4-diones or enols thereof of the formula (I-1-a)

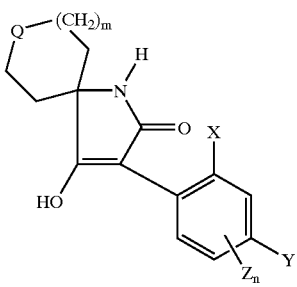
(I-1-a)

in which
Q, X, Y, Z, m and n are each as defined above,
are obtained when
N-acylamino acid esters of the formula (II)

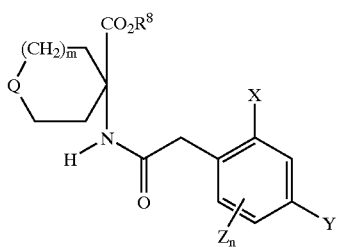
(II)

in which
Q, X, Y, Z, m and n are each as defined above,
and
$R^8$ represents alkyl (preferably $C_1$–$C_6$-alkyl),
are intramolecularly condensed in the presence of a diluent and in the presence of a base.

(B) Furthermore, it has been found that substituted 3-phenyl-4-hydroxy-$\Delta^3$-dihydrofuranone derivatives of the formula (I-2-a)

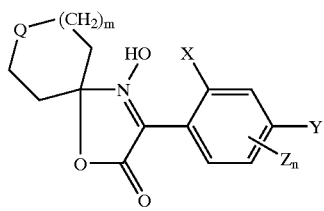
(I-2-a)

in which
Q, X, Y, Z, m and n are each as defined above,
are obtained when
carboxylic esters of the formula (III)

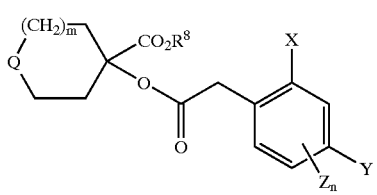
(III)

in which
Q, X, Y, Z, m, n and $R^8$ are each as defined above,
are intramolecularly condensed in the presence of a diluent and in the presence of a base.

(C) Furthermore, it has been found that substituted 3-phenyl-4-hydroxy-$\Delta^3$-dihydrothiophenone derivatives of the formula (I-3-a)

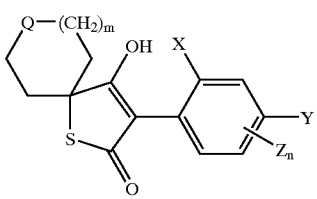
(I-3-a)

in which
Q, X, Y, Z, m and n are each as defined above,
are obtained when
β-ketocarboxylic esters of the formula (IV)

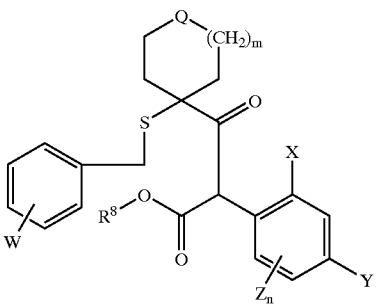
(IV)

in which
Q, X, Y, Z, m, n and $R^8$ are each as defined above and
W represents hydrogen, halogen, alkyl (preferably $C_1$–$C_6$-alkyl) or alkoxy (preferably $C_1$–$C_8$-alkoxy),
are intramolecularly cyclized in the presence of a diluent and in the presence of an acid.

Furthermore, it has been found that the compounds of the formulae (I-1-b) to (I-3-b), depicted above in which
(D) Q, X, Y, Z, m, n and $R^1$ are each as defined above are obtained when compounds of the formulae (I-1-a) to (I-3-a) depicted above in which Q, X, Y, Z, m and n are each as defined above are in each case reacted
α) with acyl chlorides of the formula (V)

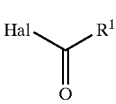
(V)

in which
$R^1$ is as defined above and
Hal represents halogen (in particular chlorine or bromine)
or
β) with carboxylic anhydrides of the formula (VI)

$R^1$—CO—O—CO—$R^1$ (VI)

in which

R¹ is as defined above, if appropriate in the presence of a diluent and if appropriate in the presence of an acid binder;

(E) that the compounds of the formulae (I-1-c) to (I-3-c) depicted above in which Q, R², M, X, Y, Z, m and n are each as defined above and L represents oxygen are obtained when compounds of the formulae (I-1-a) to (I-3-a) depicted above in which Q, X, Y, Z, m and n are each as defined above are in each case reacted with chloroformic acid esters or chloroformic acid thiol esters of the formula (VII)

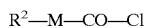

(VII)

in which

R² and M are each as defined above, if appropriate in the presence of a diluent and if appropriate in the presence of an acid binder;

(F) that compounds of the formulae (I-1-c) to (I-3-c) depicted above in which Q, R², M, X, Y, Z, m and n are each as defined above and L represents sulphur are obtained when compounds of the formulae (I-1-a) to (I-3-a) depicted above in which Q, X, Y, Z, m and n are each as defined above are in each case reacted with chloromonothioformic acid esters or chlorodithioformic acid esters of the formula (VIII)

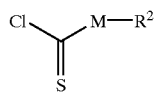

(VIII)

in which

M and R² are each as defined above, if appropriate in the presence of a diluent and if appropriate in the presence of an acid binder, (G) that compounds of the formulae (I-1-d) to (I-3-d) depicted above in which Q, R³, X, Y, Z, m and n are each as defined above are obtained when compounds of the formulae (I-1-a) to (I-3-a), depicted above in which Q, X, Y, Z, m and n are each as defined above are in each case reacted with sulphonyl chlorides of the formula (IX)

(IX)

in which

R³ is as defined above, if appropriate in the presence of a diluent and if appropriate in the presence of an acid binder, (H) that compounds of the formulae (I-1-e) to (I-3-e) depicted above in which Q, L, R⁴, R⁵, X, Y, Z, m and n are each as defined above are obtained when compounds of the formulae (I-1-a) to (I-3-a) depicted above in which Q, X, Y, Z, m and n are each as defined above are in each case reacted with phosphorus compounds of the formula (X)

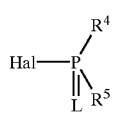

(X)

in which

L, R⁴ and R⁵ are each as defined above and

Hal represents halogen (in particular chlorine or bromine), if appropriate in the presence of a diluent and if appropriate in the presence of an acid binder, (I) that compounds of the formulae (I-1-f) to (I-3-f) depicted above in which Q, E, X, Y, Z, m and n are each as defined above are obtained when compounds of the formulae (I-1-a) to (I-3-a) depicted above in which Q, X, Y, Z, m and n are each as defined above are in each case reacted with metal compounds or amines of the formula (XI) or (XII)

(XI)

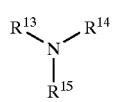

(XII)

in which

Me represents a mono- or divalent metal (preferably an alkali metal or alkaline earth metal such as lithium, sodium, potassium, magnesium or calcium), t represents 1 or 2 and R¹³, R¹⁴, R¹⁵ independently of one another each represent hydrogen or alkyl (preferably C₁–C₈-alkyl), if appropriate in the presence of a diluent, (J) that compounds of the formulae (I-1-g) to (I-3-g) depicted above in which Q, L, R⁶, R⁷, X, Y, Z, m and n are each as defined above are obtained with compounds of the formulae (I-1-a) to (I-3-a) depicted above in which Q, X, Y, Z, m and n are each as defined above are in each case reacted α) with isocyanates or isothiocyanates of the formula (XIII)

(XIII)

in which

R⁶ and L are each as defined above, if appropriate in the presence of a diluent and if appropriate in the presence of a catalyst or β) with carbamoyl chlorides or thiocarbamoyl chlorides of the formula (XIV)

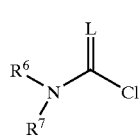

(XIV)

in which

L, R⁶ and R⁷ are each as defined above, if appropriate in the presence of a diluent and if appropriate in the presence of an acid binder.

The compounds of the formulae (I-1-a), (I-2-a) and (I-3-a) are thus important intermediates for preparing the compounds of the formulae (I-1), (I-2) and (I-3), according to the invention in which G in each case represents one of the groups b), c), d), e), f) or g).

Furthermore, it has been found that the novel compounds of the formula (I) have very good activity as pesticides, preferably as insecticides and acaracides, and as herbicides.

The formula (I) provides a general definition of the compounds according to the invention. Preferred substituents or ranges of the radicals listed in the formulae hereinabove and hereinbelow are illustrated below:

X preferably represents halogen, $C_1$–$C_6$-alkyl, $C_2$–$C_6$-alkenyl, $C_2$–$C_6$-alkinyl, $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkyl, $C_2$–$C_6$-halogenoalkenyl, $C_1$–$C_6$-halogenoalkoxy, $C_3$–$C_6$-halogenoalkenyloxy, nitro, cyano or represents phenyl, phenoxy, phenylthio, benzyloxy or benzylthio, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano.

Y preferably represents hydrogen, halogen, $C_1$–$C_6$-alkyl, $C_2$–$C_6$-alkenyl, $C_2$–$C_6$-alkinyl, $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkyl, $C_2$–$C_6$-halogenoalkenyl, $C_1$–$C_6$-halogenoalkoxy, $C_3$–$C_6$-halogenoalkenyloxy, nitro or cyano.

Z preferably represents halogen, $C_1$–$C_6$-alkyl, $C_2$–$C_6$-alkenyl, $C_2$–$C_6$-alkinyl, $C_1$–$C_6$-halogenoalkyl, $C_2$–$C_6$-halogenoalkenyl, $C_1$–$C_6$-alkoxy, $C_3$–$C_6$-alkenyloxy, $C_1$–$C_6$-halogenoalkoxy, $C_3$–$C_6$-halogenoalkenyloxy, nitro or cyano.

n preferably represents 0, 1, 2 or 3.

Het preferably represents one of the groups

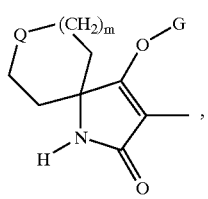

(1)

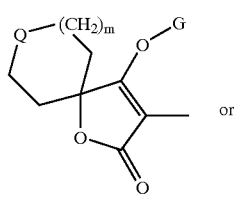

(2)

or

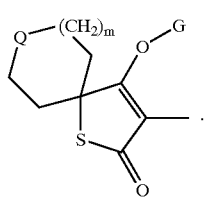

(3)

G preferably represents hydrogen (a) or represents one of the groups

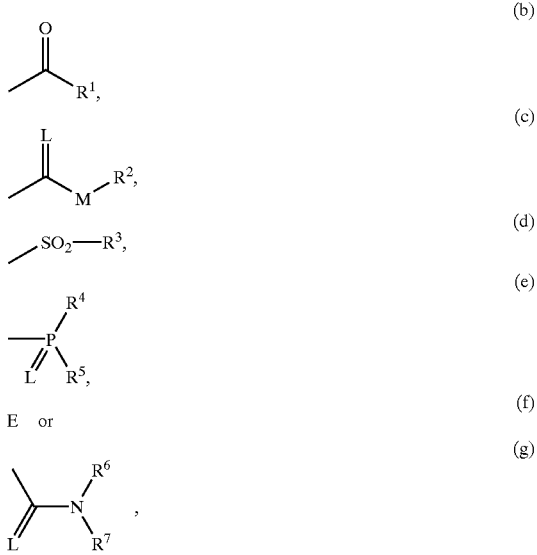

in which

E represents a metal ion equivalent or an ammonium ion,

L represents oxygen or sulphur and

M represents oxygen or sulphur.

$R^1$ preferably represents $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl, each of which may optionally be substituted with halogen, represents $C_3$–$C_8$-cycloalkyl which may optionally be substituted by halogen, $C_1$–$C_6$-alkyl or $C_1$–$C_6$-alkoxy and in which optionally one or more (in particular at most two) not directly adjacent methylene groups may be replaced by oxygen and/or sulphur, represents phenyl which is optionally substituted by halogen, cyano, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio or $C_1$–$C_6$-alkylsulphonyl, represents phenyl-$C_1$–$C_6$-alkyl, which is optionally substituted by halogen, nitro, cyano, $C_1$–$C_6$-alkyl, $C_1$–$C_6$-alkoxy, $C_1$–$C_6$-halogenoalkyl or $C_1$–$C_6$-halogenoalkoxy, represents 5- or 6-membered hetaryl (for example pyrazolyl, thiazolyl, pyridyl, pyrimidyl, furanyl or thienyl) which is optionally substituted by halogen or $C_1$–$C_6$-alkyl, represents phenoxy-$C_1$–$C_6$-alkyl which is optionally substituted by halogen or $C_1$–$C_6$-alkyl or represents 5- or 6-membered hetaryloxy-$C_1$–$C_6$-alkyl which is optionally substituted by halogen, amino or $C_1$–$C_6$-alkyl (for example pyridyloxy-$C_1$–$C_6$-alkyl, pyrimidyl-$C_1$–$C_6$-alkyl or thiazolyloxy-$C_1$–$C_6$-alkyl)

$R^2$ preferably represents $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, each of which is optionally substituted by halogen, represents $C_3$–$C_8$-cycloalkyl which is optionally substituted by halogen, $C_1$–$C_6$-alkyl or $C_1$–$C_6$-alkoxy or represents phenyl or benzyl, each of which is optionally substituted by halogen, cyano, nitro, $C_1$–$C_6$-alkyl, $C_1$–$C_6$-alkoxy, $C_1$–$C_6$-halogenoalkyl or $C_1$–$C_6$-halogenoalkoxy.

$R^3$ preferably represents $C_1$–$C_8$-alkyl which is optionally substituted by halogen or represents phenyl or benzyl, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

$R^4$ and $R^5$ independently of one another each preferably represent $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio, $C_2$–$C_8$-alkenylthio, $C_3$–$C_7$-cycloalkylthio, each of which is optionally substituted by halogen, or represent phenyl, phenoxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl.

$R^6$ and $R^7$ independently of one another each preferably represent hydrogen, represent $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_1$–$C_8$-alkyl, each of which is optionally substituted by halogen, represent phenyl which is optionally substituted by halogen, $C_1$–$C_8$-halogenoalkyl, $C_1$–$C_8$-alkyl or $C_1$–$C_8$-alkoxy, represent benzyl which is optionally substituted by halogen, $C_1$–$C_8$-alkyl, $C_1$–$C_8$-halogenoalkyl or $C_1$–$C_8$-alkoxy or together represent a $C_3$–$C_6$-alkylene radical in which optionally one methylene group which is not directly adjacent to the nitrogen atom is replaced by oxygen or sulphur.

Q preferably represents

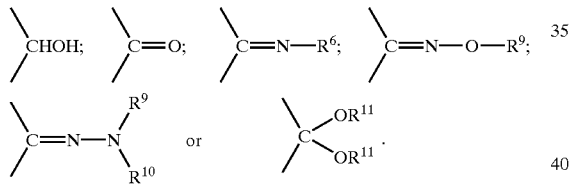

$R^9$ preferably represents hydrogen, represents $C_1$–$C_8$-alkyl which is optionally substituted by halogen, represents $C_3$–$C_8$-cycloalkyl which is optionally substituted by halogen, $C_1$–$C_4$-alkyl or $C_1$–$C_4$-alkoxy or represents phenyl, benzyl or hetaryl (for example pyridyl, pyrimidyl or thiazolyl), each of which is optionally substituted by halogen, $C_1$–$C_6$-alkyl, $C_1$–$C_4$-alkoxy, $C_1$–$C_4$-halogenoalkyl, $C_1$–$C_4$-halogenoalkoxy, nitro or cyano, or represents CO—$R^{1'}$, $CO_2R^{2'}$, $SO_2R^{1'}$, $CONH_2$, $CONHR^{11}$ or

$R^{10}$ preferably represents hydrogen or $C_1$–$C_8$-alkyl.
$R^{11}$ and $R^{12}$ are identical or different and each represents $C_1$–$C_6$-alkyl or $C_3$–$C_6$-alkenyl.
m preferably represents 0 or 1.
$R^{1'}$ independently of $R^1$ preferably has the meanings given above as being preferred for $R^1$.
$R^{2'}$ independently of $R^2$ preferably has the meanings given above as being preferred for $R^2$.

X particularly preferably represents fluorine, chlorine, bromine, $C_1$–$C_4$-alkyl, $C_1$–$C_4$-alkoxy, $C_1$–$C_4$-halogenoalkyl, $C_1$–$C_4$-halogenoalkoxy, nitro or cyano.

Y particularly preferably represents hydrogen, fluorine, chlorine, bromine, $C_1$–$C_4$-alkyl, $C_1$–$C_4$-alkoxy, $C_1$–$C_4$-halogenoalkyl, $C_1$–$C_4$-halogenoalkoxy, nitro or cyano.

Z particularly preferably represents fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, nitro or cyano.

n particularly preferably represents 0, 1 or 2.

Het particularly preferably represents one of the groups

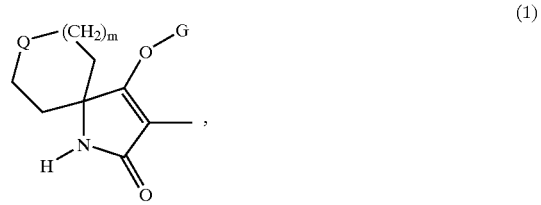
(1)

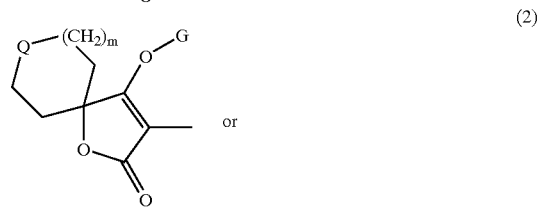
or (2)

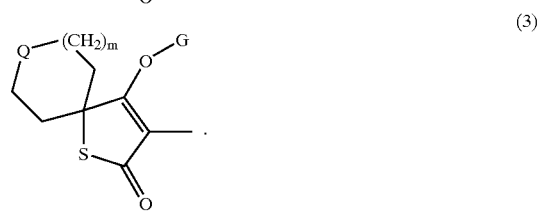
(3)

G particularly preferably represents hydrogen (a) or represents one of the groups

(b)

(c)

(d)

(e)

(f)

E or
(g)

in particular (a), (b) or (c),
in which
E represents a metal ion equivalent or an ammonium ion,
L represents oxygen or sulphur and M represents oxygen or sulphur.

$R^1$ particularly preferably represents $C_1$–$C_{16}$-alkyl, $C_2$–$C_{16}$-alkenyl, $C_1$–$C_6$-alkoxy-$C_1$–$C_6$-alkyl or $C_1$–$C_6$-alkylthio-$C_1$–$C_6$-alkyl, each of which is optionally substituted by fluorine or chlorine, or represents $C_3$–$C_7$-cycloalkyl which is optionally substituted by fluorine, chlorine, $C_1$–$C_5$-alkyl or $C_1$–$C_5$-alkoxy, represents phenyl which is optionally substituted by fluorine, chlorine, bromine, cyano, nitro, $C_1$–$C_4$-alkyl, $C_1$–$C_4$-alkoxy, $C_1$–$C_3$-halogenoalkyl or $C_1$–$C_3$-halogenoalkoxy, represents phenyl-$C_1$–$C_4$-alkyl which is optionally substituted by fluorine, chlorine, bromine, $C_1$–$C_4$-alkyl, $C_1$–$C_4$-alkoxy, $C_1$–$C_3$-halogenoalkyl or $C_1$–$C_3$-halogenoalkoxy or represents pyrazolyl, thiazolyl, pyridyl, pyrimidyl, furanyl or thienyl, each of which is optionally substituted by fluorine, chlorine, bromine or $C_1$–$C_4$-alkyl.

$R^2$ particularly preferably represents $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, each of which is optionally substituted by fluorine, represents $C_3$–$C_7$-cycloalkyl which is optionally substituted by fluorine, chlorine, $C_1$–$C_4$-alkyl or $C_1$–$C_4$-alkoxy or represents phenyl or benzyl, each of which is optionally substituted by fluorine, chlorine, bromine, cyano, nitro, $C_1$–$C_4$-alkyl, $C_1$–$C_3$-alkoxy, $C_1$–$C_3$-halogenoalkyl or $C_1$–$C_3$-halogenoalkoxy.

$R^3$ particularly preferably represents $C_1$–$C_6$-alkyl which is optionally substituted by fluorine or chlorine or represents phenyl or benzyl, each of which is optionally substituted by fluorine, chlorine, bromine, $C_1$–$C_5$-alkyl, $C_1$–$C_5$-alkoxy, $C_1$–$C_3$-halogenoalkyl, $C_1$–$C_3$-halogenoalkoxy, cyano and nitro.

$R^4$ and $R^5$ independently of one another each particularly preferably represent $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio, $C_3$–$C_4$-alkenylthio or $C_3$–$C_6$-cycloalkylthio, each of which is optionally substituted by fluorine or chlorine, or represents phenyl, phenoxy or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl.

$R^6$ and $R^7$ independently of one another each particularly preferably represent hydrogen, represent $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_1$–$C_6$-alkyl, each of which is optionally substituted by halogen (in particular fluorine or chlorine), represent phenyl which is optionally substituted by halogen, $C_1$–$C_5$-halogenoalkyl, $C_1$–$C_5$-alkyl or $C_1$–$C_5$-alkoxy, represent benzyl which is optionally substituted by halogen, $C_1$–$C_5$-alkyl, $C_1$–$C_5$-halogenoalkyl or $C_1$–$C_5$-alkoxy or together represent a $C_3$–$C_6$-alkylene radical in which optionally one methylene group which is not directly adjacent to the nitrogen atom is replaced by oxygen or sulphur.

Q particularly preferably represents

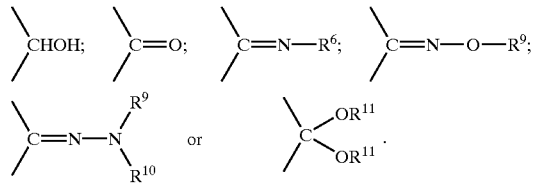

$R^9$ particularly preferably represents hydrogen, represents $C_1$–$C_6$-alkyl, which is optionally substituted by fluorine or chlorine, represents $C_3$–$C_7$-cycloalkyl or represents phenyl or benzyl, each of which is optionally substituted by fluorine, chlorine, bromine, $C_1$–$C_5$-alkyl, $C_1$–$C_4$-alkoxy, $C_1$–$C_2$-halogenoalkyl, $C_1$–$C_2$-halogenoalkoxy, nitro or cyano, represents pyrimidiyl or thiazolyl or represents CO—$R^{1'}$, $CO_2R^{2'}$, $SO_2R^{1'}$, $CONH_2$, $CONHR^{11}$ or

$R^{10}$ particularly preferably represents hydrogen or $C_1$–$C_6$-alkyl.

$R^{11}$ and $R^{12}$ are identical or different and each particularly preferably represents $C_1$–$C_4$-alkyl.

m particularly preferably represents 1.

$R^{1'}$ independently of $R^1$ particularly preferably has the meanings given above as being particularly preferred for $R^1$.

$R^{2'}$ independently of $R^2$ particularly preferably has the meanings given above as being particularly preferred for $R^2$.

X very particularly preferably represents fluorine, chlorine, bromine, methyl, ethyl, n-propyl, iso-propyl, methoxy, ethoxy, n-propoxy, iso-propoxy, trifluoromethyl, difluoromethoxy, trifluoromethoxy, nitro or cyano.

Y very particularly preferably represents hydrogen, fluorine, chlorine, bromine, methyl, ethyl, n-propyl, i-propyl, n-butyl, i-butyl, tert-butyl, methoxy, ethoxy, n-propoxy, iso-propoxy, trifluoromethyl, difluoromethoxy, trifluoromethoxy, nitro or cyano.

Z very particularly preferably represents fluorine, chlorine, bromine, methyl, ethyl, n-propyl, i-propyl, n-butyl, i-butyl, tert-butyl, methoxy, ethoxy, n-propoxy, iso-propoxy, difluoromethoxy, trifluoromethoxy, nitro or cyano.

n very particularly preferably represents 0, 1 or 2, especially 0 or 1.

Het very particularly preferably represents one of the groups

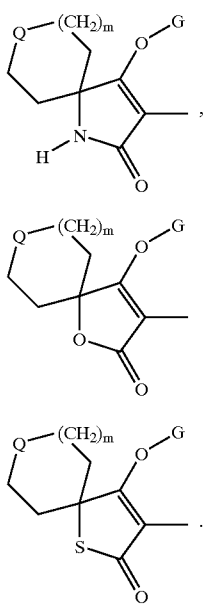

(1)

(2)

(3)

G very particularly preferably represents hydrogen (a) or represents one of the groups

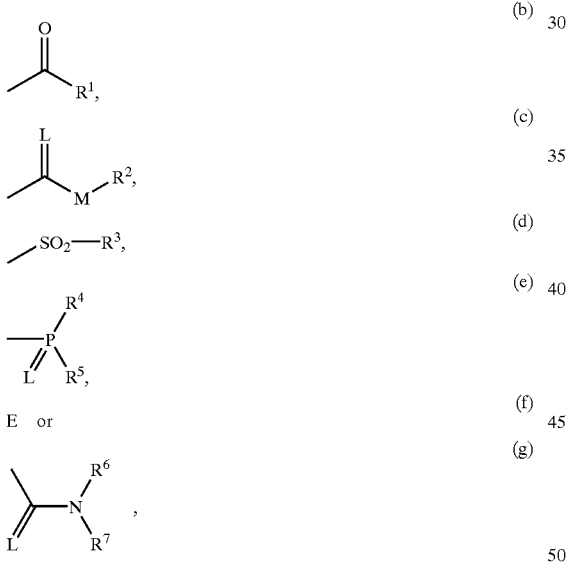

in particular (b) or (c),
in which
E represents a metal ion equivalent or an ammonium ion,
L represents oxygen or sulphur and
M represents oxygen or sulphur.

$R^1$ very particularly preferably represents $C_1$–$C_{14}$-alkyl, $C_2$–$C_{14}$-alkenyl, $C_1$–$C_4$-alkoxy-$C_1$–$C_6$-alkyl or $C_1$–$C_4$-alkylthio-$C_1$–$C_6$-alkyl, each of which is optionally substituted by fluorine or chlorine, or represents $C_3$–$C_6$-cycloalkyl, which is optionally substituted by methyl, ethyl, tert-butyl or methoxy, represents phenyl which is optionally substituted by fluorine, chlorine, bromine, cyano, nitro, methyl, methoxy, trifluoromethyl or trifluoromethoxy, represents benzyl which is optionally substituted by fluorine, chlorine, bromine, methyl, methoxy, trifluoromethyl or trifluoromethoxy or represents furanyl, thienyl or pyridyl, each of which is optionally substituted by fluorine, chlorine, bromine or methyl.

$R^2$ very particularly preferably represents $C_1$–$C_{14}$-alkyl, $C_2$–$C_{14}$-alkenyl or $C_1$–$C_4$-alkoxy-$C_2$–$C_6$-alkyl, represents $C_3$–$C_6$-cycloalkyl which is optionally substituted by methyl or methoxy or represents phenyl or benzyl, each of which is optionally substituted by fluorine, chlorine, bromine, cyano, nitro, methyl, methoxy, trifluoromethyl or trifluoromethoxy.

$R^3$ very particularly preferably represents methyl, ethyl, n-propyl, isopropyl, each of which is optionally substituted by fluorine or chlorine, or represents phenyl or benzyl, each of which is optionally substituted by fluorine, chlorine, bromine, methyl, ethyl, n-propyl, iso-propyl, tert-butyl, methoxy, ethoxy, isopropoxy, tert-butoxy, trifluoromethyl, trifluoromethoxy, cyano or nitro.

$R^4$ and $R^5$ independently of one another each very particularly preferably represent $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio, each of which is optionally substituted by fluorine or chlorine, or represent phenyl, phenoxy or phenylthio, each of which is optionally substituted by fluorine, chlorine, bromine, nitro, cyano, $C_1$–$C_2$-alkoxy, $C_1$–$C_2$-fluoroalkoxy, $C_1$–$C_2$-alkylthio, $C_1$–$C_2$-fluoroalkylthio or $C_1$–$C_3$-alkyl.

$R^6$ and $R^7$ independently of one another each very particularly preferably represent hydrogen, represent $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_1$–$C_4$-alkyl, each of which is optionally substituted by fluorine or chlorine, represent phenyl which is optionally substituted by fluorine, chlorine, bromine, trifluoromethyl, methyl or methoxy, represent benzyl which is optionally substituted by fluorine, chlorine, bromine, $C_1$–$C_4$-alkyl, $C_1$–$C_4$-halogenoalkyl or $C_1$–$C_4$-alkoxy or together represent a $C_5$–$C_6$-alkylene radical in which optionally one methylene group which is not directly adjacent to the nitrogen atom may be replaced by oxygen or sulphur.

Q very particularly preferably represents

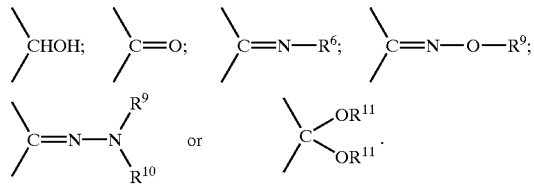

$R^9$ very particularly preferably represents hydrogen, represents $C_1$–$C_4$-alkyl, represents $C_3$–$C_6$-cycloalkyl or represents phenyl or benzyl, each of which is optionally substituted by fluorine, chlorine, bromine, methyl, ethyl, n-propyl, iso-propyl, tert-butyl, methoxy, trifluoromethyl, trifluoromethoxy, nitro or cyano, or represents CO—$R^{1'}$, $CO_2R^{2'}$, $SO_2R^{1'}$, $CONH_2$, $CONHR^{11}$ or

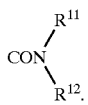

R[10] very particularly preferably represents hydrogen or methyl.

R[11] and R[12] are identical or different and each very particularly preferably represents methyl or ethyl.

m very particularly preferably represents 1.

R[1'] independently of R[1] very particularly preferably has the meanings given above as being very particularly preferred for R[1].

R[2'] independently of R[2] very particularly preferable has the meanings given above as being very particularly preferred for R[2].

The abovementioned general or preferred radical definitions or illustrations can be combined with each other as desired, i.e. including combinations between the ranges and preferred ranges in question. They apply both to the end products and to the precursors and intermediates correspondingly.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Saturated or unsaturated hydrocarbon radicals such as alkyl or alkenyl, also in combination with hetero atoms, such as, for example, in alkoxy, can in each case be straight-chain or branched, as far as this is possible.

Optionally substituted radicals may be mono- or polysubstituted, and in the case of polysubstitution the substituents may be identical or different.

In addition to the compounds mentioned in the Preparation Examples, the following compounds of the formula (I-1-a) may be specifically mentioned:

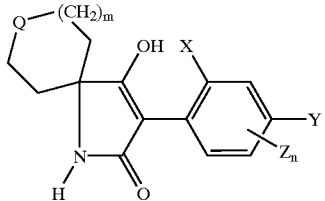

TABLE 1 m = 1

$Q = \backslash CH-OH /$

| X | Y | $Z_n$ | X | Y | $Z_n$ |
|---|---|---|---|---|---|
| $CH_3$ | H | H | $CH_3$ | Br | 6-Cl |
| $CH_3$ | $CH_3$ | H | $CH_3$ | Cl | 6-Br |

TABLE 1-continued m = 1

$Q = \backslash CH-OH /$

| X | Y | $Z_n$ | X | Y | $Z_n$ |
|---|---|---|---|---|---|
| $CH_3$ | H | 5-$CH_3$ | Br | $CH_3$ | 6-Cl |
| $CH_3$ | H | 6-$CH_3$ | $CH_3$ | $CH_3$ | 6-CN |
| $CH_3$ | $CH_3$ | 5-$CH_3$ | $CH_3$ | CN | 6-$CH_3$ |
| $CH_3$ | $CH_3$ | 6-$CH_3$ | $CH_3$ | $CH_3$ | 6-$OCH_3$ |
| $CH_3$ | $CH_3$ | 3,5-$(CH_3)_2$ | $CH_3$ | $OCH_3$ | 6-$CH_3$ |
| $CH_3$ | $CH_3$ | 3,6-$(CH_3)_2$ | Cl | Cl | 5-Cl |
| $CH_3$ | Cl | H | $CH_3$ | Cl | 5-$CH_3$ |
| Cl | $CH_3$ | H | Br | $CH_3$ | 5-Cl |
| Cl | H | 6-F | Br | $CH_3$ | 5-$CH_3$ |
| $CH_3$ | H | 6-Cl | $CH_3$ | Br | 5-Cl |
| Cl | H | 6-Cl | Cl | Cl | 5-$CH_3$ |
| $CH_3$ | Cl | 6-Cl | $CH_3$ | Br | 5-$CH_3$ |
| $CH_3$ | Br | 5-Br | Cl | $CH_3$ | 5-Cl |
| Cl | $CH_3$ | 6-Cl | $CH_3$ | $CH_3$ | 5-Br |
| Br | $CH_3$ | 6-Br | $CH_3$ | H | 3-Cl, 6-$CH_3$ |
| $CH_3$ | Cl | 6-$CH_3$ | $CH_3$ | H | 3-Br, 6-$CH_3$ |
| $CH_3$ | $CH_3$ | 6-Cl | Cl | $CF_3$ | 6-Cl |
| $CH_3$ | Br | 6-$CH_3$ | | | |
| $CH_3$ | $CH_3$ | 6-Br | | | |

Tables 2 to 8

Compounds of the formula (I-1-a)

TABLE 2

X, Y and $Z_n$ as stated in Table 1 m = 1

$Q = \backslash C=O /$

TABLE 3

X, Y and $Z_n$ as stated in Table 1 m = 1

$Q = \backslash C=N-OCH_3 /$

TABLE 4

X, Y and $Z_n$ as stated in Table 1 m = 1

$Q = \backslash C=N-OC_2H_5 /$

TABLE 5

X, Y and $Z_n$ as stated in Table 1 m = 1

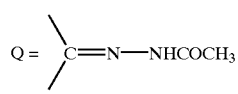

TABLE 6

X, Y and $Z_n$ as stated in Table 1 m = 1

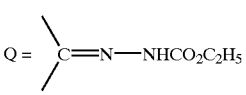

TABLE 7

X, Y and $Z_n$ as stated in Table 1 m = 1

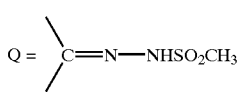

TABLE 8

X, Y and $Z_n$ as stated in Table 1 m = 1

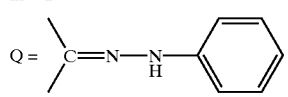

In addition to the compounds mentioned in the Preparation Examples, the following compounds of the formula (I-2-a) may be specifically mentioned:

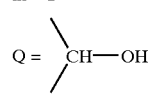

TABLE 9 m = 1

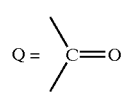

| X | Y | $Z_n$ | X | Y | $Z_n$ |
|---|---|---|---|---|---|
| $CH_3$ | H | H | $CH_3$ | Br | 6-Cl |
| $CH_3$ | $CH_3$ | H | $CH_3$ | Cl | 6-Br |
| $CH_3$ | H | 5-$CH_3$ | Br | $CH_3$ | 6-Cl |

TABLE 9-continued m = 1

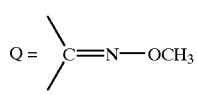

| X | Y | $Z_n$ | X | Y | $Z_n$ |
|---|---|---|---|---|---|
| $CH_3$ | H | 6-$CH_3$ | $CH_3$ | $CH_3$ | 6-CN |
| $CH_3$ | $CH_3$ | 5-$CH_3$ | $CH_3$ | CN | 6-$CH_3$ |
| $CH_3$ | $CH_3$ | 6-$CH_3$ | $CH_3$ | $CH_3$ | 6-$OCH_3$ |
| $CH_3$ | $CH_3$ | 3,5-$(CH_3)_2$ | $CH_3$ | $OCH_3$ | 6-$CH_3$ |
| $CH_3$ | $CH_3$ | 3,6-$(CH_3)_2$ | Cl | Cl | 5-Cl |
| $CH_3$ | Cl | H | $CH_3$ | Cl | 5-$CH_3$ |
| Cl | $CH_3$ | H | Br | $CH_3$ | 5-Cl |
| Cl | H | 6-F | Br | $CH_3$ | 5-$CH_3$ |
| $CH_3$ | H | 6-Cl | $CH_3$ | Br | 5-Cl |
| Cl | H | 6-Cl | Cl | Cl | 5-$CH_3$ |
| $CH_3$ | Cl | 6-Cl | $CH_3$ | Br | 5-$CH_3$ |
| $CH_3$ | Br | 5-Br | Cl | $CH_3$ | 5-Cl |
| Cl | $CH_3$ | 6-Cl | $CH_3$ | $CH_3$ | 5-Br |
| Br | $CH_3$ | 6-Br | $CH_3$ | H | 3-Cl, 6-$CH_3$ |
| $CH_3$ | Cl | 6-$CH_3$ | $CH_3$ | H | 3-Br, 6-$CH_3$ |
| $CH_3$ | $CH_3$ | 6-Cl | Cl | $CF_3$ | 6-Cl |
| $CH_3$ | Br | 6-$CH_3$ | | | |
| $CH_3$ | $CH_3$ | 6-Br | | | |

Tables 10 to 16

Compounds of the formula (I-2-a)

TABLE 10

X, Y and $Z_n$ as stated in Table 9 m = 1

Q = >C=O

TABLE 11

X, Y and $Z_n$ as stated in Table 9 m = 1

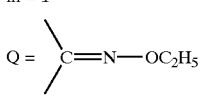

TABLE 12

X, Y and $Z_n$ as stated in Table 9 m = 1

Q = >C=N—$OC_2H_5$

TABLE 13

X, Y and $Z_n$ as stated in Table 9 m = 1

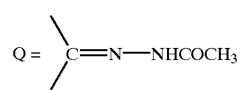
Q = C=N—NHCOCH₃

TABLE 14

X, Y and $Z_n$ as stated in Table 9 m = 1

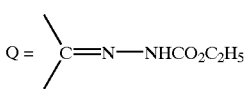
Q = C=N—NHCO₂C₂H₅

TABLE 15

X, Y and $Z_n$ as stated in Table 9 m = 1

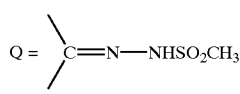
Q = C=N—NHSO₂CH₃

TABLE 16

X, Y and $Z_n$ as stated in Table 9 m = 1

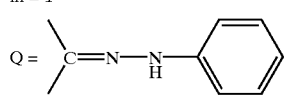
Q = C=N—NH—C₆H₅

In addition to the compounds mentioned in the Preparation Examples, the following compounds of the formula (I-3-a) may be specifically mentioned:

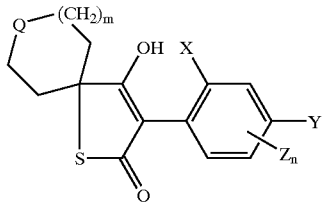

TABLE 17 m = 1

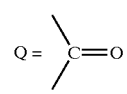
Q = CH—OH

| X | Y | $Z_n$ | X | Y | $Z_n$ |
|---|---|---|---|---|---|
| CH₃ | H | H | CH₃ | Br | 6-Cl |
| CH₃ | CH₃ | H | CH₃ | Cl | 6-Br |
| CH₃ | H | 5-CH₃ | Br | CH₃ | 6-Cl |

TABLE 17-continued m = 1

Q = CH—OH

| X | Y | $Z_n$ | X | Y | $Z_n$ |
|---|---|---|---|---|---|
| CH₃ | H | 6-CH₃ | CH₃ | CH₃ | 6-CN |
| CH₃ | CH₃ | 5-CH₃ | CH₃ | CN | 6-CH₃ |
| CH₃ | CH₃ | 6-CH₃ | CH₃ | CH₃ | 6-OCH₃ |
| CH₃ | CH₃ | 3,5-(CH₃)₂ | CH₃ | OCH₃ | 6-CH₃ |
| CH₃ | CH₃ | 3,6-(CH₃)₂ | Cl | Cl | 5-Cl |
| CH₃ | Cl | H | CH₃ | Cl | 5-CH₃ |
| Cl | CH₃ | H | Br | CH₃ | 5-Cl |
| Cl | H | 6-F | Br | CH₃ | 5-CH₃ |
| CH₃ | H | 6-Cl | CH₃ | Br | 5-Cl |
| Cl | H | 6-Cl | Cl | Cl | 5-CH₃ |
| CH₃ | Cl | 6-Cl | CH₃ | Br | 5-CH₃ |
| CH₃ | Br | 5-Br | Cl | CH₃ | 5-Cl |
| Cl | CH₃ | 6-Cl | CH₃ | CH₃ | 5-Br |
| Br | CH₃ | 6-Br | CH₃ | H | 3-Cl, 6-CH₃ |
| CH₃ | Cl | 6-CH₃ | CH₃ | H | 3-Br, 6-CH₃ |
| CH₃ | CH₃ | 6-Cl | Cl | CF₃ | 6-Cl |
| CH₃ | Br | 6-CH₃ | | | |
| CH₃ | CH₃ | 6-Br | | | |

Tables 18 to 24

Compounds of the formula (I-3-a)

TABLE 18

X, Y and $Z_n$ as stated in Table 17 m = 1

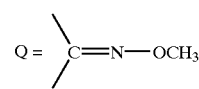
Q = C=O

TABLE 19

X, Y and $Z_n$ as stated in Table 17 m = 1

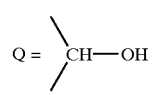
Q = C=N—OCH₃

TABLE 20

X, Y and $Z_n$ as stated in Table 17 m = 1

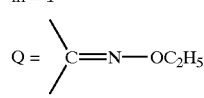
Q = C=N—OC₂H₅

TABLE 21

X, Y and $Z_n$ as stated in Table 17 m = 1

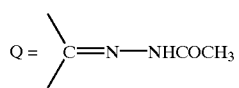

TABLE 22

X, Y and $Z_n$ as stated in Table 17 m = 1

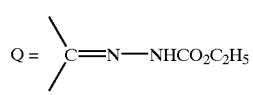

TABLE 23

X, Y and $Z_n$ as stated in Table 17 m = 1

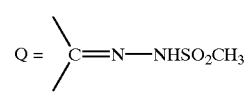

TABLE 24

X, Y and $Z_n$ as stated in Table 17 m = 1

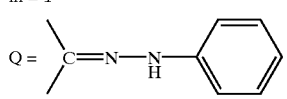

Using methyl N-[(2,4,6-trimethyl-phenyl)-acetyl]-1-amino-4-methoximinocyclohexane-carboxylate as starting material in accordance with process (A), the course of the process according to the invention can be represented by the following equation:

Using ethyl O-[(2,4-dichloro-phenyl)-acetyl]-1-hydroxy-4-oxo-cyclohexane-carboxylate in accordance with process (B), the course of the process according to the invention can be represented by the following equation:

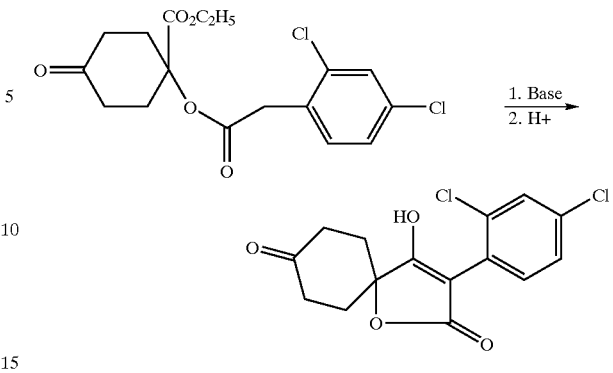

Using ethyl 2-[2,4-dimethyl-phenyl]-4-(4-methoxy)-benzylmercapto-4,4-(3-oxo-pentamethylene]-3-oxo-butyrate in accordance with process (C), the course of the process according to the invention can be represented by the following equation:

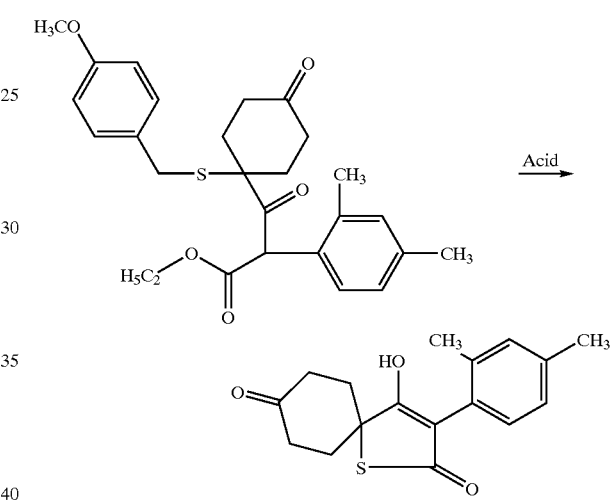

Using 3-[(2-chloro-4-methyl)-phenyl]-5,5-[(3-phenylimino)-pentamethylene]-pyrrolidin-2,4-dione and pivaloyl chloride as starting materials in accordance with process (Dα), the course of the process according to the invention can be represented by the following equation:

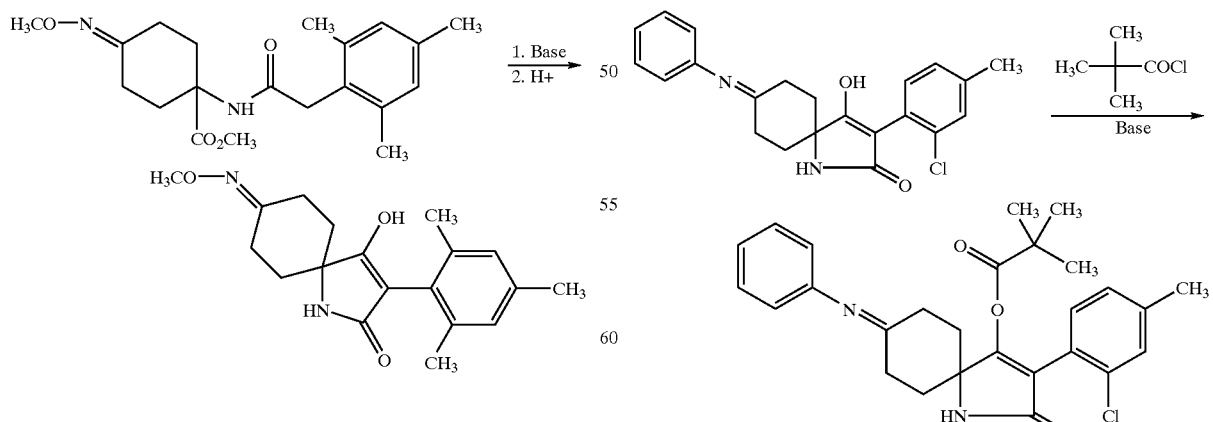

Using 3-[(4-chloro-2-methyl)-phenyl]-4-hydroxy-5,5-[(3-benzyloximino)-pentamethylene]-Δ³-dihydrofuran-2- one and acetic anhydride as starting materials in accordance with process (Dβ), the course of the process according to the invention can be represented by the following equation:

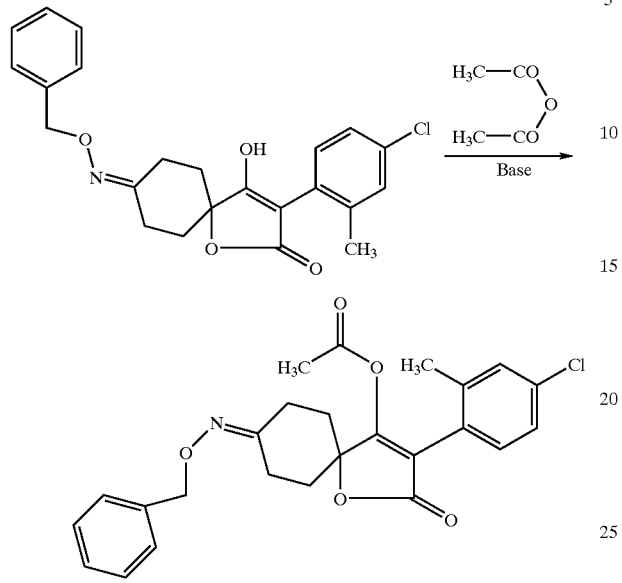

Using 3-[(2,4-dichloro-6-methyl)-phenyl]-5,5-[(3-oxo-pentamethylene)]-pyrrolidin-2,4-dione and ethoxyethyl chloroformate as starting materials in accordance with process (E), the course of the process according to the invention can be represented by the following equation:

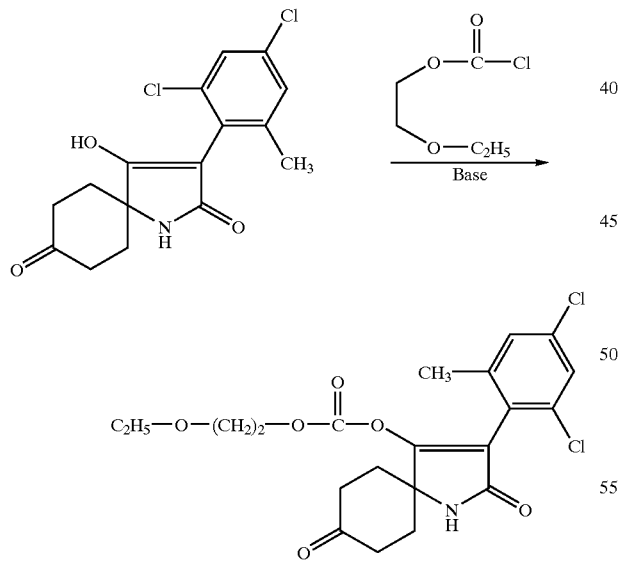

Using 3-[(2-chloro)-phenyl]-4-hydroxy-5,5-[3-(2-acetyl-hydrazino)-pentamethylene]-Δ³-dihydrofuran-2-one and methyl chloromonothioformate as starting materials in accordance with process (F) variant α, the course of the process according to the invention can be represented by the following equation:

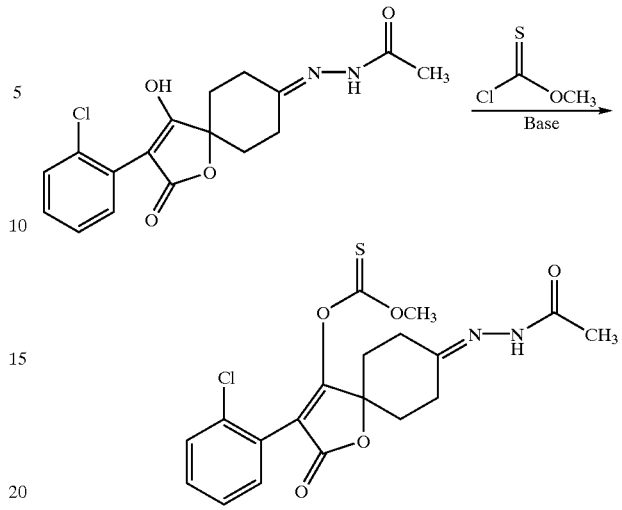

Using 3-[(2,6-dichloro-4-methyl)-phenyl]-4-hydroxy-4,4-[(3-methoximino)-pentamethylene]-Δ³-dihydrofuran-2-one and methanesulfonyl chloride as starting materials in accordance with process (G), the course of the reaction can be represented by the following equation:

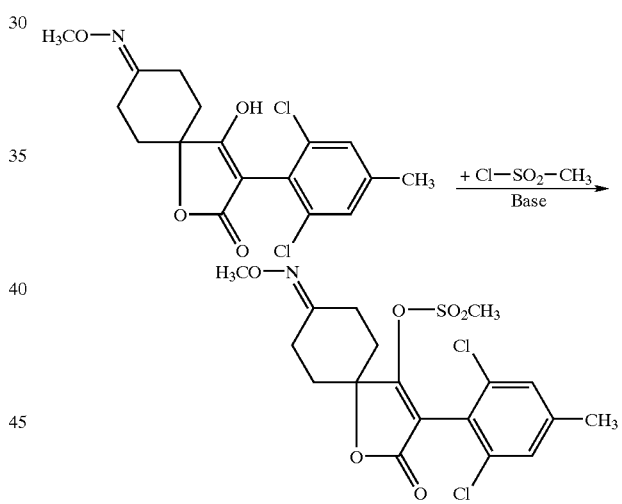

Using 3-[(2,5-dichloro)-phenyl]-5,5-[(3-oxa)-pentamethylene]-pyrrolidine-2,4-dione and 2,2,2-trifluoroethyl methanethio-phosphonic acid chloride as starting materials in accordance with process (H), the course of the reaction can be represented by the following equation:

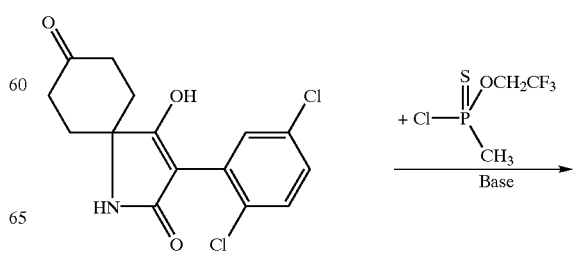

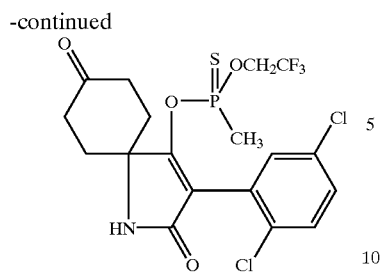

Using 3-[(2,4-dichloro)-phenyl]-5,5-[(3-ethoximino)-pentamethylene]-pytrolidine-2,4-dione and NaOH as starting materials in accordance with process (I), the course of the process according to the invention can be represented by the following equation:

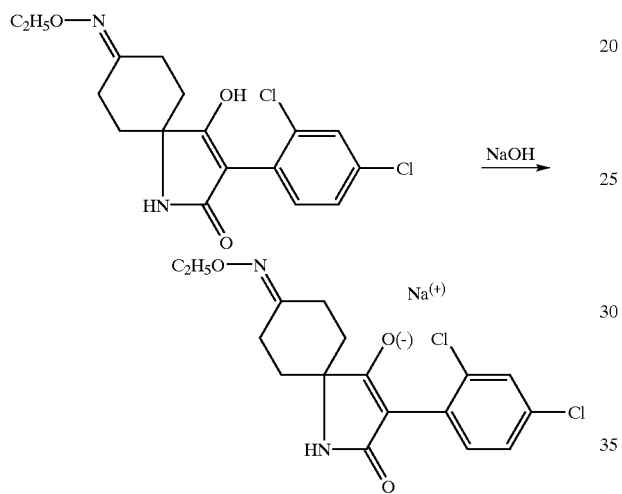

Using 3-[2,4,5-trimethyl)-phenyl]-4-hydroxy-5,5-[(2-oxo)-tetramethylene]-$\Delta^3$-dihydrofuran-2-one and ethyl isocyanate as starting materials in accordance with process (Jα), the course of the reaction can be represented by the following equation:

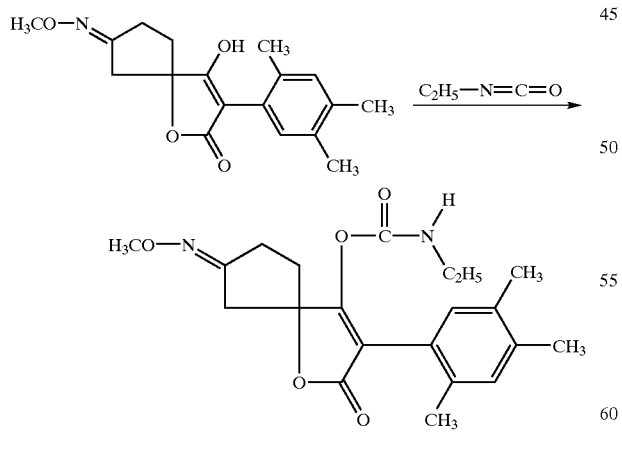

Using 3-[2,3,4,6-tetramethyl-phenyl]-5,5-[(4-methoximino)-pentamethylene]-pyrrolidine-2,4-dione and dimethylcarbamoyl chloride as starting materials in accordance with process (Jβ), the course of the reaction can be represented by the following equation:

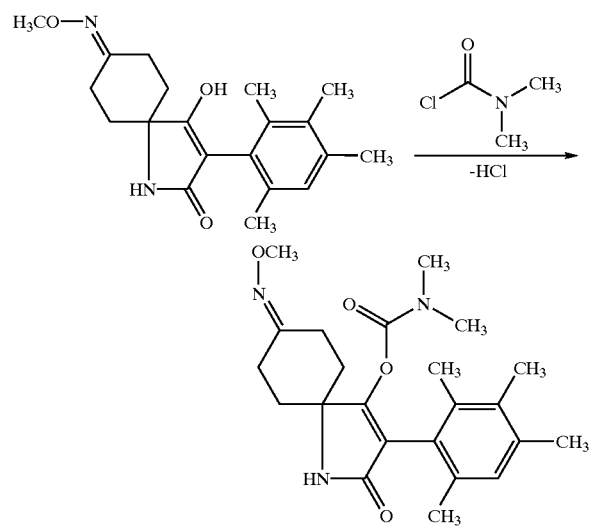

The compounds of the formula (II) required as starting materials for the process (A) according to the invention

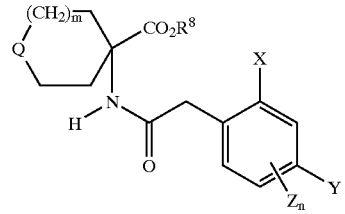

(II)

in which

Q, X, Y, Z, m, n and $R^8$ are each as defined above, are novel.

The acylamino acid esters of the formula (II) are obtained, for example, when amino acid derivatives of the formula (XV)

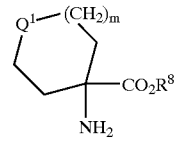

(XV)

in which $Q^1$, m and $R^8$ are each as defined above, are acylated with substituted phenyl acetyl halides of the formula (XVI)

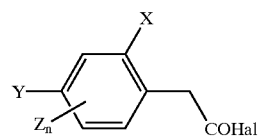

(XVI)

in which

X, Y, Z and n are each as defined above and

Hal represents chlorine or bromine (Chem. Reviews 52, 237–416 (1953); Bhattacharya, Indian J. Chem. 6, 341–5, 1968), or when acylamino acids of the formula (XVII)

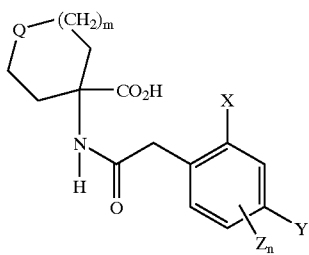

(XVII)

in which
Q, m, X, Y, Z and n are each as defined above,
are esterified (Chem. Ind. (London) 1568 (1968)).
The compounds of the formula (XVII)

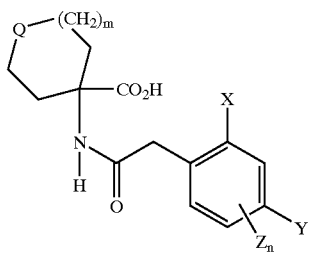

(XVII)

in which
Q, m, X, Y, Z and n are each as defined above,
are novel.

The compounds of the formula (XVII), are obtained when amino acids of the formula (XVIII)

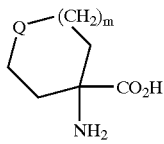

(XVIII)

in which
Q and m are each as defined above,
are acylated according to Schotten-Baumann with substituted phenylacetyl halides of the formula (XVI)

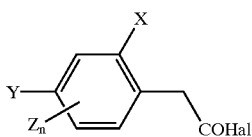

(XVI)

in which
X, Y, Z and n are each as defined above and
Hal represents chlorine or bromine
(Organikum, VEB Deutscher Verlag der Wissenschaften, Berlin 1977, p. 505).
Some of the compounds of the formula (XVI) are known. They can be prepared by customary methods (see, for example Henecka, Houben-Weyl, Methoden der Organischen Chemie, Vol. 8, p. 467–469 (1952)), or they are known from the patent applications cited at the outset or from WO 98/05638 and WO 97/36868.

Furthermore, the starting materials of the formula (II)

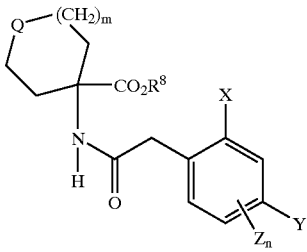

(II)

in which
Q, X, Y, Z, m, n and $R^8$ are each as defined above,
which are employed in the above process (A)
can be prepared by reacting aminonitriles of the formula (XIX)

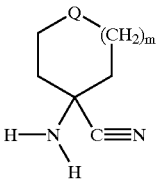

(XIX)

in which
Q and m are each as defined above,
with substituted phenyl acetyl halides of the formula

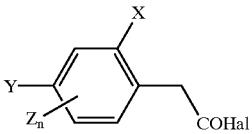

(XVI)

in which
X, Y, Z, n and Hal are each as defined above,
to give compounds of the formula (XX)

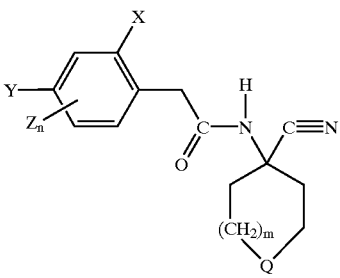

(XX)

in which
Q, X, Y, Z, m and n are each as defined above,
and these are subsequently subjected to acid alcoholysis.
The compounds of the formula (XX) are also novel.

By way of example, the reaction schemes below show synthesis paths to intermediates of the formula (II).

The capital letters after some of the formula numbers serve to differentiate between different meanings of Q. Some are also used in the Preparation Examples.

In the reaction schemes below, reference is made to compounds of the formulae

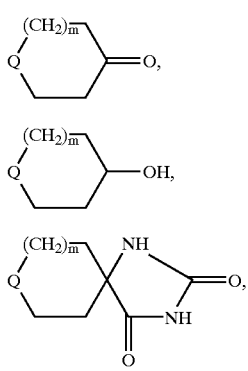

(XXV)
(XXVI)
(XXVIII)

in which Q and m are as defined above.

In the formula schemes compounds are given by way of example for different meanings of Q and of m=1. These meanings are, however, embraced by the formulae given above.

The radicals $R^{11}$ in

together may also represent an optionally methyl- or ethyl-substituted $C_2$–$C_3$-alkanediyl group.

Scheme 1:

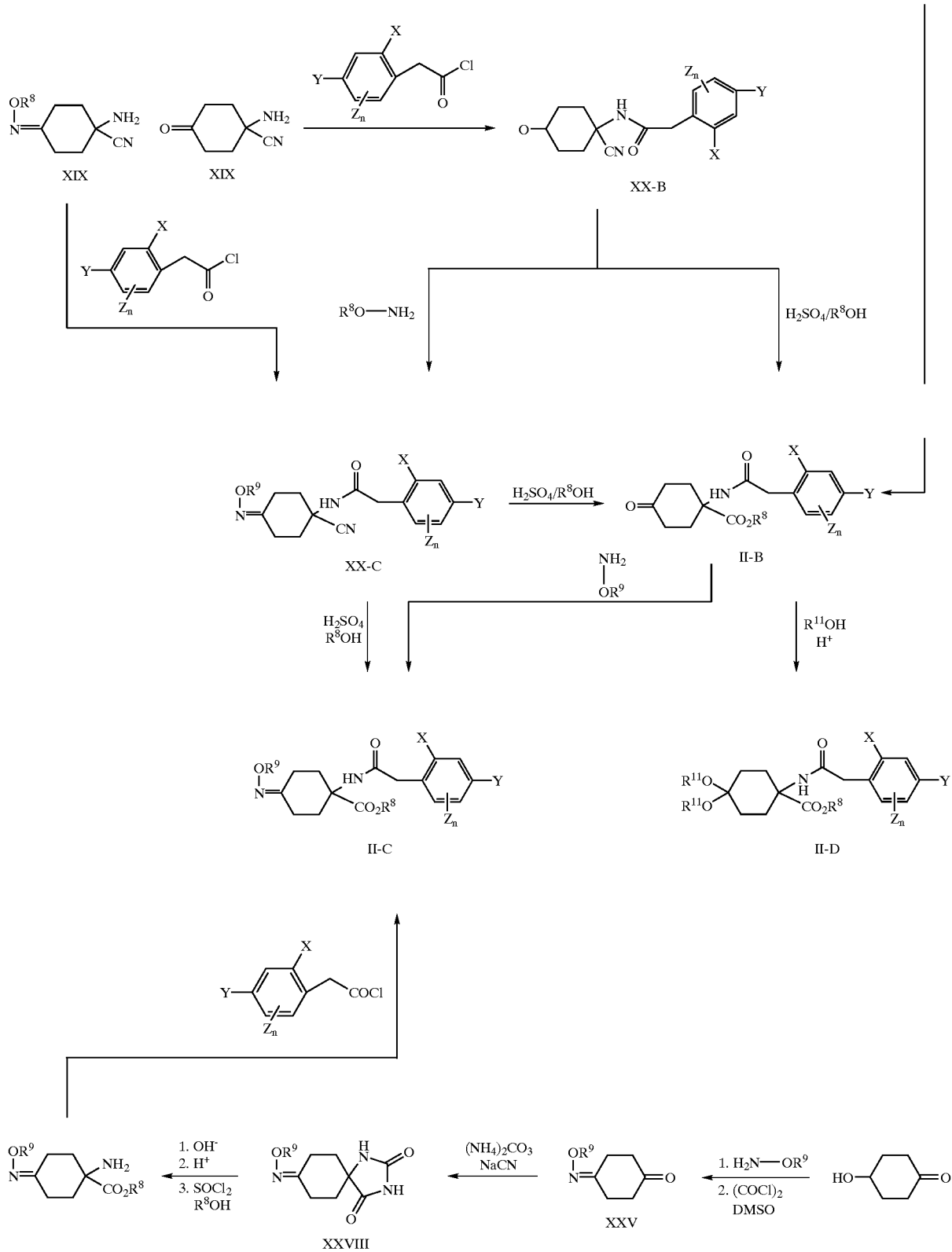

Scheme 1a:
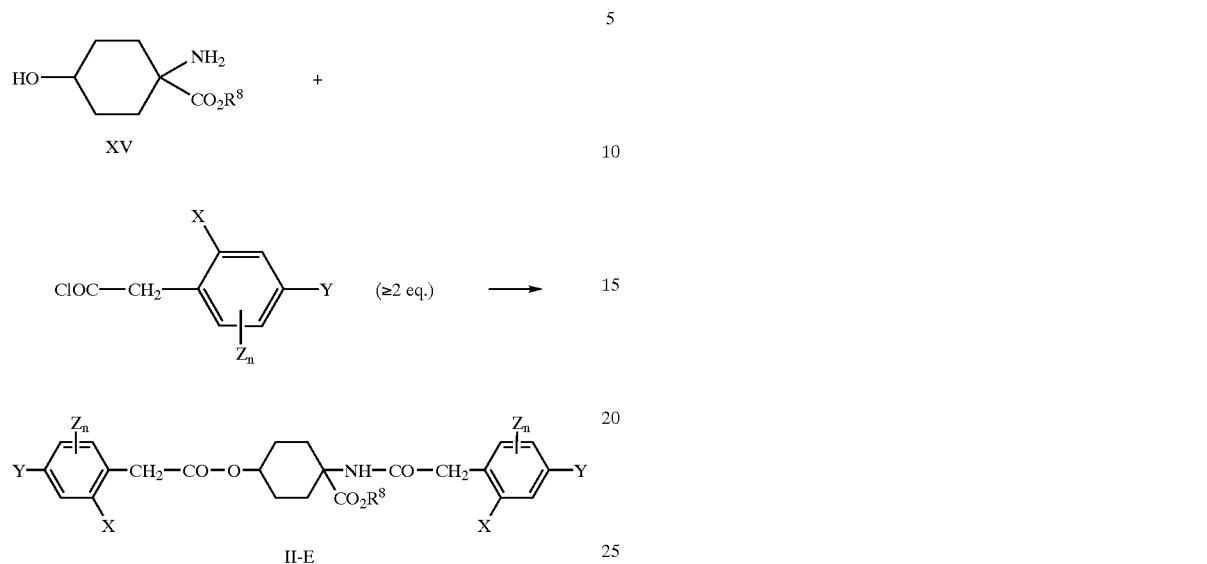
Scheme 2:
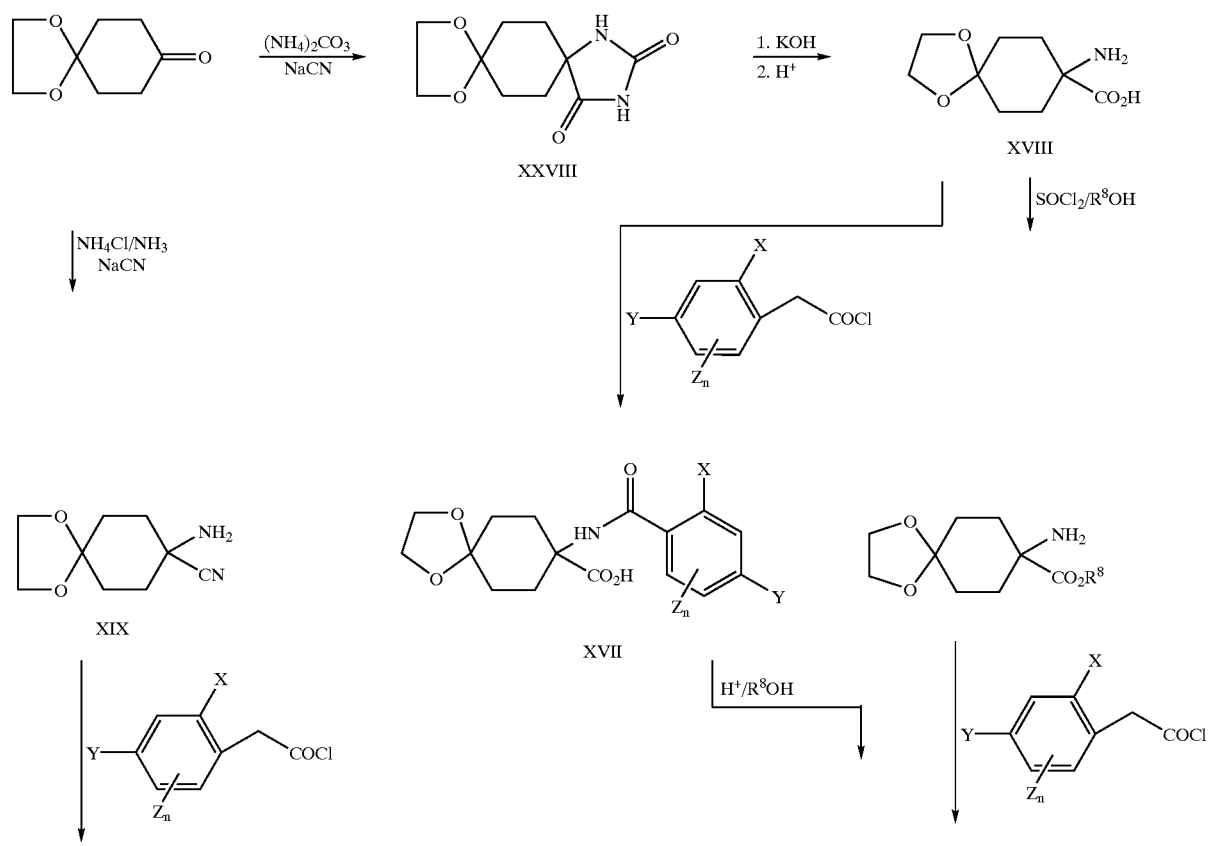

-continued

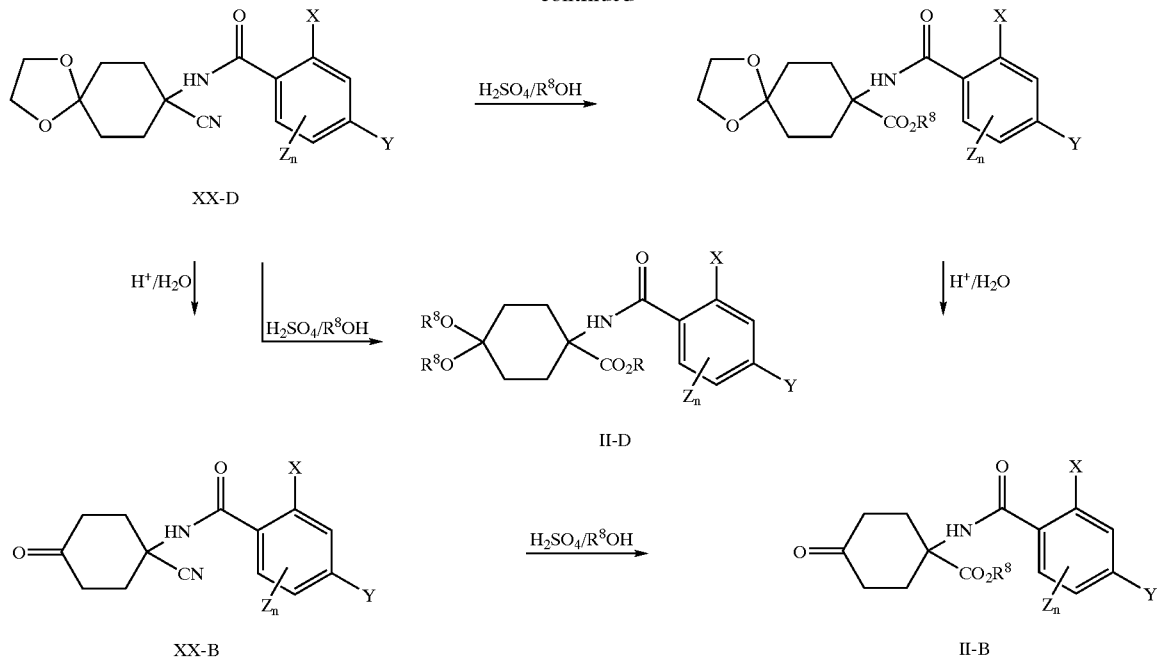

The compounds of the formula (III)

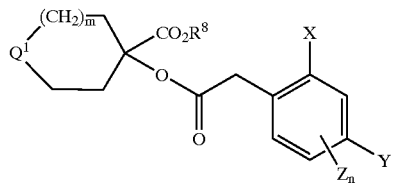

(III)

in which $Q^1$, X, Y, Z, m, n and $R^8$ are each as defined above, and which are required as starting materials for the process (B) according to the invention are novel.

They can be prepared in a simple manner by methods which are known in principle.

Thus, the compounds of the formula (III) are obtained, for example, when 2-hydroxycarboxylic esters of the formula (XXI)

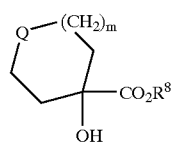
(XXI)

in which

Q, m and $R^8$ are each as defined above, are acylated with substituted phenylacetyl halides of the formula (XVI)

(XVI)

in which

X, Y, Z, n and Hal are each as defined above, (Chem. Reviews 52, 237–416 (1953)).

By way of example, the reaction scheme below shows synthesis paths to intermediates of the formula (III) and final products of the formula (I).

The capital letters after some of the formula numbers serve to differentiate between different meanings of Q. Some are also used in the Preparation Examples.

In the reaction scheme, reference is made to compounds of the formula

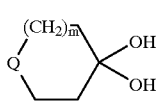
(XXX)

in which
Q and m are each as defined above.
In the formula scheme, compounds are given by way of example for different meanings of Q and of m=1. These meanings are, however, embraced by the formulae given above.
The radicals $R^{11}$ in
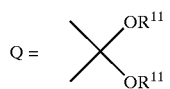
together may also represent an optionally methyl- or ethyl-substituted $C_2$–$C_3$-alkanediyl group.
Scheme 3:
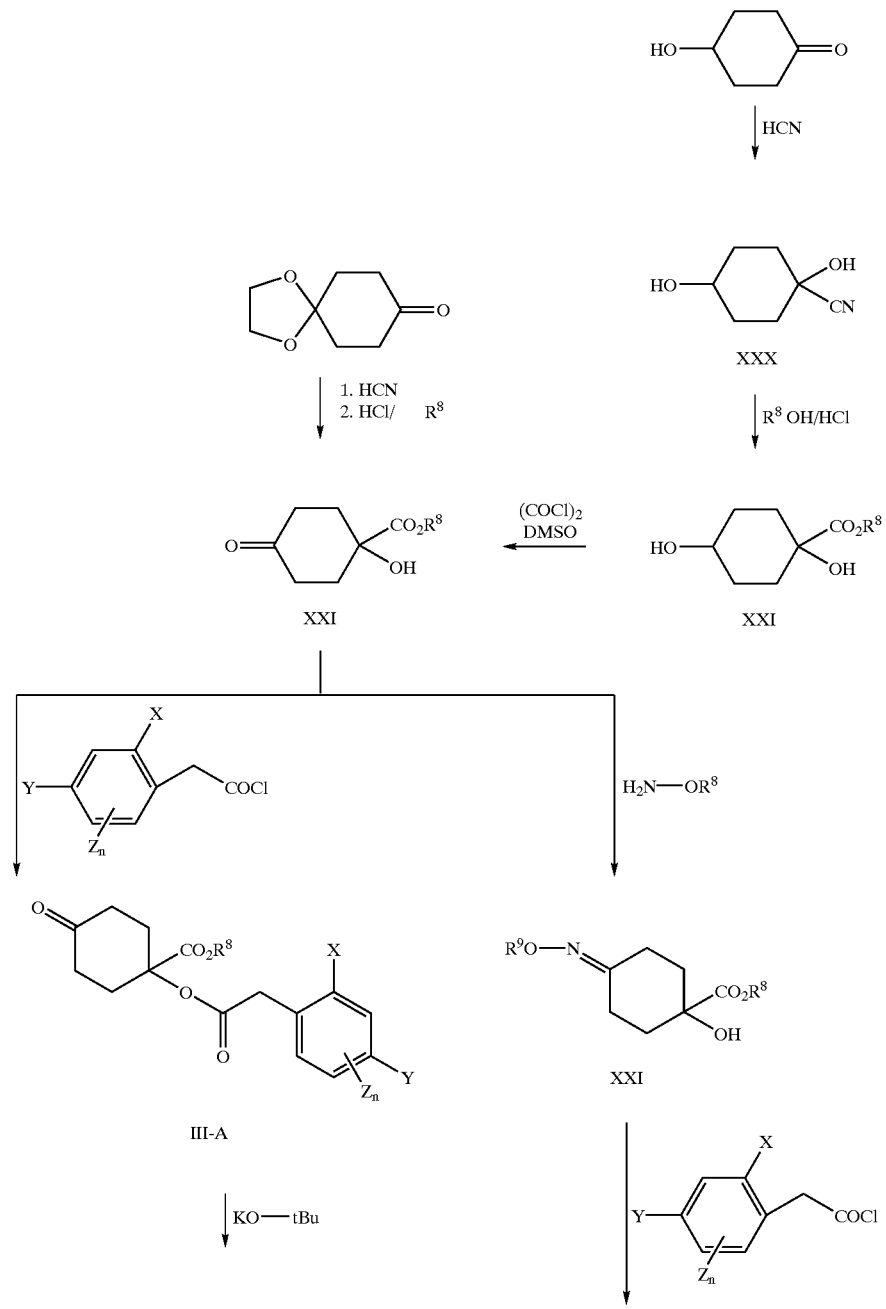

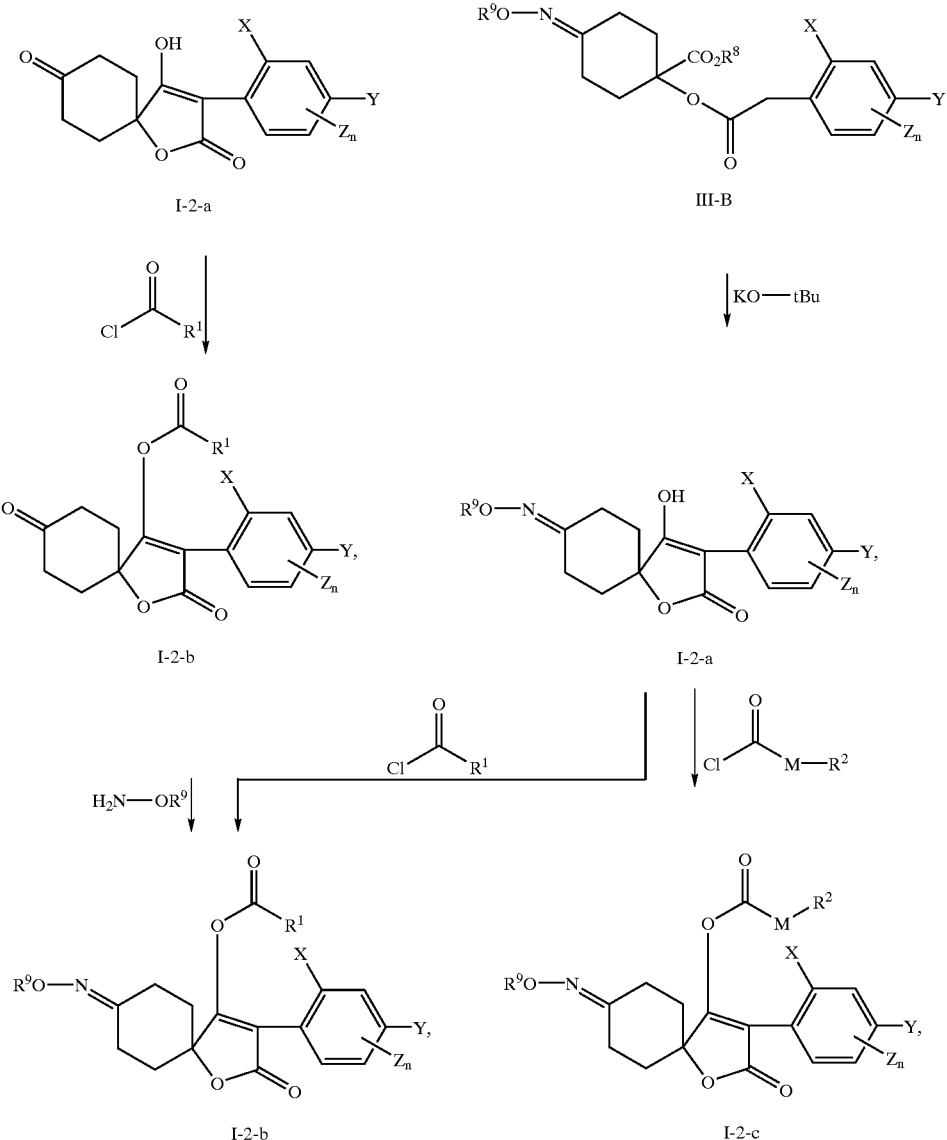
Scheme 3a:
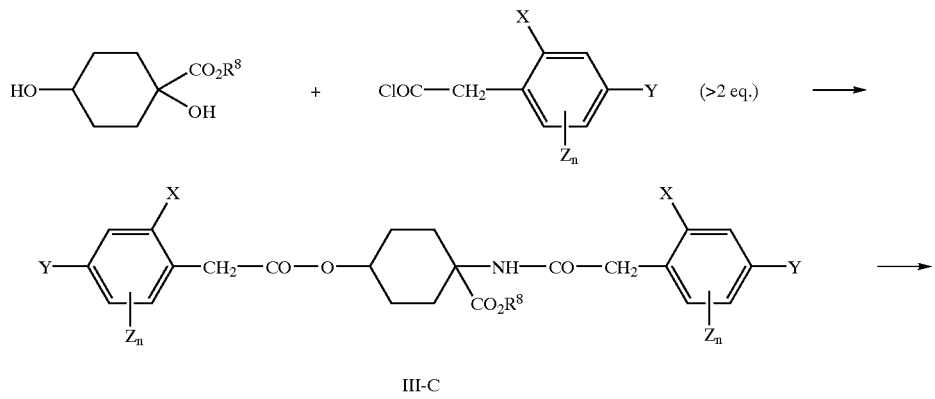

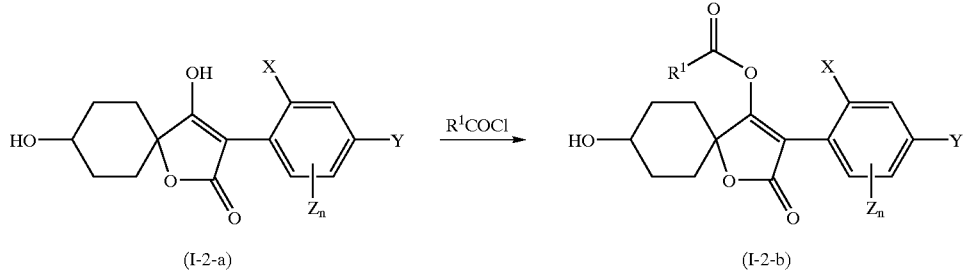

(I-2-a)                             (I-2-b)

The compounds of the formula (IV)

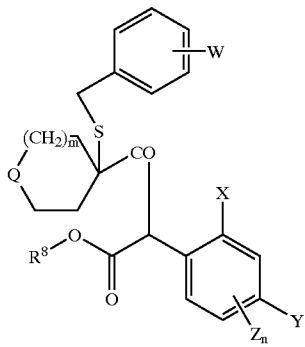

(IV)

in which

Q, W, X, Y, Z, m, n and $R^8$ are each as defined above,
and which are required as starting materials for the above process (C)
are novel.

They can be prepared by methods which are known in principle.

The compounds of the formula (IV) are obtained, for example, when substituted phenyl acetic esters of the formula (XXII)

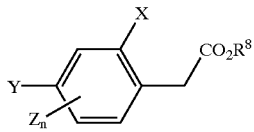

(XXII)

in which

X, Y, Z, n and $R^8$ are each as defined above,
are acylated with 2-benzylthio-carbonyl halides of the formula (XXIII)

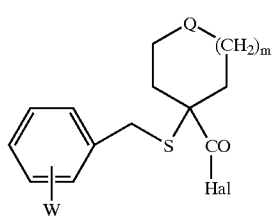

(XXIII)

in which

Q and W are each as defined above and
Hal represents halogen (in particular chlorine or bromine)
in the presence of strong bases (see, for example, M. S. Chambers, E. J. Thomas, D. J. Williams, J. Chem. Soc. Chem. Commun., (1987), 1228).

Some of the compounds of the formula (XXII) are known from the patent applications cited at the outset. Compounds of the formula (XXII) are obtained, for example, when compounds of the formula (XXIV)

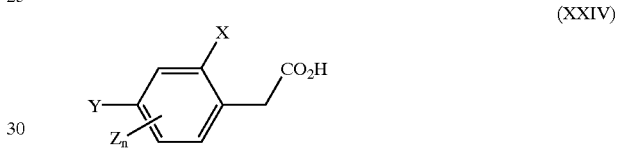

(XXIV)

in which

X, Y, Z and n are each as defined above,
are esterified in the presence of alcohols and dehydrating agents (for example conc. sulphuric acid),
or when alcohols are acylated with compounds of the formula (XVI)

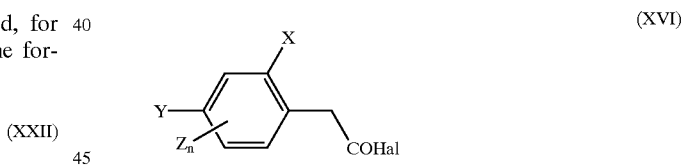

(XVI)

in which

X, Y, Z, n and Hal are each as defined above,
(Chem. Reviews 52, 237–416 (1953)).

The benzylthio-carbonyl halides of the formula (XXIII) are novel. They can be prepared by known processes (J. Antibiotics (1983), 26, 1589, WO 95/26 345).

The acyl halides of the formula (V), carboxylic anhydrides of the formula (VI), chloroformic acid esters or chloroformic acid thioesters of the formula (VII), chloromonothioformic acid esters or chlorodithioformic acid esters of the formula (VIII), sulphonyl chlorides of the formula (IX), phosphorus compounds of the formula (X) and metal hydroxides, metal alkoxides or amines of the formula (XI) and (XII), isocyanates of the formula (XIII) and carbamoyl chlorides of the formula (XIV) furthermore required as starting materials for carrying out process D, E, F, G, H, I and J according to the invention are generally known compounds of organic or inorganic chemistry.

The compounds of the formulae (V) to (XIV) are furthermore known from the patent applications cited at the outset, or they can be prepared by the methods mentioned therein.

The process (A) is characterized in that compounds of the formula (II) in which Q, X, Y, Z, m, n and $R^8$ are each as defined above are subjected to intramolecular condensation in the presence of a base.

In the process in accordance with (A), Q in the formula (II) may also represent the group

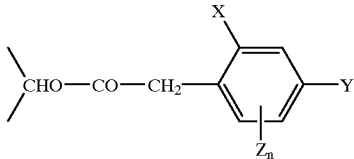

in which X, Y, Z and n are each as defined above. This also applies to the meaning of Q in the formula (III) in the process in accordance with (B).

Suitable diluents for use in the process (A) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, furthermore polar solvents, such as dimethyl sulphoxide, sulpholane, dimethylformamide and N-methyl-pyrrolidone, and also alcohols such as methanol, ethanol, propanol, iso-propanol, butanol, iso-butanol and tert-butanol.

All the customary proton acceptors can be employed as the base (deprotinating agent) when carrying out process (A) according to the invention. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase transfer catalysts, such as, for example, triethylbenzylammonium chloride, tetrabutylammonium bromide, Adogen 464 (=methyltrialkyl ($C_8$–$C_{10}$)ammonium chloride) or TDA 1 (=tris-(methoxyethoxyethyl)amine). Alkali metals, such as sodium or potassium, can moreover be used. Alkali metal and alkaline earth metal amides and hydrides, such as sodium amide, sodium hydride and calcium hydride, and in addition also alkali metal alkoxides, such as sodium methoxide, sodium ethoxide and potassium tert-butoxide, can furthermore be employed.

When carrying out the process (A) according to the invention, the reaction temperatures can be varied within a relatively large range. In general, the reaction is carried out at temperatures between 0° C. and 250° C., preferably between 50° C. and 150° C.

The process (A) according to the invention is generally carried out under atmospheric pressure.

When carrying out the process (A) according to the invention, the reaction components of formula (II) and the deprotonating base are generally employed in approximately equimolar to twice the equimolar amounts. However, it is also possible to use a relatively large excess (up to 3 mol) of one or the other of the components.

The process (B) is characterized in that compounds of the formula (III) in which Q, X, Y, Z, m, n and $R^8$ are each as defined above are subjected to intramolecular condensation in the presence of a diluent and in the presence of a base.

Suitable diluents for use in the process (B) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, furthermore polar solvents, such as dimethyl sulphoxide, sulpholane, dimethylformamide and N-methyl-pyrrolidone, and also alcohols such as methanol, ethanol, propanol, iso-propanol, butanol, iso-butanol and tert-butanol.

All the customary proton acceptors can be employed as the base (deprotinating agent) when carrying out process (B) according to the invention. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase transfer catalysts, such as, for example, triethylbenzylammonium chloride, tetrabutylammonium bromide, Adogen 464 (=methyltrialkyl ($C_8$–$C_{10}$)ammonium chloride) or TDA 1 (=tris-(methoxyethoxyethyl)amine). Alkali metals, such as sodium or potassium, can moreover be used. Alkali metal and alkaline earth metal amides and hydrides, such as sodium amide, sodium hydride and calcium hydride, and in addition also alkali metal alkoxides, such as sodium methoxide, sodium ethoxide and potassium tert-butoxide, can furthermore be employed.

When carrying out the process (B) according to the invention, the reaction temperatures can be varied within a relatively large range. In general, the reaction is carried out at temperatures between 0° C. and 250° C., preferably between 50° C. and 150° C.

The process (B) according to the invention is generally carried out under atmospheric pressure.

When carrying out the process (B) according to the invention, the reaction components of formula (III) and the deprotonating base are generally employed in approximately equimolar amounts. However, it is also possible to use a relatively large excess (up to 3 mol) of one or the other of the components.

The process (C) is characterized in that compounds of the formula (IV) in which Q, W, X, Y, Z, m, n and $R^8$ are each as defined above are subjected to an intramolecular cyclization in the presence of an acid and, if appropriate, in the presence of a diluent.

Diluents which are suitable for use in the process (C) according to the invention are all inert organic solvents. Preference is given to using hydrocarbons, such as toluene and xylene, furthermore halogenated hydrocarbons, such as dichloromethane, chloroform, ethylene chloride, chlorobenzene, dichlorobenzene, moreover polar solvents, such as dimethyl sulphoxide, sulpholane, dimethylformamide and N-methyl-pyrrolidone. It is also possible to employ alcohols such as methanol, ethanol, propanol, iso-propanol, butanol, isobutanol, tert-butanol.

If appropriate, the acid which is employed may also serve as diluent.

Acids which are suitable for use in the process (C) according to the invention are all customary inorganic and organic acids, such as, for example, hydrohalic acids, sulphuric acids, alkyl-, aryl- and halogenoalkylsulphonic acids, in particular halogenated alkylcarboxylic acids, such as, for example, trifluoroacetic acid.

When carrying out the process (C) according to the invention, the reaction temperatures can be varied within a relatively wide range. In general, the reaction is carried out at temperatures between 0° C. and 250° C., preferably between 50° C. and 150° C.

The process (C) according to the invention is generally carried out under atmospheric pressure.

When carrying out the process (C) according to the invention, the reaction components of the formula (IV) and the acid are employed, for example, in equimolar amounts. However, it is also possible to employ the acid as solvent or as catalyst.

The process (Dα) is characterized in that compounds of the formulae (I-1-a) to (I-3-a) are in each case reacted with carboxylic halides of the formula (V), if appropriate in the presence of a diluent and if appropriate in the presence of an acid binder.

Diluents which are suitable for use in the process (Dα) according to the invention are all solvents which are inert towards the acyl halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, furthermore ketones, such as acetone and methyl isopropyl ketone, nitriles such as acetonitrile, moreover ethers, such as diethyl ether, tetrahydrofuran and dioxane, and furthermore carboxylic esters, such as ethyl acetate, and also strongly polar solvents, such as dimethyl sulphoxide and sulpholane. The hydrolytic stability of the acyl halide permitting, the reaction can also be carried out in the presence of water.

Suitable acid binders for the reaction according to the process (Dα) according to the invention are customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethyl-aniline, furthermore alkaline earth metal oxides, such as magnesium oxide and calcium oxide, moreover alkali metal and alkaline earth metal carbonates, such as sodium carbonate, potassium carbonate and calcium carbonate and also alkali metal hydroxides such as sodium hydroxide and potassium hydroxide.

When carrying out the process (Dα) according to the invention, the reaction temperatures can be varied within a relatively wide range. In general, the reaction is carried out at temperatures between −20° C. and +150° C., preferably between 0° C. and 100° C.

When carrying out the process (Dα) according to the invention, the starting materials of the formulae (I-1-a) to (I-3-a) and the carbonyl halide of the formula (V) are generally each employed in approximately equivalent amounts. However, it is also possible to employ a relatively large excess (up to 5 mol) of the carbonyl halide. Work-up is carried out by customary methods.

The process (Dβ) is characterized in that compounds of the formula (I-1-a) to (I-3-a) are reacted with carboxylic anhydrides of the formula (IV), if appropriate in the presence of a diluent and if appropriate in the presence of an acid binder.

Diluents which are suitable for use in the process (Dβ) according to the invention are preferably those diluents which are also preferred when acyl halides are used. A carboxylic anhydride employed in excess can moreover also simultaneously function as the diluent.

Acid binders which are optionally added in the process (Dβ) are preferably those acid binders which are also preferred when acyl halides are used.

The reaction temperatures in the process (Dβ) according to the invention can be varied within a relatively wide range. In general, the reaction is carried out at temperatures between −20° C. and +150° C., preferably between 0° C. and 100° C.

When carrying out the process (Dβ) according to the invention, the starting materials of the formulae (I-1-a) to (I-3-a) and the carboxylic anhydride of the formula (VI) are generally each employed in approximately equivalent amounts. However, it is also possible to employ a relatively large excess (up to 5 mol) of the carboxylic anhydride. Work-up is carried out by customary methods.

In general, diluent and the carboxylic anhydride which is present in excess, and also the carboxylic acid that is formed are removed by distillation or by washing with an organic solvent or with water.

The process (E) is characterized in that compounds of the formulae (I-1-a) to (I-3-a) are in each case reacted with chloroformic acid esters or chloroformic acid thiol esters of the formula (VII), if appropriate in the presence of a diluent and if appropriate in the presence of an acid binder.

Acid binders which are suitable for the reaction according to the process (E) according to the invention are all customary acid acceptors. Preference is given to using tertiary amines, such as triethylamine, pyridine, DABCO, DBU, DBA, Hünig base and N,N-dimethyl-aniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides such as sodium hydroxide and potassium hydroxide. Suitable diluents for use in the process (E) according to the invention are all solvents which are inert towards the chloroformic acid esters or chloroformic acid thiol esters. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methylisopropyl ketone, nitriles such as acetonitrile, furthermore ethers, such as diethyl ether, tetrahydrofuran and dioxane, and additionally carboxylic esters, such as ethyl acetate, and also strongly polar solvents, such as dimethyl sulphoxide and sulpholane.

When carrying out the process (E) according to the invention, the reaction temperatures can be varied within a relatively wide range. If the reaction is carried out in the presence of the diluent and an acid binder, the reaction temperatures are generally between −20° C. and +100° C., preferably between 0° C. and 50° C.

The process (E) according to the invention is generally carried out under atmospheric pressure.

When carrying out the process (E) according to the invention, the starting materials of the formulae (I-1-a) to (I-3-a) and the appropriate chloroformic acid ester or chloroformic acid thiol ester of the formula (VII) are generally each employed in approximately equivalent amounts. However, it is also possible to employ a relatively large excess (up to 2 mol) of one or the other component. Work-up is carried out by customary methods. In general, precipitated salts are removed and the reaction mixture which remains is concentrated by removing the diluent under reduced pressure.

The process (F) according to the invention is characterized in that compounds of the formulae (I-1-a) to (I-3-a) are in each case reacted with compounds of the formula (VIII) in the presence of a diluent and, if appropriate, in the presence of an acid binder.

In the preparation process (F), approximately 1 mol of chloromonothioformic acid ester or chlorodithioformic acid ester of the formula (VIII) is reacted per mole of starting material of the formulae (I-1-a) to (I-3-a), at 0 to 120° C., preferably at 20 to 60° C.

Diluents which may be added, if appropriate, are all inert polar organic solvents, such as ethers, nitriles, ketones, carboxylic esters, amides, sulphones, sulphoxides, but also halogenoalkanes.

Preference is given to using dimethyl sulphoxide, tetrahydrofurane, ethyl acetate, dimethylformamide or methylene chloride.

If, in a preferred embodiment, the enolate salt of the compounds (I-1-a) to (I-3-a) is prepared by addition of strong deprotonating agents, such as, for example, sodium hydride or potassium tert-butoxide, the further addition of acid binders can be dispensed with.

If acid binders are employed, then customary inorganic or organic bases are suitable, and examples which may be mentioned are sodium hydroxide, sodium carbonate, potassium carbonate, pyridine, triethylamine.

The reaction can be carried out under atmospheric pressure or under elevated pressure, and is preferably carried out under atmospheric pressure. Work-up is carried out by customary methods.

The process (G) according to the invention is characterized in that compounds of the formulae (I-1-a) to (I-3-a) are in each case reacted with sulphonyl chlorides of the formula (IX), if appropriate in the presence of a diluent and if appropriate in the presence of an acid binder.

In the preparation process (G), approximately 1 mol of sulphonyl chloride of the formula (IX) is reacted per mole of starting material of the formula (I-1-a) to (I-3-a), at −20 to 150° C., preferably at 20 to 70° C.

Diluents which may be added, if appropriate, are all inert polar organic solvents, such as ethers, amides, ketones, carboxylic esters, nitriles, sulphones, sulphoxides or halogenated hydrocarbons such as methylene chloride.

Preference is given to using dimethyl sulphoxide, ethyl acetate, acetonitrile, tetrahydrofurane, dimethylformamide, methylene chloride.

If, in a preferred embodiment, the enolate salt of the compounds (I-1-a) to (I-3-a) is prepared by addition of strong deprotinating agents (such as, for example, sodium hydride or potassium tert-butoxide), the further addition of acid binders can be dispensed with.

If acid binders are employed, then customary inorganic or organic bases are suitable, and examples which may be mentioned are, sodium hydroxide, sodium carbonate, potassium carbonate, pyridine, triethylamine.

The reaction can be carried out under atmospheric pressure or under elevated pressure, and is preferably carried out under atmospheric pressure. Work-up is carried out by customary methods.

The process (H) according to the invention is characterized in that compounds of the formulae (I-1-a) to (I-3-a) are in each case reacted with phosphorus compounds of the formula (X), if appropriate in the presence of a diluent and if appropriate in the presence of an acid binder.

In the preparation process (H), 1 to 2, preferably 1 to 1.3, mol of the phosphorus compound of the formula (X) is reacted per mole of the compounds (I-1-a) to (I-3-a), at temperatures between −40° C. and 150° C., preferably between −10 and 110° C., to obtain compounds of the formulae (I-1-e) to (I-3-e).

Diluents which may be added, if appropriate, are all inert polar organic solvents, such as ethers, amides, ketones, carboxylic esters, nitrites, alcohols, sulphides, sulphones, sulphoxides, etc.

Preference is given to using acetonitrile, dimethyl sulphoxide, ethyl acetate, tetrahydrofuran, dimethylformamide or methylene chloride.

Acid binders which may be added, if appropriate, are customary inorganic or organic bases, such as hydroxides, carbonates or amines. Examples include sodium hydroxide, sodium carbonate, potassium carbonate, pyridine, triethylamine.

The reaction can be carried out under atmospheric pressure or under elevated pressure, and is preferably carried out under atmospheric pressure. Work-up is carried out by customary methods of organic chemistry. The end products obtained are preferably purified by crystallization, chromatographic purification or by so-called "incipient distillation", i.e. removal of the volatile constituents under reduced pressure.

The process (I) is characterized in that compounds of the formulae (I-1-a) to (I-3-a) are reacted with metal hydroxides or metal alkoxides of the formula (XI) or amines of the formula (XII), if appropriate in the presence of a diluent.

Preferred diluents for the process (I) according to the invention are ethers such as tetrahydrofuran, dioxane, diethyl ethers or else alcohols such as methanol, ethanol, isopropanol, but also water. The process (I) according to the invention is generally carried out under atmospheric pressure. The reaction temperatures are generally between −20° C. and 100° C., preferably between 0° C. and 50° C.

The process (J) according to the invention is characterized in that compounds of the formulae (I-1-a) to (I-3-a) are in each case reacted with (Jα) compounds of the formula (XIII), if appropriate in the presence of a diluent and if appropriate in the presence of a catalyst, or (Jβ) with compounds of the formula (XIV), if appropriate in the presence of a diluent and if appropriate in the presence of an acid binder.

In the preparation process (Jα), approximately 1 mol of isocyanate of the formulae (XIII) is reacted per mole of starting material of the formulae (I-1-a) to (I-3-a), at 0 to 100° C., preferably at 20 to 50° C.

Diluents which may be added, if appropriate, are all inert organic solvents, such as ethers, amides, nitriles, ketones, carboxylic esters, sulphones, sulphoxides.

If appropriate, catalysts may be added to promote the reaction. Catalysts which can be very advantageously employed are organotin compounds, such as, for example, dibutyltin dilaurate. The reaction is preferably carried out under atmospheric pressure.

In the preparation process (Jβ), approximately 1 mol of carbamoyl chloride of the formula (XIV) is reacted per mole of starting material of the formulae (I-1-a) to (I-3-a), at 0 to 150° C., preferably at 20 to 70° C.

Diluents which may be added, if appropriate, are all inert polar organic solvents, such as ethers, amides, nitriles, ketones, carboxylic esters, sulphones, sulphoxides or halogenated hydrocarbons.

Preference is given to using dimethyl sulphoxide, tetrahydrofuran, ethyl acetate, dimethylformamide or methylene chloride.

If, in a preferred embodiment, the enolate salt of the compound (I-1-a) to (I-3-a) is prepared by addition of strong deprotonating agents (such as, for example, sodium hydride or potassium tert-butoxide), the further addition of acid binders can be dispensed with.

If acid binders are used, then customary inorganic or organic bases are suitable, and examples which may be mentioned are sodium hydroxide, sodium carbonate, potassium carbonate, triethylamine or pyridine.

The reaction can be carried out under atmospheric pressure or under elevated pressure, and is preferably carried out under atmospheric pressure. Work-up is carried out by customary methods.

The active compounds are suitable for controlling animal pests, preferably arthropods and nematodes, in particular insects and arachnids, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellho scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypli, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium comi, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flaminea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretelia, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varive stis,* Atomaria spp., *Oryzaephilus surinamensis, Antho nomus* spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Cono derus spp., *Melolontha melolontha, Amphimallon soisti tialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds according to the invention are distinguished by a high insecticidal and acaricidal activity.

They can be employed particularly successfully against insects which are harmful to plants, such as, for example, against the larvae of the mustard beetle (*Phaedon cochleariae*) or against the larvae of the green rice leafhopper (*Nephotettix cincticeps*), against peach aphids (*Myzus persicae*) or else against the fruit tree red spider mite (*Panonychus ulmi*).

The active compounds according to the invention can furthernore be used as defoliants, desiccants, haulm-killers and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindemia, Lamium, Veronica, Abutilon, Emex, Datura, Viola, Galeopsis, Papaver, Centaurea, Trifolium, Ranunculus and Taraxacum.

Dicotyledon crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cycnodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total controlling of weeds, for example on industrial terrain and rail tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on ornamental and sports lawns and meadow areas and for the selective control of weeds in annual cultures.

The active compounds according to the invention are particularly suitable for selectively controlling monocotyledonous weeds in dicotyledonous crops by the pre- and post-emergence method. For example, they can be employed very successfully for controlling harmful grasses in cotton or sugar beet.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forining agents.

If the extender used is water, it is also possible to employ for example organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are:

for example, ammonium salts and ground natural minerals, such as kaolins, clays, talc, chalk, quartz, attapulgite, montmorillonite or diatomaceous earth, and ground synthetic minerals, such as highly disperse silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifying and/or foam-forming agents are: for example, non-ionic and anionic emulsifiers, such as polyoxyethylene fatty acid esters, polyoxyethylene fatty alcohol ethers, for example alkylaryl polyglycol ethers, alkyl sulphonates, alkyl sulphates, aryl sulphonates and also protein hydrolysates; suitable dispersing agents are: for example, lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, and also natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compound according to the invention can be present in its commercially available formulations and in the use forms prepared from these formulations as a mixture with other active compounds, such as insecticides, attractants, sterilizing agents, acaricides, nematicides, fungicides, growth-regulating substances or herbicides. The insecticides include, for example, phosphoric acid esters, carbamates, carboxylic acid esters, chlorinated hydrocarbons, phenylureas, substances produced by microorganisms, and the like.

Particularly favourable mixing partners are, for example, the following:

Fungicides:

2-aminobutane; 2-anilino4-methyl-6-cyclopropyl-pyri midine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil. fenpropidin, fenpropimorph, fentin acetate, fentin hydroxide, ferbam, ferimzone, fluazinam, tiudioxonil, fluoromide. fluquinconazole, flusilazole, fltisulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), ipriodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichiamide, tricyclazole, tridemorph, triflumizole, triforine, triticonazole, validamycin A, vinclozolin, zineb, ziram.

Bactericides:

bronopol, dichlorophen, nitrapyrin, nickel dimethyldithiocarbamate, kasugamycin, octhilinon, furancarboxylic acid, oxytetracyclin, probenazol, streptomycin, tecloftalam, copper sulphate and other copper preparations.

Insecticides/acaricide/nematicides:

Abamectin, Acephate, Acetamiprid, Acrinathrin, Alanycarb, Aldicarb, Aldoxycarb, Alpha-cypermethrin, Alphamethnrn, Amitraz, Avermectin, AZ 60541, Azadirachtin, Azamethiphos, Azinphos A, Azinphos M, Azocyclotin,

*Bacillus popilliae, Bacillus sphaericus, Bacillus subtilis, Bacillus thuringiensis,* Baculoviren, *Beauveria bassiana, Beauveria tenella,* Bendiocarb, Benfuracarb, Bensultap, Benzoximate, Betacyfluthrin, Bifenazate, Bifenthrin, Bioethanomethrin, Biopermethrin, BPMC, Bromophos A, Bufencarb, Buprofezin, Butathiofos, Butocarboxim, Butylpyridaben, Cadusafos, Carbaryl, Carbofuran, Carbophenothion, Carbosulfan, Cartap, Chloethocarb, Chlorethoxyfos, Chlorfenapyr, Chlorfenvinphos, Chlorfluazuron, Chlormephos, Chlorpyrifos, Chlorpyrifos M, Chlovaporthrin, Cis-Resmethrin, Cispermethrin, Clocythrin, Cloethocarb, Clofentezine, Cyanophos, Cycloprene, Cycloprothrin, Cyfluthrin, Cyhalothrin, Cyhexatin, Cypermethrin, Cyromazine, Deltamethrin, Demeton M, Demeton S, Demeton-S-methyl, Diacloden, Diafen-thiuron, Diazinon, Dichlorvos, Diflubenzuron, Dimethoat, Dimethylvinphos, Diofenolan, Disulfoton, Docusat-sodium, Dofenapyn, Eflusilanate, Emamectin, Empenthrin, Endosulfan, Entomopfthora spp., Esfen-valerate, Ethiofencarb, Ethion, Ethoprophos, Etofenprox, Etoxazole, Etrimfos, Fenamiphos, Fenazaquin, Fenbutatin oxide, Fenitrothion, Fenothiocarb, Fenoxacrim, Fenoxycarb, Fenpropathrin, Fenpyrad, Fenpyrithrin, Fenpyroximate, Fenvalerate, Fipronil, Fluazinam, Fluazuron, Flubrocythrinate,. Flucycloxuron, Flucythrinate, Flufenoxuron, Flutenzine, Fluvalinate, Fonophos, Fosmethilan, Fosthiazate, Fub-fenprox, Furathiocarb, granulosis viruses, Halofenozide, HCH, Heptenophos, Hexaflumuron, Hexythiazox, Hydroprene, Imidacloprid, Isazofos, Isofenphos, Isoxathion, Ivermectin, nuclear polyhedrosis viruses, Lambda-cyhalothrin, Lufenuron, Malathion, Mecarbam, Metaldehyde, Methamidophos, Metharhizium anisopliae, Metharhizium flavoviride, Methidathion, Methiocarb, Methomyl, Methoxyfenozide, Metolcarb, Metoxadiazone, Mevinphos, Milbemectin, Monocrotophos, Naled, Nitenpyram, Nithiazine, Novaluron, Omethoat, Oxamyl, Oxydemethon M,

*Paecilomyces fumosoroseus*, Parathion A, Parathion M, Peimethrin, Phenthoat, Phorat, Phosalone, Phosmet, Phosphamidon, Phoxim, Pirimicarb, Pirimiphos A, Pirimiphos M, Profenofos, Promecarb, Propoxur, Prothiofos, Prothoat, Pymetrozine, Pyraclofos, Pyresmethrin, Pyrethrum, Pyridaben, Pyridathion, Pyrimidifen, Pyriproxyfen, Quinalphos, Ribavirin, Salithion, Sebufos, Silafluofen, Spinosad, Sulfotep, Sulprofos, Tau-fluvalinate, Tebufenozide, Tebufenpyrad, Tebupirimiphos, Teflubenzuron, Tefluthrin, Temephos, Temivinphos, Terbufos, Tetrachlorvinphos, Thetacypermethrin, Thiapronil, Thiatriphos, Thiocyclam hydrogen oxalate, Thiodicarb, Thiofanox, Thuringiensin, Tralocythrin, Tralomethrin, Triarathene, Triazamate, Triazophos, Triazuron, Trichlophenidine, Trichlorfon, Triflumuron, Trimethacarb, Vamidothion, Vaniliprole, Verticillium lecanii,

YI 5302,

Zeta-cypermethrin, Zolaprofos, (1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetrameth ylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl) phenyl]-4,5-dihydro-oxazole, 2-(acetlyoxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-ditluorethioxv)-phenyl]-amino]-carbonyl]-benzamide, 3-methylphenyl propylcarbamate.

4-[4-(4-ethoxyphenyl)-4-methylpentyl]-1-fluoro-2-phenoxy-benzene, 4-chloro-2-(1,1-dimethylethyl)-5-[[2-(2,6-dinettiyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,

*Bacillus thuringiensis* strain EG-2348,

[2-benzoyl-1-(1,1-dimethylethyl)-hydrazinobenzoic acid, 2,2-dimethyl-3-(2,4-dichlorophenyl)-2-oxo-1-oxaspiro [4.5]dec-3-en-4-yl butanoate,

[3-[(6-chloro-3-pyridinyl)methyl]-2-thiazoldinylidene]-cyanamide, dihydro-2-(nitromethylene)-2H-1,3-thiazine-3(4H)-carboxaldehyde, ethyl [2-[[1,6-dihydro-6-oxo-1-(phenylmnethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitroguanidine, N-methyl-N'-(1-methyl-2-propenyl)-1,2-hydrazinedicarbothioamide, N-methyl-N'-2-propenyl-1,2-hydrazinedicarbothioamide, O,O-diethyl[2-(dipropylamino)-2-oxoethyl]-ethylphosphoramidothioate.

Herbicides:

for example anilides, such as, for example, diflufenican and propanil; arylcarboxylic acids such as, for example, dichloropicolinic acid, dicamba and picloram; aryloxyalkanoic acids, such as, for example, 2,4 D, 2,4 DB, 2,4 DP, fluroxypyr, MCPA, MCPP and triclopyr; aryloxyphenoxy-alkanoic acid esters, such as, for example, diclofop-methyl, fenoxaprop-ethyl, fluazifop-butyl, haloxyfop-methyl and quizalofop-ethyl; azinones, such as, for example, chloridazon and norflurazon; carbamates, such as, for example, chlorpropham, desmedipham, phenmedipham and propham; chloroacetanilides, such as, for example, alachlor, acetochlor, butachlor, metazachlor, metolachlor, pretilachlor and propachlor, dinitroanilines, such as, for example, oryzalin, pendimethalin and trifluralin; diphenyl ethers, such as, for example, acifluorfen, bifenox, fluoroglycofen, fomesafen, halosafen, lactofen and oxyfluorfen; ureas, such as, for example, chlortoluron, diuron, fluometuron, isoproturon, linuron and methabenzthiazuron; hydroxylamines, such as, for example, alloxydim, clethodim, cycloxydim, sethoxydim and tralkoxydim; imidazolinones, such as, for example, imazethapyr, imazamethabenz, imazapyr and imazaquin; nitriles, such as, for example, bromoxynil, dichlobenil and ioxynil; oxyacetamides, such as, for example, mefenacet; sulphonylureas, such as, for example, amidosulfuron, bensulfuron-methyl, chlorimuronethyl, chlorsulfuron, cinosulfuron, metsulfuron-methyl, nicosulfuron, primisulfuron, pyrazosulfuron-ethyl, thifensulfuron-methyl, triasulfuron and tribenuronmethyl; thiocarbamates, such as, for example, butylate, cycloate, di-allate, EPFC, esprocarb, molinate, prosulfocarb, thiobencarb and tri-allate; ttiazines, such as, for example, atrazine, cyanazine, simazine, simetryn, terbutryn and terbutylazine; triazinones, such as, for example, hexazinone, metamitron and metribuzin; others, Such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compound according to the invention can furthermore be present in its commercially available formulations and in the use forms, prepared from these formulations, as a mixture with synergistic agents. Synergistic agents are compounds which increase the action of the active compounds without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are used in a customary manner appropriate for the use form.

When used against hygiene pests and pests of stored products, the active compound has outstanding residual action on wood and clay and a stability to alkali on limed substrates.

The active compounds according to the invention are effective not only against plant and hygiene pests and pests of stored products, but also in the veterinary medicine sector against animal parasites (ectoparasites), such as hard ticks, soft ticks, mange mites, harvest mites, flies (biting and licking), parasitic fly larvae, lice, hair lice and fleas. These parasites include:

From the order of the Anoplurida, for example, Haematopinus spp., Linognathus spp., Pediculus spp., Phtirus spp. and Solenopotes spp.

From the order of the Mallophagida and the suborders Amblycerina and lschnocerina, for example, Trimenopon spp., Menopon spp., Trinoton spp., Bovicola spp., Wemeckiella spp., Lepikentron spp., Damalina spp., Trichodectes spp., Felicola spp.

From the order of the Diptera and the suborders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp, Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohifahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattrida, for example, Blatta orientalis, Periplaneta americana, Blattela germanica and Supella spp.

From the sub-class of the Acaria (Acarida) and the orders of the Meta- and Mesostigmata, for example, Argas spp., Omithodorus spp., Otabius spp., Ixodes spp., Amblyomma spp., Boophilus spp., Dermacentor spp., flaemaphysalis spp., Hyalomma spp., Rhipicephalus spp., Dermanyssus spp., Raillietia spp., Pneumonyssus spp., Stemostoma spp. and Varroa spp.

From the order of the Actinedida (Prostigmata) and Acaridida (Astig(mata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp, Psoroptes spp., Chorioptes spp., Otodectes spp., Sarcoptes spp., Notoedres spp., Knemidocoptes spp., Cytodites spp. and Laminosioptes spp.

For example, they show outstanding activity against *Boophilus microplus* and *Lucilia cuprina*.

The active compounds of the formula (I) according to the invention are also suitable for controlling arthropods which infest agricultural productive livestock such as, for example, cattle, sheep, goats, horses, pigs, donkeys, camels, buffalo, rabbits, chickens, turkeys, ducks, geese and bees, other pets, such as, for example, dogs, cats, cage birds and aquarium fish, and also so-called test animals, such as, for example, hamsters, guinea pigs, rats and mice. By controlling these arthropods mortality and reductions in productivity (for meat, milk, wool, hides, eggs, honey etc.) should be diminished, so that more economic and simple animal husbandry is possible by use of the active compounds according to the invention.

The active compounds according to the invention are used in the veterinary sector in a known manner by enteral administration in the form of, for example. tablets, capsules, potions, drenches, granules, pastes, boli, the feed-through process and suppositories, by parenteral administration, such as, for example, by injections (intra-muscular, subcutaneous, intravenous, intraperitoneal etc), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices, etc.

When used for livestock, poultry, pets and the like, the active compounds of the formula (I) can be used as formulations (for example powders, emulsions, flowables) which comprise the active compounds in an amount of 1 to 80% by weight, directly or after 100 to 10,000-fold dilution, or they can be used as a chemical bath.

It has furthermore been found that the compounds of the formula I according to the invention display high insecticidal action against insects which destroy industrial materials.

The following insects may be mentioned as examples and are preferred—but without being limited:

Beetles, such as

Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus spec., Tryptodendron spec., Apate monachus, Bostrychus capucins, Heterobostrychus brunneus, Sinoxylon spec. and Dinoderus minutus.

Hymenopterans, such as

Sirex juvencus, Urocerus gigas, Urocerus gigas taignus and Urocerus augur.

Termites, such as

Kalotermes flavicollis, Cryptotermes brevis, Heterotemies indicola, Reticulitermes flavipes, Reticulitermes santonensis, Reticuitermes lucifugus, Mastotemies darwiniensis, Zootermopsis nevadensis and Coptotermes fomnosanus.

Bristle-tails such as Lepisma saccharina.

Industrial materials in the present connection are to be understood as meaning non-living materials, such as, preferably, plastics, adhesives, sizes, papers and cards, leather, wood and processed wood products, and lacquers and paints.

Material to be preserved from insect damage which is quite particularly preferred is wood and processed wood products.

Wood and processed wood products which can be protected by the agents according to the invention or mixtures comprising these are to be understood as meaning, for example: building timber, wooden beams, railway sleepers, bridge components, boat gangplanks, wooden vehicles, crates, pallets, containers, telegraph masts, wood lagging, wooden windows and doors, plywood, chipboards, joinery or wood products used quite generally in house construction or building joinery.

The active compounds can be used as such or in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent anCdor binder or fixing agent, water repellant, optionally siccatives and UV stabilizers, and if appropriate dyestuffs and pigments, and also other processing auxiliaries.

The insecticidal compositions or concentrates used for preservation of wood and derived timber products comprise the active compound according to the invention in a concentration of 0.0001 to 95% by weight, in particular 0.001 to 60% by weight.

The amount of composition or concentrate employed depends on the nature and the occurrence of the insects and on the medium. The optimum amount employed for the use can in each case be determined by a series of tests. In general, however, it is sufficient to employ 0.0001 to 20% by weight, preferably 0.001 to 10% by weight, of the active compound based on the material to be preserved.

The solvent and/or diluent used is an organochemical solvent or solvent mixture and/or an oily or oil-like organochemical solvent or solvent mixture of low volatility and/or a polar organochemical solvent or solvent mixture and/or water and, if appropriate, an emulsifier and/or wetting agent.

Oily or oil-like solvents having an evaporation number above 35 and a flash point above 30° C., preferably above 45° C., are preferably employed as organochemical solvents. Corresponding mineral oils or aromatic fractions thereof or solvent mixtures containing mineral oil, preferably white spirit, petroleum and/or alkylbenzene, are used as such water-insoluble, oily and oil-like solvents of low volatility.

Mineral oils having a boiling range from 170 to 220° C., white spirit having a boiling range from 170 to 220° C., spindle oil having a boiling range from 250 to 350° C., petroleum or aromatics having a boiling range from 160 to 280° C., terpentine oil and the like are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably αl-monochloronaphthalene, are employed.

The organic oily or oil-like solvents of low volatility having an evaporation number above 35 and a flash point above 30° C., preferably above 45° C., can be replaced in part by organochemical solvents of high or medium volatility, provided that the solvent mixture likewise has an evaporation number above 35 and a flash point above 30° C., preferably above 45° C., and that the insecticide/fungicide mixture is soluble or can be emulsified in this solvent mixture.

According to a preferred embodiment, some of the organochemical solvent or solvent mixture is replaced by an aliphatic polar organochemical solvent or solvent mixture. Aliphatic organochemical solvents containing hiydroxyl and/or ester and/or ether groups, such as, for example, glycol ethers, esters or the like, are preferably used.

Organochemical binders which are the synthetic resins and/or binding drying oils which are water-dilutable and/or soluble or dispersible or emulsifiable in the organochemical solvents employed and are known per se, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-coumarone resin or silicone resin, drying plant and/or drying oils and/or binders which dry by physical means and are based on a naturally occurring and/or synthetic resin.

The synthetic resin used as the binder can be employed in the form of an emulsion, dispersion or solution. Bitumen or bituminous substances can also be used as binders in an amount of up to 10% by weight. In addition, dyestuffs, pigments, water-repellant agents, odour correctants and inhibitors or corrosion prevention agents and the like which are known per se can be employed.

Preferably, according to the invention, the composition or concentrate comprises at least one alkyd resin or modified alkyd resin and/or one drying plant oil as an organochemical binder. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether, or ketones, such as benzophenone or ethylenebenzophenone.

Water in particular is also a possible solvent or diluent, if appropriate mixed with one or more of the abovementioned organochemical solvents or diluents, emulsifiers and dispersing agents.

Particularly effective wood preservation is achieved by impregnation processes on a large industrial scale, for example vacuum, a double vacuum or pressure processes.

If appropriate, the ready-to-use compositions can also comprise other insecticides, and if appropriate also one or more fungicides.

Possible additional admixing partners are, preferably, the insecticides and fungicides mentioned in WO 94/29 268. The compounds mentioned in this document are an express constituent of the present application.

Especially preferred admixing partners can be insecticides, such as chlorpyriphos, phoxim, silafluofin, alphamethrin, cyfluthrin, cypermethrin, deltamethrin, permethfin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlofluanid, tolylfluanid, 3-iodo-2-propinyl butylcarbamate, N-octyl-isothiazolin-3-one and 4,5-dichloro-N-octylisothiazolin-3-one.

The preparation and the use of the active compounds according to the invention can be seen from the following examples.

The capital letters after some of the example numbers are meant to make identification of these structures in the formula schemes easier. They denote different meanings of Q.

EXAMPLES

Example I-1-a-1

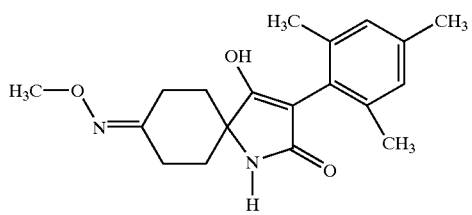

At 60° C., 7.2 g of the compound of Example IIC-1 in 10 ml of anhydrous DMF (dimethylformamide) are added to 7.8 g of potassium tert-butoxide in 20 ml of anhydrous DMF. Stirring is continued at this temperature until the reaction has ended (monitored by thin layer chromatography (TLC), mobile phase methylene chloride: ethyl acetate 5:3), the mixture is concentrated under reduced pressure and the residue is taken up in 100 ml of water and acidified at approximately 0° C. using 20% strength hydrochloric acid. The precipitate is filtered off with suction and dried.

Yield 4.0 g (61% of theory), mp. 250° C.

Example I-1-a-2

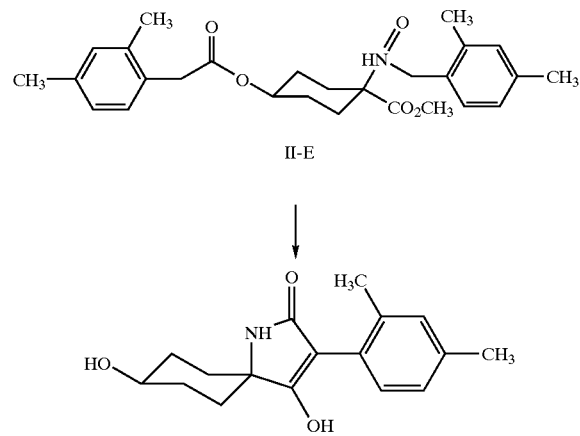

12 g of potassium tert-butoxide and 5.3 g of the compound II-E in 50 ml of DMF are stirred at 80° C. for 2 hours. The mixture is mixed with toluene and concentrated under reduced pressure. The residue is taken up in 30 ml of ice-water and admixed at approximately 0° C. with 20% strength hydrochloric acid until the pH is approximately between 5 and 6. The mixture is filtered off with suction and purified by column chromatography (silica gel, methylene chloride/ethyl acetate 5/3). Yield 1.15 g (36% of theory), mp. 163° C.

Example I-1-a-3

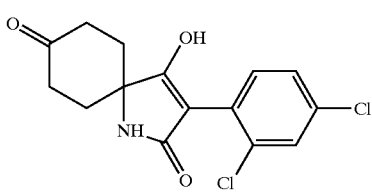

II-B-2

Similarly, starting from the compound of Example II-B-2, the compound depicted above of mp. >250° C. is obtained.

Example I-1-a-4

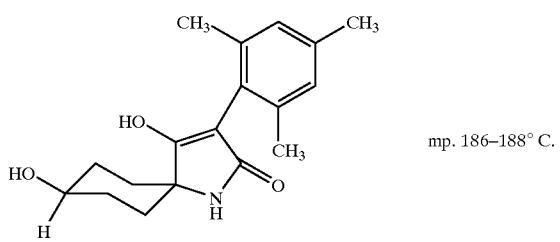

mp. 186–188° C.

The compounds of the formula (I-1-a) listed in Table 25 below are likewise prepared by the methods described above.

TABLE 25

(I-1-a)

| Ex. No. | X | Y | $Z_n$ | Q | m | melting point in ° C. |
|---|---|---|---|---|---|---|
| I-1-a-5 | CH₃ | H | 5-CH₃ | —CH(OH)— | 1 | 143 |
| I-1-a-6 | CH₃ | CH₃ | 3,6-(CH₃)₂ | —CH(OH)— | 1 | >250 |
| I-1-a-7 | CH₃ | H | 5-CH₃ | —C(=O)— | 1 | |
| I-1-a-8 | CH₃ | CH₃ | 3,6-(CH₃)₂ | —C(=O)— | 1 | |

Example I-1-b-1

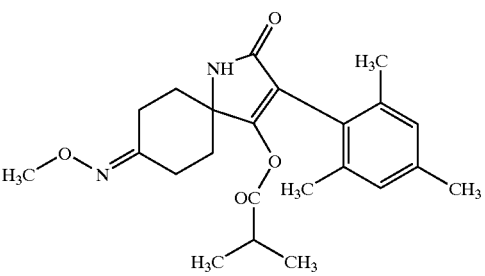

2 g of the compound of Example I-1-a-1 are heated under reflux with 1.1 ml of triethylamine and 0.75 g of iso-butyryl chloride in 50 ml of ethyl acetate for 4 hours. The mixture is concentrated and the residue is chromatographed over silica gel (mobile phase hexane:acetone 7:3).

Yield 1.15 g (48% of theory), mp. 247° C.

Example I-1-b-2

By the method of Example I-1-b-1, the compound below of mp. 189° C. is obtained.

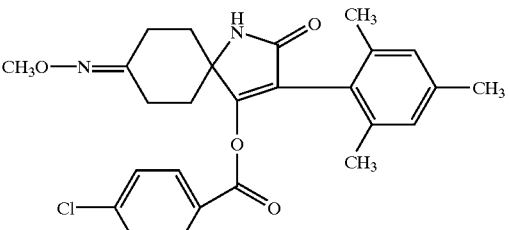

Example I-1-c-1

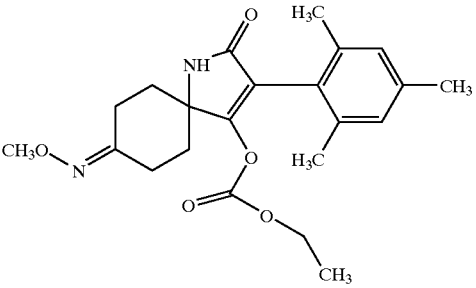

At 0° C., 0.4 ml of ethyl chloroformate in 5 ml of anhydrous methylene chloride are added dropwise to 1.3 g of the compound of Example (I-1-a-1) and 0.6 ml of triethylamine in 50 ml of anhydrous methylene chloride, and the mixture is stirred for one more day without cooling. The mixture is then washed twice with 50 ml of 0.5 N NaOH each time, dried and concentrated. Yield 0.70 g (45% of theory), mp. 196° C.

Example I-2-a-1

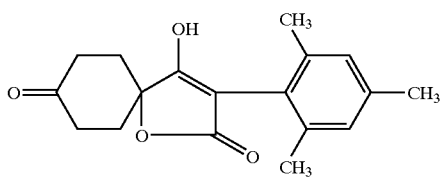

A solution of 34.6 g of the compound of Example III-A-1 is added dropwise to 11.22 g of potassium tert-butoxide in 100 ml of anhydrous DMF, and the mixture is stirred at room temperature overnight. For work-up, the reaction mixture is added dropwise to 1 l of 1N HCl, extracted with methylene chloride, dried and concentrated. The residue is chromatographed over silica gel using ethyl acetate.

Yield 5.5 g (18% of theory), mp. 190–195° C.

Example I-2-a-2

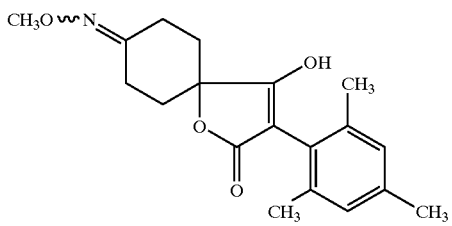

At 0 to 10° C., 15 g of the compound of Example III-2 dissolved in 15 ml of DMF are added dropwise to 6.72 g of potassium tert-butoxide in 5 ml of DMF. The mixture is stirred overnight at room temperature and concentrated and the residue is taken up in water and acidified with HCl while cooling with ice. The precipitate is filtered off with suction and dried.

Yield 10.9 g (62% of theory), mp. 74–80° C.

By the methods of Examples I-2-a-1 and I-2-a-2 and/or according to the general preparation procedures, the following compounds of the formula I-2-a are obtained:

TABLE 26

(I-2-a)

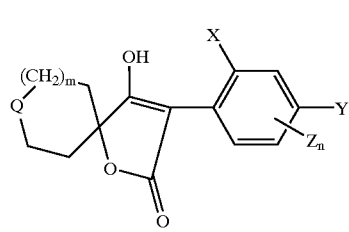

| Ex. No. | X | Y | $Z_n$ | Q | m | mp. in ° C. |
|---|---|---|---|---|---|---|
| I-2-a-3 | $CH_3$ | Cl | 6-Br | —C(=N—OCH$_3$)— | 1 | 130 |
| I-2-a-4 | $CH_3$ | Br | 6-Cl | —C(=N—OCH$_3$)— | 1 | 147 |

TABLE 26-continued (I-2-a)

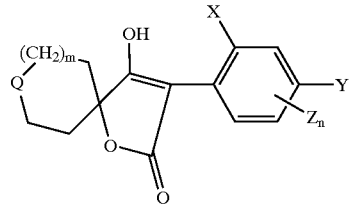

| Ex. No. | X | Y | $Z_n$ | Q | m | mp. in ° C. |
|---|---|---|---|---|---|---|
| I-2-a-5 | Cl | $CH_3$ | 6-Cl | —C(=N—OCH$_3$)— | 1 | 192 |
| I-2-a-6 | $CH_3$ | $CH_3$ | 3,6-$(CH_3)_2$ | —C(=N—OCH$_3$)— | 1 | 88 |
| I-2-a-7 | Cl | $CH_3$ | 6-Br | —C(=N—OCH$_3$)— | 1 | 190 |
| I-2-a-8 | Br | $CH_3$ | 6-Br | —C(=N—OCH$_3$)— | 1 | 138 |
| I-2-a-9 | $CH_3$ | Br | 6-Br | —C(=N—OCH$_3$)— | 1 | 146 |
| I-2-a-10 | $CH_3$ | Cl | 6-$CH_3$ | —C(=N—OCH$_3$)— | 1 | 125–127 |

Example I-2-a-11

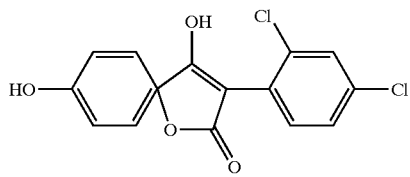

At room temperature, 9.3 g of the compound of Example (III-C-1) are added dropwise to 6.5 g of potassium tert-butoxide in 40 ml of DMF (dimethylformamide), the reaction mixture warming up. Stirring is continued at room temperature for one day and the reaction mixture is then admixed with water and extracted with methylene chloride. The aqueous phase is acidified (pH 2–3) using HCl and extracted with methylene chloride. The organic phase is concentrated, Yield 3.40 g (68% of theory). mp. 272° C.

The compounds of the formula (I-2-a) listed in Table 27 below are likewise prepared by the methods described above.

TABLE 27

(I-2-a)

| Ex. No. | X | Y | $Z_n$ | Q | m | mp in °C. |
|---|---|---|---|---|---|---|
| I-2-a-12 | $CH_3$ | H | 5-$CH_3$ | —C(=N—$OCH_3$)— | 1 | 178–180 |
| I-2-a-13 | $CH_3$ | $CH_3$ | 5-$CH_3$ | —C(=N—$OCH_3$)— | 1 | 185–187 |
| I-2-a-14 | $CH_3$ | $CH_3$ | 6-$CH_3$ | —C(=N—$OC_2H_5$)— | 1 | 182–185 |
| I-2-a-15 | $CH_3$ | $CH_3$ | 6-$CH_3$ | —C(=N—O—$CH_2$—CH=$CH_2$)— | 1 | 164–168 |
| I-2-a-16 | $CH_3$ | $CH_3$ | 6-$CH_3$ | —C(=N—O—$C(CH_3)_3$)— | 1 | 212 |
| I-2-a-17 | $CH_3$ | $CH_3$ | 6-$CH_3$ | —C(=N—$CH_2$—$C_6H_5$)— | 1 | oil |

Example I-2-b-1

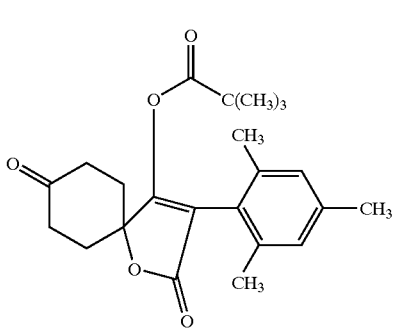

Examnle I-2-b-2

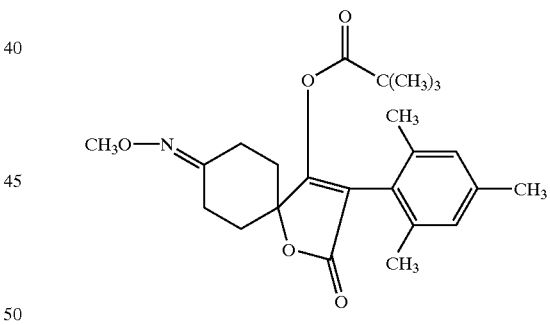

At 0 to 10° C., 1.24 g of pivaloyl chloride dissolved in 10 ml of methylene chloride are added dropwise to 3.00 g of the compound of Example I-2-a-1 and 1.52 ml of triethylamine in 40 ml of methylene chloride, and the mixture is stirred at room temperature overnight. The reaction mixture is washed successively with 10 ml of 10% strength citric acid solution, $NaHCO_3$-solution and NaCl-solution dried and concentrated. The residue is chromatographed over silica gel using cyclohexane: ethyl acetate 3:1 as mobile phase.

Yield 1.79 g (47% of theory), mp. 133–136° C.

At room temperature, 0.96 g of the compounid of Example I-2-b-1, 0.25 g of O-methylhydroxylamine hydrochloride and 1 g of molecular sieve 3 Å are stirred in 15 ml of methanol for 12 hours. The molecular sieve is filtered off, the filtrate is concentrated, the residue is partitioned between water and methylene chloride and the organic phase is dried and concentrated under reduced pressure. The residue is chromatographed over silica gel using cyclohexane:ethyl acetate 5:1.

Yield 0.39 g (39% of theory), mp. 115–127° C.

By the method of Examples I-2-b-1 and I-2-b-2 and/or according to the general preparation procedures, the following compounds of the formula I-2-b are obtained:

TABLE 28

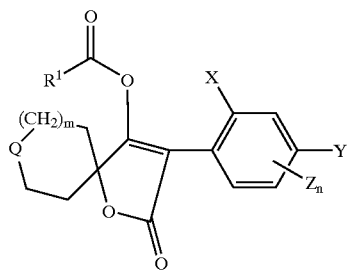

(I-2-b)

| Ex. No. | X | Y | $Z_n$ | Q | m | $R^1$ | mp. in ° C. |
|---|---|---|---|---|---|---|---|
| I-2-b-3 | CH$_3$ | CH$_3$ | 6-CH$_3$ | —C(=N—OCH$_3$)— | 1 | Cl—CH$_2$—C(CH$_3$)$_2$— | oil |
| I-2-b-4 | CH$_3$ | CH$_3$ | 6-CH$_3$ | —C(=N—OCH$_3$)— | 1 | t-C$_4$H$_9$—CH$_2$— | semi-crystalline |
| I-2-b-5 | CH$_3$ | CH$_3$ | 6-CH$_3$ | —C(=N—OCH$_3$)— | 1 | C$_4$H$_9$—CH(C$_2$H$_5$)— | oil |
| I-2-b-6 | Br | Cl | 6-CH$_3$ | —C(=N—OCH$_3$)— | 1 | i-C$_3$H$_7$— | oil |
| I-2-b-7 | Cl | Br | 6-CH$_3$ | —C(=N—OCH$_3$)— | 1 | i-C$_3$H$_7$— | oil |
| I-2-b-8 | Cl | CH$_3$ | 6-Cl | —C(=N—OCH$_3$)— | 1 | i-C$_3$H$_7$— | 134–135 |
| I-2-b-9 | CH$_3$ | CH$_3$ | 3,6(CH$_3$)$_2$ | —C(=N—OCH$_3$)— | 1 | i-C$_3$H$_7$— | oil |
| I-2-b-10 | Cl | CH$_3$ | 6-Br | —C(=N—OCH$_3$)— | 1 | i-C$_3$H$_7$— | 130–131 |
| I-2-b-11 | Br | CH$_3$ | 6-Br | —C(=N—OCH$_3$)— | 1 | i-C$_3$H$_7$— | 124–125 |
| I-2-b-12 | CH$_3$ | Br | 6-Br | —C(=N—OCH$_3$)— | 1 | i-C$_3$H$_7$— | 98–100 |
| I-2-b-13 | CH$_3$ | Cl | 6-CH$_3$ | —C(=N—OCH$_3$)— | 1 | i-C$_3$H$_7$— | oil |
| I-2-b-14 | CH$_3$ | CH$_3$ | 6-CH$_3$ | —CO— | 1 | CH$_3$— | 209–210 |
| I-2-b-15 | CH$_3$ | CH$_3$ | 6-CH$_3$ | —C(=N—OH)— | 1 | t-C$_4$H$_9$ | |
| I-2-b-16 | CH$_3$ | H | 5-CH$_3$ | —C(=N—OCH$_3$)— | 1 | i-C$_3$H$_7$— | oil |
| I-2-b-17 | CH$_3$ | CH$_3$ | 5-CH$_3$ | —C(=N—OCH$_3$)— | 1 | i-C$_3$H$_7$— | oil |

Example I-2-c-1

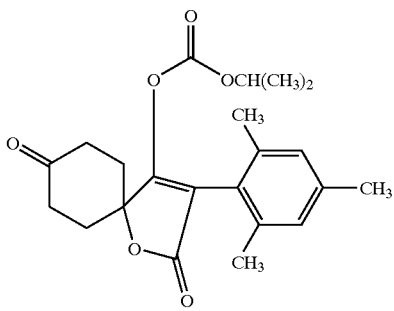

By the method of Example I-2-b-1, the compound depicted above is obtained in a yield of 46% of theory if isopropyl chloroformnate is used instead of pivaloyl chloride. mp. 140–141° C.

Example I-2-c-2

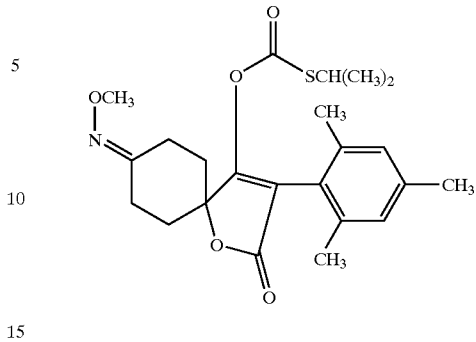

By the method of Example I-2-b-1, the compound depicted above is obtained as an oil in a yield of 1.3 g if isopropyl chlorothioformate is used instead of pivaloyl chloride.

By the methods of Examples I-2-c-1 and I-2-c-2 and/or according to the general preparation procedures, the following compounds of the formula I-2-c are obtained:

TABLE 29

(I-2-c)

| Ex. No. | X | Y | $Z_n$ | Q | m | M | $R^2$ | mp. in ° C. |
|---|---|---|---|---|---|---|---|---|
| I-2-c-3 | Br | Cl | 6-$CH_3$ | —C(=N—$OCH_3$)— | 1 | O | i-$C_4H_9$— | oil |
| I-2-c-4 | Cl | Br | 6-$CH_3$ | —C(=N—$OCH_3$)— | 1 | O | i-$C_4H_9$— | oil |
| I-2-c-5 | Cl | $CH_3$ | 6-Cl | —C(=N—$OCH_3$)— | 1 | O | i-$C_4H_9$— | oil |
| I-2-c-6 | $CH_3$ | $CH_3$ | 3,6-$(CH_3)_2$ | —C(=N—$OCH_3$)— | 1 | O | i-$C_4H_9$— | oil |
| I-2-c-7 | $CH_3$ | Br | 6-Br | —C(=N—$OCH_3$)— | 1 | O | i-$C_4H_9$— | 98–100 |
| I-2-c-8 | $CH_3$ | Cl | 6-$CH_3$ | —C(=N—$OCH_3$)— | 1 | O | i-$C_4H_9$— | oil |
| I-2-c-9 | $CH_3$ | $CH_3$ | 6-$CH_3$ | —CO— | 1 | O | $CH_3$— | 153–154 |

Example II-B-1

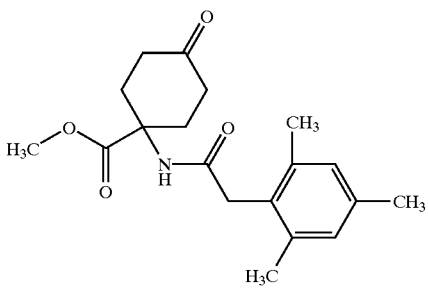

At an internal temperature of 30 to 40° C., a suspension of 50 g of the compound of Example XX-C-1 is added dropwise to 75 g of concentrated sulphuric acid, and the mixture is stirred for another 2 hours at this temperature. 110 ml of methanol are then added dropwise in such a way that an internal temperature of 40° C. results. Stirring is subsequently continued at 40 to 70° C. for a further 6 hours. The mixture is poured onto 600 g of ice, admixed with aqueous NaHCO$_3$-solution and extracted with methylene chloride.

Yield 40 g (74% of theory), mp. 136–137° C.

Example II-B-2

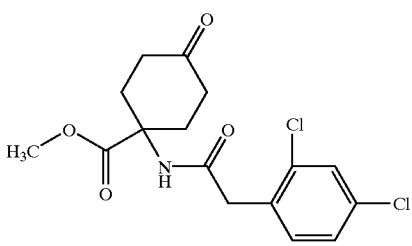

By the method of Example II-B-1, 11.7 g (15% of theory) of the compound depicted above are obtained from 69 g of the compound of Example XX-B-1.

mp. 118–120° C.

Example II-C-1

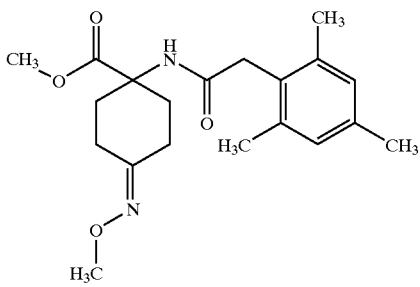

At room temperature, 20 g of the compound of Example II-B-1 in 50 ml of pyridine are mixed with 4.2 g of O-methylhydroxylamine hydrochloride, and the mixtures were stirred at 50° C. for 4 hours. The mixture is concentrated under reduced pressure and the residue is mixed with approximately 50 ml of water and extracted 3 times with methylene chloride. The combined organic phases are dried and concentrated. The residue is chromatographed over silica gel using methylene chloride:ethyl acetate 5:3.

Yield 19.9 g (99% of theory), mp. 158–160° C.

Example II-E-1

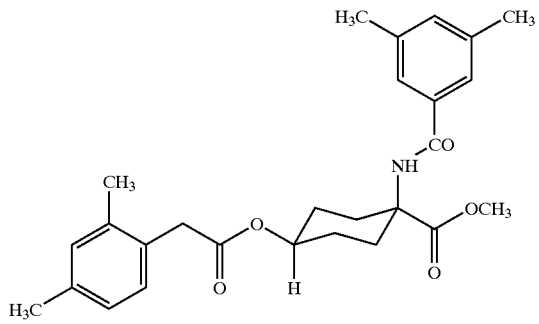

At −10 to 0° C., 32 g of the compound of the formula (XV)

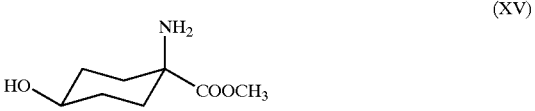

(XV)

and 57 ml of triethylamine in 200 ml of tetrahydrofuran are admixed with 34 g of 2,4-dimethylphenyl acetyl chloride, and the mixture is stirred at room temperature for 1 day. The mixture is filtered off with suction and the filtrate is concentrated. The residue is chromatographed over silica gel. Yield 5.3 g.

$^1$H NMR (400 MHz, d$_6$-DMSO): δ=2.19–2.25 (4s, 12H, Ar CH$_3$), 4.63–4.69, 4.82–4.86 (m, 1H, CO—O—CH), 6.9–7.06 (m, 6H, Ar—H)

Example III-1

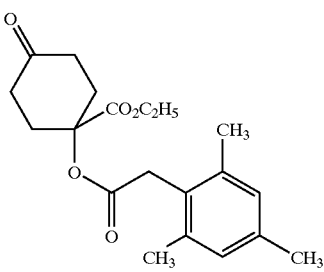

29.55 g of 2,4,6-trimethylphenylacetyl chloride are added to 27.90 g of ethyl 1-hydroxy-4-oxo-cyclohexanecarboxylate in 150 ml of toluene, and the mixture is heated under reflux overnight. The mixture is then concentrated under reduced pressure and the crude product is used for the cyclocondensation reaction without any further purification.

Yield 42.9 g (82% of theory), oil.

Example III-2

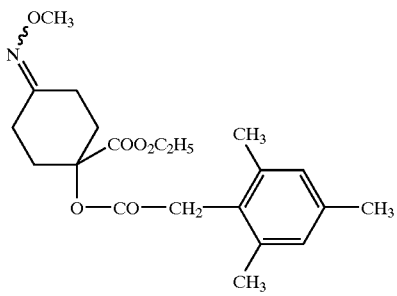

At 0 to 10° C., 9.14 g of 2,4,6-trimethylphenylacetyl chloride are added dropwise to 10 g of the compound of Example XXI-3 and 5.6 g of triethylamine in 100 ml of methylene chloride, and the mixture is stirred at room temperature overnight. The mixture is then washed with water and the organic phase is dried and concentrated.

Yield 15.14 g, oil.

By the methods of Examples III-1 and III-2 and/or according to the general preparation procedures, the following compounds of the formula III are obtained:

TABLE 30

(III)

| Ex. No. | X | Y | $Z_n$ | Q | m | $R^8$ | mp. in °C. |
|---|---|---|---|---|---|---|---|
| III-3 | $CH_3$ | Cl | 6-Br | —C(=N—OCH₃)— | 1 | $C_2H_5$ | oil |
| III-4 | $CH_3$ | Br | 6-Cl | —C(=N—OCH₃)— | 1 | $C_2H_5$ | oil |
| III-5 | Cl | $CH_3$ | 6-Cl | —C(=N—OCH₃)— | 1 | $C_2H_5$ | oil |
| III-6 | $CH_3$ | $CH_3$ | 3,6-$(CH_3)_2$ | —C(=N—OCH₃)— | 1 | $C_2H_5$ | oil |
| III-7 | Cl | $CH_3$ | 6-Br | —C(=N—OCH₃)— | 1 | $C_2H_5$ | oil |
| III-8 | Br | $CH_3$ | 6-Br | —C(=N—OCH₃)— | 1 | $C_2H_5$ | oil |
| III-9 | $CH_3$ | Br | 6-Br | —C(=N—OCH₃)— | 1 | $C_2H_5$ | oil |
| III-10 | $CH_3$ | Cl | 6-$CH_3$ | —C(=N—OCH₃)— | 1 | $C_2H_5$ | oil |

Example III-C-1

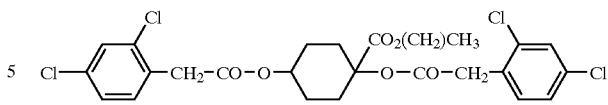

At room temperature, 11 g of the compound of Example (XXI-2) in 200 ml of toluene are mixed with 40 g of 2,4-dichlorophenylacetyl chloride (3.5 eq.), and the mixture is heated under reflux for one day. The mixture is concentrated and the residue is chromatographed over silica gel using hexane/ethyl acetate 2/1. mp. 57° C.

Example XIX-1

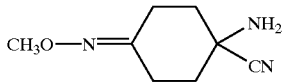

At room temperature, 248.3 g of 4-hydroxycyclohexanone are added dropwise to a mixture of 414.2 g of 25% strength ammonia solution, 139.6 g of ammonium chloride, 127.9 g of sodium cyanide and 392 ml of water, and the mixture is stirred at 45° C. overnight. The precipitate is filtered off with suction and dried.

Yield 197 g (64% of theory), mp. 130° C.

Example XIX-2

At room temperature, 36.0 g of the compound of Example XXV-1 are added dropwise to a mixture of 48.5 g of 25% strength ammonia solution, 16.4 g of ammonium chloride and 15.0 g of sodium cyanide in 46 ml of water, and the mixture is stirred at 38° C. overnight. Extraction with methylene chloride and customary work-up gives 33.8 g (79% of theory) of the compound depicted above as an oil.

Example XX-A-1

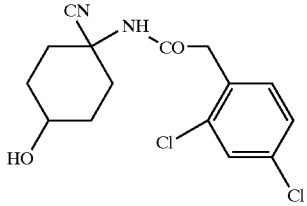

At -20° C., 79 g of 2,4-dichlorophenyl acetyl chloride in 50 ml of THF are added to 49 g of 1-cyano-4-hydroxycyclohexylamine of Example XIX-1 and 49 ml of triethylaamine in 500 ml of THF. The mixture is stirred at room temperature for 1 day and extracted with 1 l of 0.5 N HCl, and the organic phase is dried and concentrated.

Yield 70 g (61% of theory), mp. 148–150° C.

Example XX-B-1

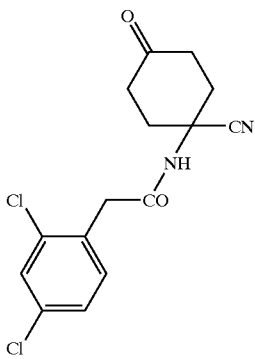

70 g of the compound of Example XX-A-1 are oxidized by the method of Example XXV-1.

Yield 69.0 g (99% of theory), mp. 76–78° C.

Example XX-C-1

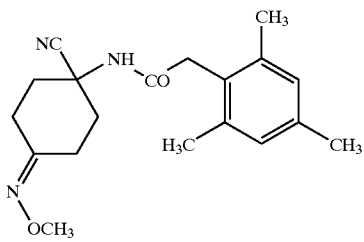

At approximately 0° C., 40 g of 2,4,6-trimethylphenylacetyl chloride in 50 ml of THF (tetrahydrofuran) are added to 33 g of the compound of Example XIX-1 and 32 ml of triethylamine in 100 ml of THF, and the mixture is stirred at room temperature of 2 hours. For work-up, the reaction mixture is shaken with 1 l of 1N NaOH and the organic phase is separated off, dried and concentrated.

Yield 52 g (79% of theory), mp. 224° C.

Example XXI-1

At room temperature, 28.7 ml of hydrogen cyanide are added dropwise to 102.0 g of cyclohexanedione 1,4-monoethylene glycol (commercially available) and 0.6 ml of triethylamine in 102 ml of ethanol, and the mixture is stirred at room temperature for 1 hour. The mixture is admixed with 229 ml of ethanol, saturated with HCl gas at 0 to 5° C. and stirred overnight at room temperature. The mixture is then concentrated under reduced pressure and the residue is stirred in 980 ml of water at room temperature overnight. The mixture is extracted with methylene chloride and the organic phase is washed with saturated $K_2CO_3$-solution, dried and concentrated.

Yield 68.3 g (50% of theory), oil.

Example XXI-2

At −20 to 0° C., approximately 1 kg of the compound of Example XXX-1 in 5 l of n-butanol is saturated with HCl gas. The mixture is stirred at 0° C. for approximately 3 hours and then without cooling overnight.

A vacuum is applied and the residue is mixed with approximately 5 l of water and stirred at room temperature for 1 hour. The mixture is extracted with 2.5 l of methylene chloride, dried and concentrated.

Yield 1376 g (81% of theory), yellow oil.

Example XXI-3

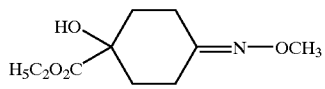

1.86 g of compound of Example XXI-1 and 0.88 g of O-methylhydroxylamine hydrochloride in 20 ml of pyridine are stirred at 50° C. overnight. The mixture is concentrated under reduced pressure, the residue is taken up in water and methylene chloride and washed with 10% strength citric acid and the organic phase is dried and concentrated.

Yield 1.7 g oil.

Example XXV-1

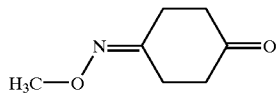

At −70° C., 11 ml of oxalyl chloride are initially charged in 300 ml of methylene chloride. 10 ml of DMSO (dimethyl sulphoxide) are added and the mixture is stirred at −35° C. for 3 minutes. The mixture is once more cooled to −70° C., and 150 g of the compound of Example XXVI-1 are added, as a 10% strength solution in methylene chloride, over a period of 1 hour. Stirring is continued at −35° C. for a further 15 minutes, 130 ml of triethylamine are added and the mixture is then stirred at room temperature for 1 hour. The mixture is carefully admixed with water, extracted with methylene chloride and filtered through silica gel.

Yield 7.9 g (56% of theory), oil.

Example XXVI-1

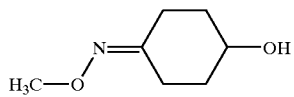

At room temperature, 5.7 g of 4-hydroxycyclohexanone in 50 ml of pyridine are mixed with 4.2 g of O-methylhydroxylamine hydrochloride, and the mixture is stirred at 50° C. for 4 hours. The mixture is concentrated under reduced pressure and the residue is taken up in approximately 50 ml of water and extracted three times with methylene chloride. The combined organic phases are dried and concentrated.

Yield 6.9 g (96% of theory), oil.

Example XXVII-1

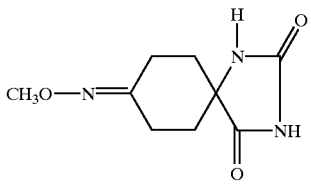

A solution of 70.5 g of the compound of Example XXV-1 in 1600 ml of ethanol is added to 446.4 g of ammonium carbonate and 98.0 g of sodium cyanide in 1600 ml of water, and the mixture is stirred at 60° C. for 10 hours. The mixture is then cooled to 5° C. and the precipitate is filtered off with suction.

Yield 156.7 g (74% of theory), mp. >250° C.

Example XXX-1

At room temperature, 249.5 g of hydrogen cyanide are added dropwise over a period of approximately 45 minutes to 1004.4 g of 4-hydroxycyclohexanone and 3.70 ml of triethylamine, and the mixture is stirred at 65° C. for approximately 1 hour.

The mixture is stabilized with 0.6 ml of 85% strength o-phosphoric acid and dried under water pump vacuum. The crude product is converted into the compounds of the formula (XXI) without any further purification.

USE EXAMPLES

Example A

Myzus-Test

Solvent: 7 parts by weight dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*), which are heavily infested by peach affids (*Myzus persicae*) are treated by being dipped into the preparation of active compound of the desired concentration.

After the desired period of time, the kill in per cent is determined. 100% means that all affids have been killed; 0% means that none of the affids have been killed.

In this test, for example, the compounds of preparation examples I-2-b-2, I-2-c-2, I-2-b-3, I-2-b-4, I-2-a-8, I-2-a-9, I-2-b-8, I-2-c-5, I-2-b-9, I-2-b-12, I-2-c-7, I-1-a-1 and I-1-b-1 effected, at an exemplary active compound concentration of 0.1%, the kill of in each case 100% after 6 days.

Example B

Nephotettix-Test

Solvent: 7 parts by weight dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and populated with larvae of the green rice leaf hoppers (*Nepliotettix cincticeps*) while the seedlings are still moist.

After the desired period of time, the kill in % is determined. 100% means that all leaf hoppers have been killed, 0% means that none of the leaf hoppers have been killed.

In this test, for example, the compounds of preparation examples I-2-a-2, I-2-b-3, I-2-b-4, I-2-b-5, I-2-c-2, I-2-a-5, I-2-a-6, I-2-c-3, I-2-b-7, I-2-c-4, I-2-a-7, I-2-a-9, I-2-b-9, I-2-c-6, I-1-a-1 and I-1-b-1 effected, at an exemplary active compound concentration of 0.1%, a kill of in each case 100% after 6 days.

Example C

Panonychus-Test

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with emulsifier-containing water to the desired concentration.

Plum trees (*Prunus domestica*), of a height of approximately 30 cm which are heavily infested by all development stages of the fruit tree red spider mite (*Panonychus ulmi*) are sprayed with a preparation of active compound of the desired concentration.

After the desired period of time, the effect in % is determined. 100% means that all spider mites have been killed, 0% means that none of the spider mites have been killed.

In this test, for example, the compound of preparation example I-2-b-2 showed, at an exemplary active compound concentration of 0.02%, an effect of 100% after 7 days.

Example D

Phaedon-Larvae-Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and populated with larvae of the mustard beetle (*Phaedon cochleariae*) while the leaves are still moist.

After the desired period of time, the kill in % was determined. 100% means that all beetle larvae have been killed, 0% means that none of the beetle larvae have been killed.

In this test, for example, the compounds of preparation examples I-2-b-2, I-2-b-3, I-2-c-2, I-2-c-6, I-1-a-1 and I-1-b-1 effected, at an exemplary active compound concentration of 0.1%, a kill of in each case 100% after 7 days.

Example E

*Spodoptera Frugiperda*-Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and populated with caterpillars of the owlet moth (*Spodoptera frugiperda*) while the leaves are still moist.

After the desired period of time, the kill in % is determined. 100%, means that all caterpillars have been killed; 0% means that none of the caterpillars have been killed.

In this test, for example, the compounds of preparation examples I-2-b-2, I-2-b-3, I-2-c-2, I-2-c-5, I-1-a-1 and I-1-b-1 effected, at an exemplary active compound concentration of 0.1%, a kill of in each case 100% after 7 days.

Example F

Tetranychus-Test (OP-resistant/dipped Treatment)

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*), which are heavily infested by all stages of the greenhouse spider mite (*Tetranychus urticae*) are dipped into a preparation of active compound of the desired concentration.

After the desired period of time, the activity in % is determined. 100% means that all spider mites have been killed, 0% means that none of the spider mites have been killed.

In this test, for example, the compounds of preparation examples I-2-b-2, I-2-a-2, I-2-b-3, I-2-b-4, I-2-b-5, I-2-c-2, I-2-c-3, I-2-c-5, I-2-b-9, I-2-c-6, I-2-b-10, I-2-b-11 and I-1-b-1 effected, at an exemplary active compound concentration of 0.01%, in each case a kill of 100% after 7 days.

Example G

Test with *Boophilus microplus* resistant/SP-resistant Parkhurst-strain

Test animals: adult females which have sucked themselves full

Solvent: dimethyl sulphoxide 20 mg of active compound are dissolved in 1 ml of dimethyl sulphoxide, more dilute concentrations are prepared by dilution with the same solvent.

The test is carried out in 5 replications. 1 µl of the solution is injected into the abdomen, and the animals are transferred into dishes and kept in a climatized room. The activity is determined after 7 days via the inhibition of oviposition. 100% means that no tick has deposited eggs.

In this test, for example, the compounds of preparation examples I-1-a-1 and I-1-b-1 had, at an exemplary active compound concentration of 20 µg/animal, in each case an activity of 100%.

Example H

Blowfly-Larvae-Test/Development-inhibitory Action

Test animals: Lucilia cuprina-Larvae

Solvent: dimethyl sulphoxide 20 mg of active compound are dissolved in 1 ml of dimethyl sulphoxide, more dilute concentrations are prepared by dilution with distilled $H_2O$.

Approximately 20 *Lucilia cuprina* larvae are introduced into a test tube which contains approximately 1 $cm^3$ of horse meat and 0.5 ml of the preparation of active compound to be tested. After 24 and 48 hours, the efficacy of the preparation of active compound is determined. The test tubes are transferred into beakers whose bottom is covered with sand. After a further 2 days, the test tubes are removed, and the pupae are counted.

The activity of the preparation of active compound is assessed by the number of flies which have emerged after 1.5 times the development time of an untreated control. 100% means that no flies have emerged; 0% means that all the flies have emerged normally.

In this test, for example, the compounds of preparation examples I-2-b-2 and I-1-a-1 had, at an exemplary active compound concentration of 1000 ppm, in each case an activity of 100%.

What is claimed is:

1. A compound of the formula (I)

in which

X represents halogen, $C_1$–$C_6$-alkyl, $C_2$–$C_6$-alkenyl, $C_2$–$C_6$-alkinyl, $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkyl, $C_2$–$C_6$-halogenoalkenyl, $C_1$–$C_6$-halogenoalkoxy, $C_3$–$C_6$-halogenoalkenyloxy, nitro, cyano or represents phenyl, phenoxy, phenylthio, benzyloxy or benzylthio, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, Y represents hydrogen, halogen, $C_1$–$C_6$-alkyl, $C_2$–$C_6$-alkenyl, $C_2$–$C_6$-alkinyl, $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkyl, $C_2$–$C_6$-halogenoalkenyl, $C_1$–$C_6$-halogenoalkoxy, $C_3$–$C_6$-halogenoalkenyloxy, nitro or cyano, Z represents halogen, $C_1$–$C_6$-alkyl, $C_2$–$C_6$-alkenyl, $C_2$–$C_6$-alkinyl, $C_1$–$C_6$-halogenoalkyl, $C_2$–$C_6$-halogenoalkenyl, $C_1$–$C_6$-alkoxy, $C_3$–$C_6$-alkenyloxy, $C_1$–$C_6$-halogenoalkoxy, $C_3$–$C_6$-halogenoalkenyloxy, nitro or cyano, n represents 0, 1, 2 or 3, Het represents one of the groups

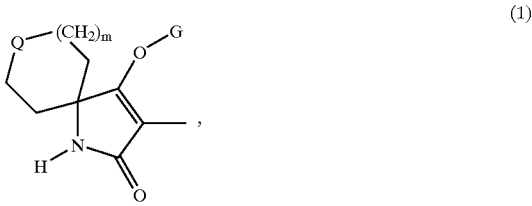

-continued

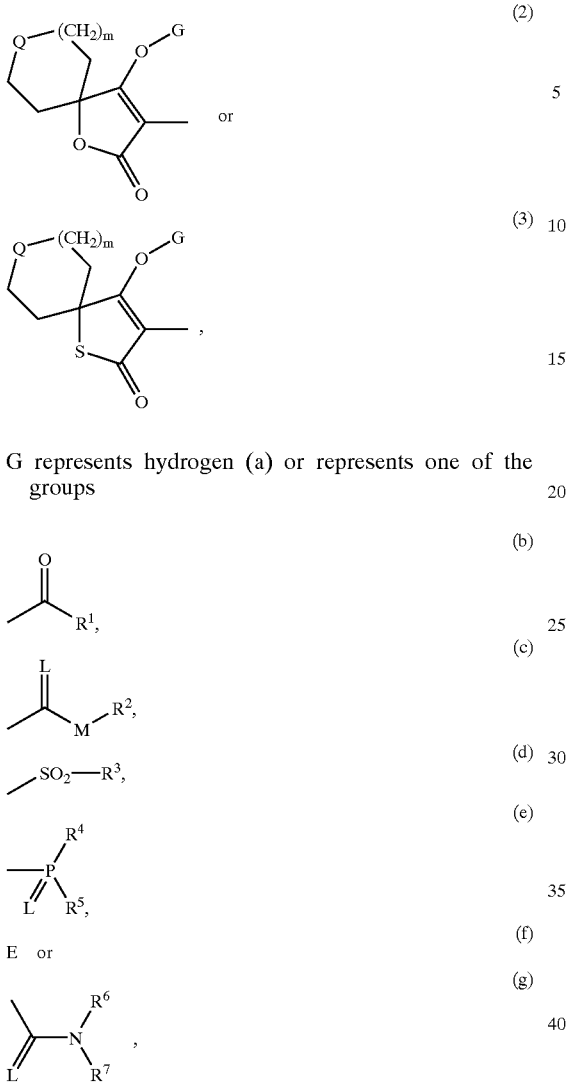

G represents hydrogen (a) or represents one of the groups

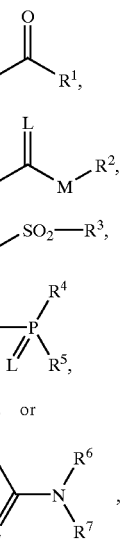

in which
E represents a metal ion equivalent or an ammonium ion,
L represents oxygen or sulphur and
M represents oxygen or sulphur,
$R^1$ represents $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl, each of which may optionally be substituted with halogen, represents $C_3$–$C_8$-cycloalkyl which may optionally be substituted by halogen, $C_1$–$C_6$-alkyl or $C_1$–$C_6$-alkoxy and in which optionally one or at most two not directly adjacent methylene groups may be replaced by oxygen and/or sulphur,
represents phenyl which is optionally substituted by halogen, cyano, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio or $C_1$–$C_6$-alkylsulphonyl,
represents phenyl-$C_1$–$C_6$-alkyl, which is optionally substituted by halogen, nitro, cyano, $C_1$–$C_6$-alkyl, $C_1$–$C_6$-alkoxy, $C_1$–$C_6$-halogenoalkyl or $C_1$–$C_6$-halogenoalkoxy,
represents 5- or 6-membered hetaryl selected from pyrazolyl, thiazolyl, pyridyl, pyrimidyl, furanyl and thienyl each of which is optionally substituted by halogen or $C_1$–$C_6$-alkyl,
represents phenoxy-$C_1$–$C_6$-alkyl which is optionally substituted by halogen or $C_1$–$C_6$-alkyl or
represents 5- or 6-membered hetaryloxy-$C_1$–$C_6$-alkyl which is optionally substituted by halogen, amino or $C_1$–$C_6$-alkyl,
$R^2$ represents $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, each of which is optionally substituted by halogen,
represents $C_3$–$C_8$-cycloalkyl which is optionally substituted by halogen, $C_1$–$C_6$-alkyl or $C_1$–$C_6$-alkoxy or
represents phenyl or benzyl, each of which is optionally substituted by halogen, cyano, nitro, $C_1$–$C_6$-alkyl, $C_1$–$C_6$-alkoxy, $C_1$–$C_6$-halogenoalkyl or $C_1$–$C_6$-halogenoalkoxy,
$R^3$ represents $C_1$–$C_8$-alkyl which is optionally substituted by halogen or represents phenyl or benzyl, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro,
$R^4$ and $R^5$ independently of one another each represent $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio, $C_2$–$C_8$-alkenylthio, $C_3$–$C_7$-cycloalkylthio, each of which is optionally substituted by halogen, or represent phenyl, phenoxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl,
$R^6$ and $R^7$ independently of one another each represent hydrogen, represent $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_1$–$C_8$-alkyl, each of which is optionally substituted by halogen, represent phenyl which is optionally substituted by halogen, $C_1$–$C_8$-halogenoalkyl, $C_1$–$C_8$-alkyl or $C_1$–$C_8$-alkoxy, represent benzyl which is optionally substituted by halogen, $C_1$–$C_8$-alkyl, $C_1$–$C_8$-halogenoalkyl or $C_1$–$C_8$-alkoxy or together represent a $C_3$–$C_6$-alkylene radical in which optionally one methylene group which is not directly adjacent to the nitrogen atom is replaced by oxygen or sulphur,
Q represents

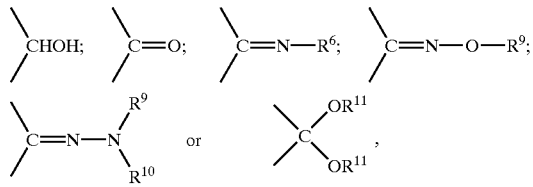

$R^9$ represents hydrogen, represents $C_1$–$C_8$-alkyl which is optionally substituted by halogen, represents $C_3$–$C_8$-cycloalkyl which is *optionally substituted by halogen, $C_1$–$C_4$-alkyl or $C_1$–$C_4$-alkoxy or represents phenyl, benzyl or hetaryl selected from pyridyl, pyrimidyl and thiazolyl, each of which is optionally substituted by halogen, $C_1$–$C_6$-alkyl, $C_1$–$C_4$-alkoxy, $C_1$–$C_4$- halogenoalkyl, C₁–C₄-halogenoalkoxy, nitro or cyano, or represents CO—R¹', CO₂R²', SO₂R¹', CONH₂, CONHR¹¹ or

R¹⁰ represents hydrogen or C₁–C₈-alkyl,
R¹¹ and R¹² are identical or different and each represent C₁–C₆-alkyl or C₃–C₆-alkenyl,
m represents 0 or 1,
R¹' independently of R¹ represents the substituents defined previously within this claim for R¹
and
R²' independently of R² represents the substituents defined previously within this claim for R².

2. A compound of the formula (I) according to claim 1 in which

X represents fluorine, chlorine, bromine, C₁–C₄-alkyl, C₁–C₄-alkoxy, C₁–C₄-halogenoalkyl, C₁–C₄-halogenoalkoxy, nitro or cyano, Y represents hydrogen, fluorine, chlorine, bromine, C₁–C₄-alkyl, C₁–C₄-alkoxy, C₁–C₄-halogenoalkyl, C₁–C₄-halogenoalkoxy, nitro or cyano, Z represents fluorine, chlorine, bromine, C₁–C₄-alkyl, C₁–C₄-halogenoalkyl, C₁–C₄-alkoxy, C₁–C₄-halogenoalkoxy, nitro or cyano, n represents 0, 1 or 2, Het represents one of the groups

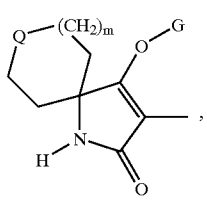
(1)

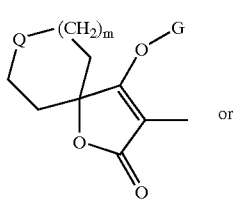
(2) or

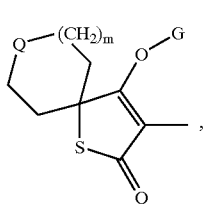
(3)

G represents hydrogen (a) or represents one of the groups

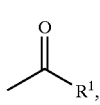
(b)

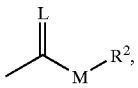
(c)

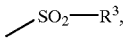
(d)

(e)

E or
(f)

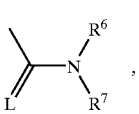
(g)

in which
E represents a metal ion equivalent or an ammonium ion,
L represents oxygen or sulphur and
M represents oxygen or sulphur, R¹ represents C₁–C₁₆-alkyl, C₂–C₁₆-alkenyl, C₁–C₆-alkoxy-C₁–C₆-alkyl or C₁–C₆-alkylthio-C₁–C₆-alkyl, each of which is optionally substituted by fluorine or chlorine, or represents C₃–C₇-cycloalkyl which is optionally substituted by fluorine, chlorine, C₁–C₅-alkyl or C₁–C₅-alkoxy,
represents phenyl which is optionally substituted by fluorine, chlorine, bromine, cyano, nitro, C₁–C₄-alkyl, C₁–C₄-alkoxy, C₁–C₃-halogenoalkyl or C₁–C₃-halogenoalkoxy,
represents phenyl-C₁–C₄-alkyl which is optionally substituted by fluorine, chlorine, bromine, C₁–C₄-alkyl, C₁–C₄-alkoxy, C₁–C₃-halogenoalkyl or C₁–C₃-halogenoalkoxy or
represents pyrazolyl, thiazolyl, pyridyl, pyrimidyl, furanyl or thienyl, each of which is optionally substituted by fluorine, chlorine, bromine or C₁–C₄-alkyl, R² represents C₁–¹⁶-alkyl, C₂–C₁₆-alkenyl, C₁–C₆-alkoxy-C₂–C₆-alkyl or poly-C₁–C₆-alkoxy-C₂–C₆-alkyl, each of which is optionally substituted by fluorine,
represents C₃–C₇-cycloalkyl which is optionally substituted by fluorine, chlorine, C₁–C₄-alkyl or C₁–C₄-alkoxy or represents phenyl or benzyl, each of which is optionally substituted by fluorine, chlorine, bromine, cyano, nitro, C₁–C₄-alkyl, C₁–C₃-alkoxy, C₁–C₃-halogenoalkyl or C₁–C₃-halogenoalkoxy, R³ represents C₁–C₆-alkyl which is optionally substituted by fluorine or chlorine or represents phenyl or benzyl, each of which is optionally substituted by fluorine, chlorine, bromine, C₁–C₅-alkyl, C₁–C₅-alkoxy, C₁–C₃-halogenoalkyl, C₁–C₃-halogenoalkoxy, cyano and nitro, R⁴ and R⁵ independently of one another each represent C₁–C₆-alkyl, C₁–C₆-alkoxy, C₁–C₆-alkylamino, di-(C₁–C₆-alkyl)amino, C₁–C₆-alkylthio, C₃–C₄-alkenylthio or C₃–C₆-cycloalkylthio, each of which is optionally substituted by fluorine or chlorine, or represents phenyl, phenoxy, phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl, $R^6$ and $R^7$ independently of one another each represent hydrogen, represent $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_1$–$C_6$-alkyl, each of which is optionally substituted by fluorine or chlorine, represent phenyl which is optionally substituted by halogen, $C_1$–$C_5$-halogenoalkyl, $C_1$–$C_5$-alkyl or $C_1$–$C_5$-alkoxy, represent benzyl which is optionally substituted by halogen, $C_1$–$C_5$-alkyl, $C_1$–$C_5$-halogenoalkyl or $C_1$–$C_5$-alkoxy or together represent a $C_3$–$C_6$-alkylene radical in which optionally one methylene group which is not directly adjacent to the nitrogen atom is replaced by oxygen or sulphur, Q represents

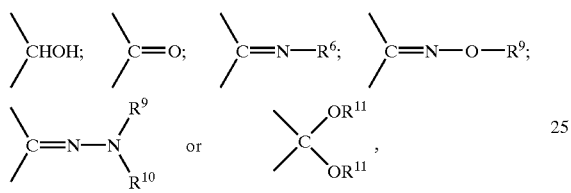

$R^9$ represents hydrogen, represents $C_1$–$C_6$-alkyl, which is optionally substituted by fluorine or chlorine, represents $C_3$–$C_7$-cycloalkyl or represents phenyl or benzyl, each of which is optionally substituted by fluorine, chlorine, bromine, $C_1$–$C_5$-alkyl, $C_1$–$C_4$-alkoxy, $C_1$–$C_2$-halogenoalkyl, $C_1$–$C_2$-halogenoalkoxy, nitro or cyano, represents pyrimidiyl or thiazolyl or represents CO—$R^{1'}$, $CO_2R^{2'}$, $SO_2R^{1'}$, $CONH_2$, $CONHR^{11}$ or $$CON\begin{matrix}R^{11}\\R^{12}\end{matrix},$$

$R^{10}$ represents hydrogen or $C_1$–$C_6$-alkyl,
$R^{11}$ and $R^{12}$ are identical or different and each represents $C_1$–$C_4$-alkyl,
m represents 1,
$R^{1'}$ independently of $R^1$ represents the substituents defined previously within this claim 3 for $R^1$ and
$R^{2'}$ independently of $R^2$ represents the substituents defined previously within this claim 3 for $R^2$.

3. A compound of the formula (I) according to claim 1, in which

X represents fluorine, chlorine, bromine, methyl, ethyl, n-propyl, iso-propyl, methoxy, ethoxy, n-propoxy, iso-propoxy, trifluoromethyl, difluoromethoxy, trifluoromethoxy, nitro or cyano, Y represents hydrogen, fluorine, chlorine, bromine, methyl, ethyl, n-propyl, i-propyl, n-butyl, i-butyl, tert-butyl, methoxy, ethoxy, n-propoxy, iso-propoxy, trifluoromethyl, difluoromethoxy, trifluoromethoxy, nitro or cyano, Z represents fluorine, chlorine, bromine, methyl, ethyl, n-propyl, i-propyl, n-butyl, i-butyl, tert-butyl, methoxy, ethoxy, n-propoxy, iso-propoxy, difluoromethoxy, trifluoromethoxy, nitro or cyano, n represents 0, 1 or 2, Het represents one of the groups

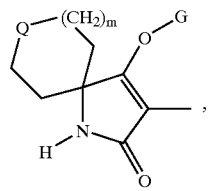
(1)

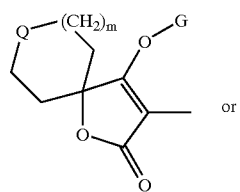
or
(2)

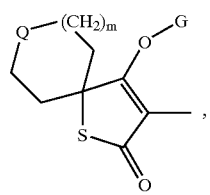
(3)

G represents hydrogen (a) or represents one of the groups (b)
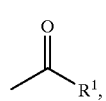

(c)
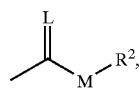

(d)
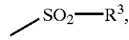

(e)
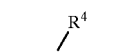

(f)
E or (g)
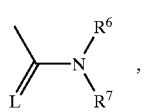

in which
E represents a metal ion equivalent or an ammonium ion,
L represents oxygen or sulphur and
M represents oxygen or sulphur,
$R^1$ represents $C_1$–$C_{14}$-alkyl, $C_2$–$C_{14}$-alkenyl, $C_1$–$C_4$-alkoxy-$C_1$–$C_6$-alkyl or $C_1$–$C_4$-alkylthio-$C_1$–$C_6$-alkyl, each of which is optionally substituted by fluorine or chlorine, or represents $C_3$–$C_6$-cycloalkyl, which is optionally substituted by methyl, ethyl, tert-butyl or methoxy,
represents phenyl which is optionally substituted by fluorine, chlorine, bromine, cyano, nitro, methyl, methoxy, trifluoromethyl or trifluoromethoxy, represents benzyl which is optionally substituted by fluorine, chlorine, bromine, methyl, methoxy, trifluoromethyl or trifluoromethoxy or represents furanyl, thienyl or pyridyl, each of which is optionally substituted by fluorine, chlorine, bromine or methyl, $R^2$ represents $C_1-C_{14}$-alkyl, $C_2-C_14$-alkenyl or $C_1-C_4$-alkoxy-$C_2-C_6$-alkyl, represents $C_3-C_6$-cycloalkyl which is optionally substituted by methyl or methoxy or represents phenyl or benzyl, each of which is optionally substituted by fluorine, chlorine, bromine, cyano, nitro, methyl, methoxy, trifluoro-methyl or trifluoromethoxy, $R^3$ represents methyl, ethyl, n-propyl, isopropyl, each of which is optionally substituted by fluorine or chlorine, or represents phenyl or benzyl, each of which is optionally substituted by fluorine, chlorine, bromine, methyl, ethyl, n-propyl, iso-propyl, tert-butyl, methoxy, ethoxy, isopropoxy, tert-butoxy, trifluoromethyl, trifluoromethoxy, cyano or nitro, $R^4$ and $R^5$ independently of one another each represent $C_1-C_4$-alkyl, $C_1-C_4$-alkoxy, $C_1-C_4$-alkylamino, di-($C_1-C_4$-alkyl)amino or $C_1-C_4$-alkylthio, each of which is optionally substituted by fluorine or chlorine, or represent phenyl, phenoxy or phenylthio, each of which is optionally substituted by fluorine, chlorine, bromine, nitro, cyano, $C_1-C_2$-alkoxy, $C_1-C_2$-fluoroalkoxy, $C_1-C_2$-alkylthio, $C_1-C_2$-fluoroalkylthio or $C_1-C_3$-alkyl, $R^6$ and $R^7$ independently of one another each represent hydrogen, represent $C_1-C_4$-alkyl, $C_3-C_6$-cycloalkyl, $C_1-C_4$-alkoxy, $C_3-C_4$-alkenyl or $C_1-C_4$-alkoxy-$C_1-C_4$-alkyl, each of which is optionally substituted by fluorine or chlorine, represent phenyl which is optionally substituted by fluorine, chlorine, bromine, trifluoromethyl, methyl or methoxy, represent benzyl which is optionally substituted by fluorine, chlorine, bromine, $C_1-C_4$-alkyl, $C_1-C_4$-halogenoalkyl or $C_1-C_4$-alkoxy or together represent a $C_5-C_6$-alkylene radical in which optionally one methylene group which is not directly adjacent to nitrogen atom may be replaced by oxygen or sulphur, Q represents

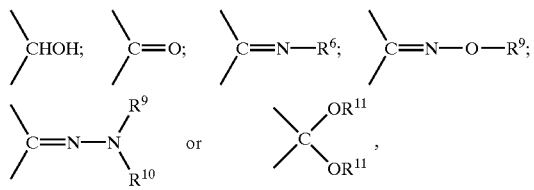

$R^9$ represents hydrogen, represents $C_1-C_4$-alkyl, represents $C_3-C_6$-cycloalkyl or represents phenyl or benzyl, each of which is optionally substituted by fluorine, chlorine, bromine, methyl, ethyl, n-propyl, iso-propyl, tert-butyl, methoxy, trifluoromethyl, trifluoromethoxy, nitro or cyano, or represents CO—$R^{1'}$, $CO_2R^{2'}$, $SO_2R^{1'}$, $CONH_2$, $CONHR^{11}$ or

$R^{10}$ represents hydrogen or methyl, $R^{11}$ and $R^{12}$ are identical or different and each represents methyl or ethyl, m represents 1, $R^{1'}$ independently of $R^1$ represents the substituents defined previously within this claim 4 for $R^1$ and $R^{2'}$ independently of $R^2$ represents the substituents defined previously within in this claim 4 for $R^2$.

4. A process for preparing compounds of the formula (I) according to claim 1, characterised in that to obtain compounds (A) of the formula (I-1-a)

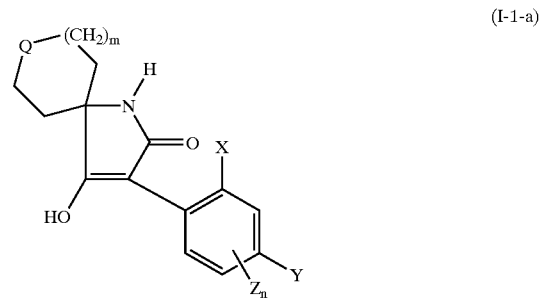

(I-1-a)

in which

Q, X, Y, Z, m and n are each as defined in claim 2, compounds of the formula (II)

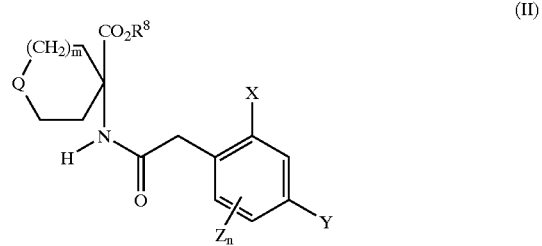

(II)

in which

Q, X, Y, Z, m and n are each as defined in claim 2, and $R^8$ represents alkyl are intramolecularly condensed in the presence of a diluent and in the presence of a base, (B) to obtain compounds of the formula (I-2-a)

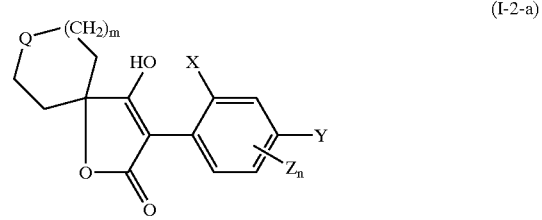

(I-2-a)

in which

Q, X, Y, Z, m and n are each as defined in claim 2, compounds of the formula (III)

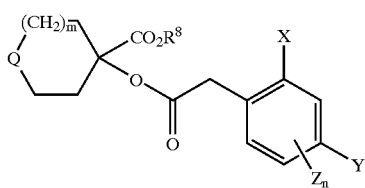
(III)

in which

Q, X, Y, Z, m, and n are each as defined in claim 2 and $R^8$ is as previously defined in this claim 5, are intramolecularly condensed in the presence of a diluent and in the presence of a base, (C) to obtain compounds of the formula (I-3-a)

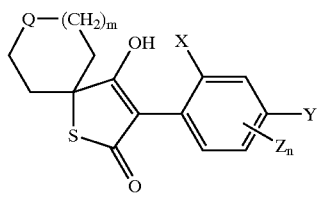
(I-3-a)

in which

Q, X, Y, Z, m and n are each as defined in claim 2, compounds of the formula (IV)

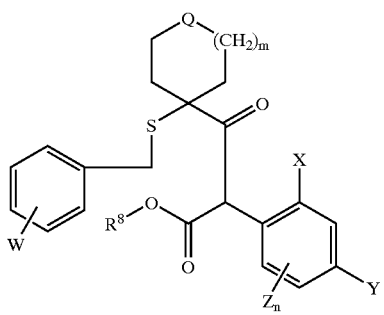
(IV)

in which

Q, X, Y, Z, m and n are as defined in claim 2 and $R^8$ is as defined in this claim 5, and W represents hydrogen, halogen, alkyl, preferably $C_1$–$C_6$ alkyl, or alkoxy, preferably $C_1$–$C_8$-alkoxy are intramolecularly cyclized in the presence of a diluent and in the presence of an acid, and the resulting compounds of the formulae (I-1-a), (I-2-a) and (I-3-a) are each optionally subsequently (Dα) reacted with acyl chlorides of the formula (V)

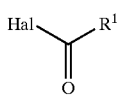
(V)

in which $R^1$ is as defined in claim 2 and

Hal represents halogen or (Dβ) reacted with carboxylic anhydrides of the formula (VI)

$$R^1—CO—O—CO—R^1 \qquad (VI)$$

in which $R^1$ is as defined in claim 2, optionally in the presence of a diluent and optionally in the presence of an acid binder; or (E) reacted with chloroformic acid esters or chloroformic acid thiol esters of the formula (VII)

$$R^2—M—CO—Cl \qquad (VII)$$

in which $R^2$ and M are each as defined in claim 2, optionally in the presence of a diluent and optionally in the presence of an acid binder; or (F) reacted with chloromonothioformic acid esters or chlorodithioformic acid esters of the formula (VIII)

(VIII)

in which

M and $R^2$ are each as defined in claim 2, optionally in the presence of a diluent and optionally in the presence of an acid binder; or (G) reacted with sulphonyl chlorides of the formula (IX)

$$R^3—SO_2—Cl \qquad (IX)$$

in which $R^3$ is as defined in claim 2, optionally in the presence of a diluent and optionally in the presence of an acid binder; or (H) reacted with phosphorus compounds of the formula (X)

(X)

in which

L, $R^4$ and $R^5$ are each as defined in claim 2 and

Hal represents halogen, optionally in the presence of a diluent and optionally in the presence of an acid binder; or (I) reacted with metal compounds or amines of the formula (XI) or (XII)

$$Me(OR^{13})_t \qquad (XI)$$

(XII)

in which

Me represents a mono- or divalent metal, t represents 1 or 2 and $R^{13}, R^{14}, R^{15}$ independently of one another each represent hydrogen or alkyl, optionally in the presence of a diluent; or (Jα) reacted with isocyanates or isothiocyanates of the formula (XIII)

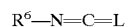
(XIII)

in which $R^6$ and L are each as defined in claim 2, optionally in the presence of a diluent and optionally in the presence of a catalyst or (Jβ) reacted with carbamoyl chlorides or thiocarbamoyl chlorides of the formula (XIV)

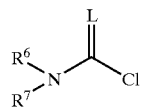
(XIV)

in which

L, $R^6$ and $R^7$ are each as defined in claim 2, optionally in the presence of a diluent and optionally in the presence of an acid binder.

5. A compound of the formula (II) of claim 4

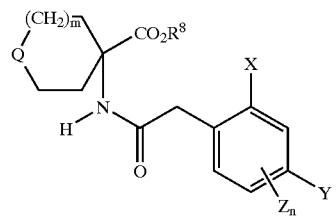
(II)

in which

Q, X, Y, Z, m and n are each as defined in claim 5 and $R^8$ represents alkyl.

6. A compound of the formula (XVII)

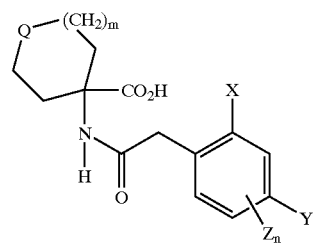
(XVII)

in which

Q, m, X, Y, Z and n are each as defined in claim 1.

7. A compound of the formula (III) of claim 4

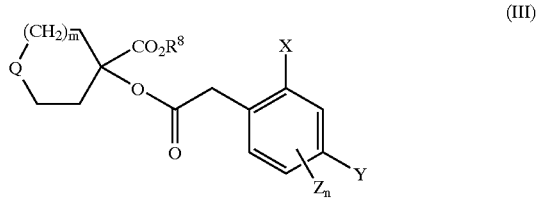
(III)

in which

Q, X, Y, Z, m and n are each as defined in claim 4 and $R^8$ represents alkyl.

8. A compound of the formula (IV) of claim 4

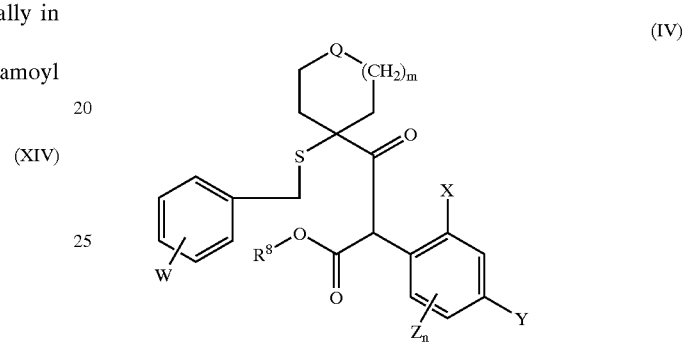
(IV)

in which

Q, W, X, Y, Z, m and n are each as defined in claim 5 and $R^8$ represents alkyl.

9. A pesticide or herbicide composition comprising, a compound of the formula (I) according to claim 1 and an element selected from the group consisting of a diluent, an inert carrier and combinations thereof.

10. A method for controlling pests and/or weeds comprising applying an effective amount of a compound of the formula (I) according to claim 1 to said pests and/or weeds, respectively, and/or their habitat to control said pests and/or weeds.

11. A process for preparing pesticides and herbicides comprising mixing compounds of the formula (I) according to claim 1 with extenders and/or surfactants.

12. A compound of the formula (I)

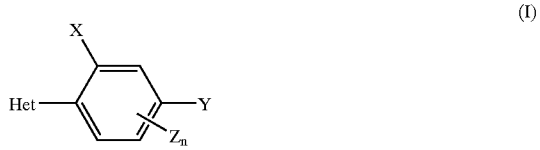
(I)

in which

X represents halogen, $C_1$–$C_6$-alkyl, $C_2$–$C_6$-alkenyl, $C_2$–$C_6$-alkinyl, $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkyl, $C_2$–$C_6$-halogenoalkenyl, $C_1$–$C_6$-halogenoalkoxy, $C_3$–$C_6$-halogenoalkenyloxy, nitro, cyano or represents phenyl, phenoxy, phenylthio, benzyloxy or benzylthio, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, Y represents hydrogen, halogen, $C_1$–$C_6$-alkyl, $C_2$–$C_6$-alkenyl, $C_2$–$C_6$-alkinyl, $C_1$–$C_6$-alkoxy, $C_3$–$C_6$- alkenyloxy, $C_1$–$C_6$-alkylthio, $C_1$–$C_6$-alkyls $C_1$–$C_6$-alkylsulphonyl, $C_1$–$C_6$-halogenoalkyl, $C_2$–$C_6$-halogenoalkenyl, $C_1$–$C_6$-halogenoalkoxy, $C_3$–$C_6$-halogenoalkenyloxy, nitro or cyano, Z represents halogen, $C_1$–$C_6$-alkyl, $C_2$–$C_6$-alkenyl, $C_2$–$C_6$-alkinyl, $C_1$–$C_6$-halogenoalkyl, $C_2$–$C_6$-halogenoalkenyl, $C_1$–$C_6$-alkoxy, $C_3$–$C_6$-alkenyloxy, $C_1$–$C_6$-halogenoalkoxy, $C_3$–$C_6$-halogenoalkenyloxy, nuitro or cyano, n represents 0, 1, 2 or 3, Het represents one of the groups

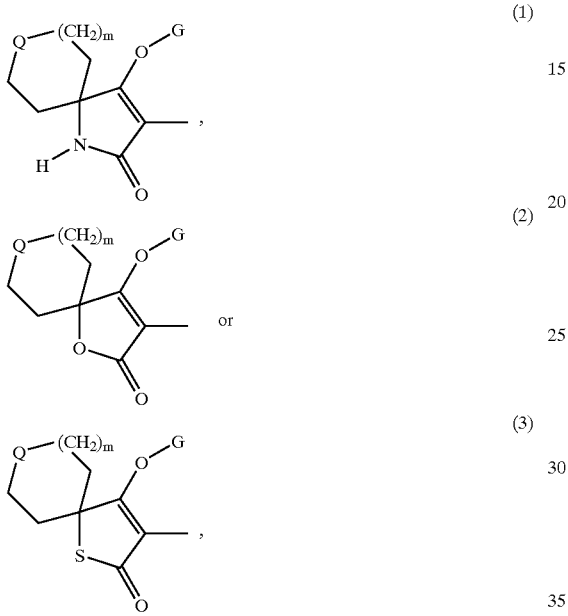

G represents hydrogen (a) or represents one of the groups

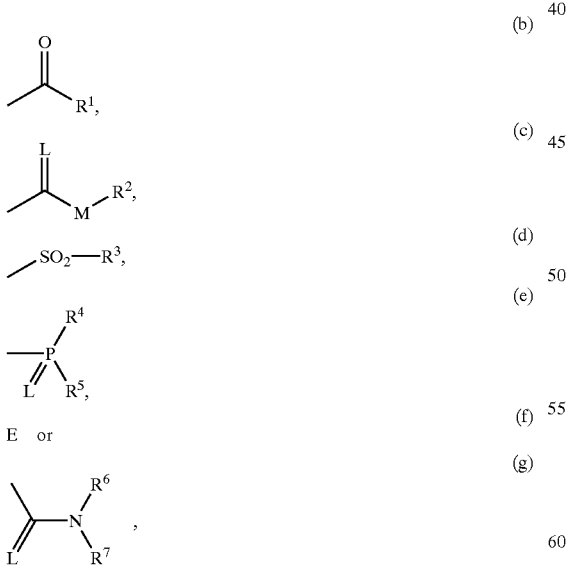

in which
E represents a metal ion equivalent or an ammonium ion,
L represents oxygen or sulphur and
M represents oxygen or sulphur, $R^1$ represents $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl, each of which may optionally be substituted with halogen, represents $C_3$–$C_8$-cycloalkyl which may optionally be substituted by halogen, $C_1$–$C_6$-alkyl or $C_1$–$C_6$-alkoxy and in which optionally one or at most two not directly adjacent methylene groups may be replaced by oxygen and/or sulphur, represents phenyl which is optionally substituted by halogen, cyano, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio or $C_1$–$C_6$-alkylsulphonyl, represents phenyl-$C_1$–$C_6$-alkyl, which is optionally substituted by halogen, nitro, cyano, $C_1$–$C_6$-alkyl, $C_1$–$C_6$-alkoxy, $C_1$–$C_6$-halogenoalkyl or $C_1$–$C_6$-halogenoalkoxy, represents 5- or 6-membered hetaryl selected from pyrazolyl, thiazolyl, pyridyl, pyrimidyl, furanyl and thienyl each of which is optionally substituted by halogen or $C_1$–$C_6$-alkyl, represents phenoxy-$C_1$–$C_6$-alkyl which is optionally substituted by halogen or $C_1$–$C_6$-alkyl or represents 5- or 6-membered hetaryloxy-$C_1$–$C_6$-alkyl which is optionally substituted by halogen, amino or $C_1$–$C_6$-alkyl, $R^2$ represents $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, each of which is optionally substituted by halogen, represents $C_3$–$C_8$-cycloalkyl which is optionally substituted by halogen, $C_1$–$C_6$-alkyl or $C_1$–$C_6$-alkoxy or represents phenyl or benzyl, each of which is optionally substituted by halogen, cyano, nitro, $C_1$–$C_6$-alkyl, $C_1$–$C_6$-alkoxy, $C_1$–$C_6$-halogenoalkyl or $C_1$–$C_6$-halogenoalkoxy, $R^3$ represents $C_1$–$C_8$-alkyl which is optionally substituted by halogen or represents phenyl or benzyl, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, $R^4$ and $R^5$ independently of one another each represent $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio, $C_2$–$C_8$-alkenylthio, $C_3$–$C_7$-cycloalkylthio, each of which is optionally substituted by halogen, or represent phenyl, phenoxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl, $R^6$ and $R^7$ independently of one another each represent hydrogen, represent $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_1$–$C_8$-alkyl, each of which is optionally substituted by halogen, represent phenyl which is optionally substituted by halogen, $C_1$–$C_8$-halogenoalkyl, $C_1$–$C_8$-alkyl or $C_1$–$C_8$-alkoxy, represent benzyl which is optionally substituted by halogen, $C_1$–$C_8$-alkyl, $C_1$–$C_8$-halogenoalkyl or $C_1$–$C_8$-alkoxy or together represent a $C_3$–$C_6$-alkylene radical in which optionally one methylene group which is not directly adjacent to the nitrogen atom is replaced by oxygen or sulphur, Q represents

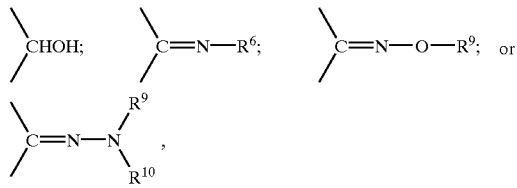

$R^9$ represents hydrogen, represents $C_1$–$C_8$-alkyl which is optionally substituted by halogen, represents $C_3$–$C_8$-cycloalkyl which is optionally substituted by halogen, $C_1$–$C_4$-alkyl or $C_1$–$C_4$-alkoxy or represents phenyl, benzyl or hetaryl selected from pyridyl, pyrimidyl and thiazolyl, each of which is optionally substituted by halogen, $C_1$–$C_6$-alkyl, $C_1$–$C_4$-alkoxy, $C_1$–$C_4$-halogenoalkyl, $C_1$–$C_4$-halogenoalkoxy, nitro or cyano, or represents CO—$R^{1'}$, $CO_2R^{2'}$, $SO_2R^{1'}$, $CONH_2$, $CONHR^{11}$ or

$R^{10}$ represents hydrogen or $C_1$–$C_8$-alkyl, $R^{11}$ and $R^{12}$ are identical or different and each represent $C_1$–$C_6$-alkyl or $C_3$–$C_6$-alkenyl, m represents 0 or 1, $R^{1'}$ independently of $R^1$ represents the substituents defined previously within this claim for $R^1$ and $R^{2'}$ independently of $R^2$ represents the substituents defined previously within this claim for $R^2$.

13. A compound of the formula (I) according to claim 1, wherein n is 1, 2, or 3.

14. A compound of the formula (I) according to claim 12, wherein n is 1, 2 or 3.

* * * * *